US012788280B2

(12) United States Patent
Rao et al.

(10) Patent No.: US 12,788,280 B2
(45) Date of Patent: Nov. 10, 2026

(54) SYSTEMS, DEVICES, AND METHODS FOR ANALYTE MONITORING

(71) Applicant: ABBOTT DIABETES CARE INC., Alameda, CA (US)

(72) Inventors: Vivek S. Rao, Alameda, CA (US); Joshua Lindsay, Woodside, CA (US); Matthew Simmons, Pleasanton, CA (US); Steven T. Mitchell, Pleasant Hill, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 361 days.

(21) Appl. No.: 18/443,761

(22) Filed: Feb. 16, 2024

(65) Prior Publication Data

US 2024/0277262 A1 Aug. 22, 2024

Related U.S. Application Data

(60) Provisional application No. 63/553,562, filed on Feb. 14, 2024, provisional application No. 63/446,453, filed on Feb. 17, 2023.

(51) Int. Cl.
*A61B 5/145* (2006.01)
*A61B 5/00* (2006.01)

(52) U.S. Cl.
CPC ........ *A61B 5/14503* (2013.01); *A61B 5/6849* (2013.01); *A61B 2560/063* (2013.01)

(58) Field of Classification Search
CPC ............ A61B 5/14546; A61B 5/14503; A61B 5/6848; A61B 5/14532; A61M 5/314; A61M 5/2026; A61M 5/2033
See application file for complete search history.

(56) References Cited

U.S. PATENT DOCUMENTS

| | | | | |
|---|---|---|---|---|
| 4,924,878 | A * | 5/1990 | Nottke ............... | A61B 10/0275 600/564 |
| 10,213,139 | B2 | 2/2019 | Rao et al. | |
| 2011/0288574 | A1* | 11/2011 | Curry ............... | A61B 5/150022 606/185 |

(Continued)

FOREIGN PATENT DOCUMENTS

WO WO 2022/046416 A1 3/2022

OTHER PUBLICATIONS

WO PCT/US2024/016127 ISR and Written Opinion Sep. 11, 2024.
WO PCT/US2024/016127 Invitation to Pay Additional Fees Jun. 4, 2024.

*Primary Examiner* — Jason M Sims
*Assistant Examiner* — Ari S Padda
(74) *Attorney, Agent, or Firm* — ONE LLP

(57) ABSTRACT

Systems, devices and methods are provided for inserting at least a portion of a sensor for sensing an analyte level in a bodily fluid of a subject. In particular, disclosed herein are various embodiments of reset tools for resetting an insertion apparatus, and containers for storing an analyte monitoring assembly. The analyte monitoring assembly can be a combination of components used for monitoring an analyte of the subject. The containers described herein can be used to load an analyte monitoring assembly into an insertion apparatus. The insertion apparatus can then be used to insert at least a portion of the sensor into the subject's skin. The insertion apparatus can be reusable.

20 Claims, 39 Drawing Sheets

(56) References Cited

U.S. PATENT DOCUMENTS

| | | | | |
|---|---|---|---|---|
| 2012/0303043 | A1* | 11/2012 | Donnay | A61B 5/6849 606/129 |
| 2014/0171771 | A1 | 6/2014 | Feldman et al. | |
| 2014/0276414 | A1* | 9/2014 | Baker | A61M 5/20 434/262 |
| 2015/0018643 | A1 | 1/2015 | Cole et al. | |
| 2019/0133501 | A1* | 5/2019 | Rao | A61B 5/14503 |
| 2020/0289748 | A1* | 9/2020 | Lanigan | A61M 5/158 |
| 2022/0125480 | A1 | 4/2022 | Rao et al. | |
| 2022/0202448 | A1* | 6/2022 | Shah | A61B 5/14532 |
| 2024/0252749 | A1* | 8/2024 | Pananen | A61M 5/14248 |

* cited by examiner

SYSTEMS, DEVICES, AND METHODS FOR ANALYTE MONITORING

CROSS-REFERENCE TO RELATED APPLICATIONS

This application claims priority to U.S. Application Ser. No. 63/553,562, Feb. 14, 2024, and U.S. Application Ser. No. 63/446,453, filed Feb. 17, 2023, which are hereby expressly incorporated by reference in their entireties for all purposes.

FIELD

The subject matter described herein relates generally to systems, devices, and methods for in vivo analyte monitoring. In particular, the present disclosure relates to a container for storing an analyte monitoring assembly and a resettable applicator.

BACKGROUND

The detection and/or monitoring of analyte levels, such as glucose, ketones, lactate, oxygen, hemoglobin A1C, or the like, can be vitally important to the overall health of a person, particularly for an individual having diabetes. Patients suffering from diabetes mellitus can experience complications including loss of consciousness, cardiovascular disease, retinopathy, neuropathy, and nephropathy. Persons with diabetes are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and provide discreet monitoring to encourage frequent analyte monitoring to improve glycemic control. Additionally, there is a need for such analyte monitoring devices, systems, and methods that reduce pain and trauma associated with analyte monitoring and testing.

While current sensors can be convenient for users, they are also susceptible to malfunctions. These malfunctions can be caused by user error, lack of proper training, poor user coordination, overly complicated procedures, physiological responses to the inserted sensor, and other issues. This can be particularly true for analyte monitoring systems having sensors used to measure an analyte level in ISF, and which are inserted using sharps (also known as "introducers" or "needles"). In addition, some prior art systems may utilize sharps that can create trauma to surrounding tissue at the sensor insertion site, which can lead to inaccurate analyte level measurements. These challenges and others described herein can lead to a failure to properly monitor the patient's analyte level.

Thus, a need exists for more reliable sensor insertion devices, systems and methods, that are easy to use by the patient, less prone to error, and which reduce trauma to an insertion site.

SUMMARY

According to a first aspect of the present disclosure, there is provided a container for storing an analyte monitoring assembly, the container comprising: a container body; an analyte monitoring assembly arranged within the container body, wherein the analyte monitoring assembly comprises: an analyte sensor, wherein at least a portion of the analyte sensor is configured for insertion into skin of a subject; and a sensor control device comprising sensor electronics for operating the analyte sensor; wherein the analyte sensor is coupled to the sensor control device; and a closure configured to seal the container body with the analyte monitoring assembly arranged therein; and wherein the container is configured for engagement with an insertion apparatus, after opening of the closure, to remove the analyte monitoring assembly from the container body for inserting the at least a portion of the analyte sensor into the skin of the subject.

In other words, the container provides storage for the analyte monitoring assembly until it is removed by an insertion apparatus. In particular, the container can be used to load the analyte monitoring assembly into the insertion apparatus. The closure can be opened, such as by removing the closure from the container body if the closure is removable, or otherwise opening the closure if it is integral, and the insertion apparatus can be engaged with the container to remove the analyte monitoring assembly from the container body. The insertion apparatus can then be used to insert at least a portion of a sensor into skin of a subject. In addition, the sensor control device can be applied to the skin, for example by attachment to the skin as described herein. In some embodiments, the container can be used with a reusable insertion apparatus (e.g., a reusable applicator). By providing the analyte monitoring assembly within the container, the insertion apparatus can be reusable, and the analyte monitoring assembly can be loaded into the insertion apparatus. Once the analyte monitoring assembly is released onto the skin with the analyte sensor inserted, the insertion apparatus can then be reused by loading another analyte monitoring assembly from a second container.

The container body can have an open end to which the closure is applied. The open end can be the proximal end. The opposite end can be closed at the distal end. Thus, the container body can form a cup-shape.

In some embodiments, the container further comprises a sensor cap having a first end configured to be removably attached to the analyte monitoring assembly, wherein the sensor cap is arranged to extend over at least a portion of the analyte sensor. The sensor cap can be used to maintain sterility of the sensor. As the sensor cap is removably attached, it can be removed to expose the sensor for insertion. The sensor cap can be removed as part of the process of loading the analyte monitoring assembly into the insertion apparatus.

In some embodiments, the sensor cap comprises an interface element for engaging with the container body. This allows the sensor cap to interact and control movement with the container body. For example, the interface element can be a protrusion, such as a ramp, for contacting the container body.

In some embodiments, the container body comprises a retaining element for engaging with the interface element of the sensor cap. This allows the container body to interact with the sensor cap.

In some embodiments, the retaining element of the container body is configured to engage with the interface element of the sensor cap to support the sensor cap in a first configuration. The retaining element can restrict proximal movement of the sensor cap. The retaining element can be used to keep the sensor cap in position. For example, the retaining element can be arranged proximally (towards the closure) of the interface element, to prevent movement of the interface element proximally past the retaining element.

In some embodiments, the retaining element of the container body is configured to engage with the interface element of the sensor cap under application of a proximal force on the analyte monitoring assembly relative to the container body. For example, the insertion apparatus can cause the proximal force. In the event of a force in the proximal direction (towards the open end of the container), such as the insertion apparatus withdrawing the analyte monitoring assembly from the container body, the retaining element can act to restrict proximal movement of the sensor cap and prevent the sensor cap from being withdrawn.

In some embodiments, the sensor cap is configured to detach from the analyte monitoring assembly into a second configuration in response to a proximal force on the analyte monitoring assembly relative to the container body. For example, the insertion apparatus can cause the proximal force. The retaining element can be configured to cause the sensor cap to disengage and detach from the analyte monitoring assembly at the first end of the sensor cap in response to the proximal force. This can allow the analyte monitoring assembly to be released while retaining the sensor cap. The container can be configured to retain the sensor cap whilst releasing the analyte monitoring assembly in response to a proximal force on the analyte monitoring assembly, such as by an insertion apparatus. This allows the analyte monitoring assembly to be removed from the container, whilst removing the sensor cap, exposing the sensor ready for insertion.

In some embodiments, the retaining element of the container body is configured to engage with the interface element of the sensor cap to detach the sensor cap from the analyte monitoring assembly into a second configuration in response to a proximal force on the analyte monitoring assembly relative to the container body. The retaining element can interact with the interface element to retain the sensor cap whilst the sensor cap releases the analyte monitoring assembly.

In some embodiments, the sensor cap is configured to rotate to detach from the analyte monitoring assembly into a second configuration in response to a proximal force on the analyte monitoring assembly relative to the container body. By rotating the sensor cap, the sensor cap can unscrew from the analyte monitoring assembly to detach. By rotating in response to the proximal force, the sensor cap can be removed during removal of the analyte monitoring assembly from the container body.

In some embodiments, the retaining element of the container body is configured to engage with the interface element of the sensor cap to rotate the sensor cap to detach the sensor cap from the analyte monitoring assembly into a second configuration in response to a proximal force on the analyte monitoring assembly relative to the container body. The retaining element can be used to rotate the sensor cap by interaction with the interface element. In other words, in response to the insertion apparatus withdrawing the analyte monitoring assembly with a proximal force, the retaining element can cause the sensor cap to rotate and unscrew from the analyte monitoring assembly, thereby releasing the analyte monitoring assembly but retaining the sensor cap.

In some embodiments, the analyte monitoring assembly is removable from the container body when the sensor cap is in the second configuration. By detaching the sensor cap from the analyte monitoring assembly, the analyte monitoring assembly can be free to move proximally, and can be removed from the container body, such as by the insertion apparatus.

In some embodiments, the retaining element is configured to retain the sensor cap within the container body when the sensor cap is detached from the analyte monitoring assembly in the second configuration. This allows the sensor cap to be kept in position, exposing the sensor for later insertion. For example, the container can be configured to prevent the sensor cap from being released after detaching from the analyte monitoring assembly. This allows the analyte monitoring assembly to be properly detached and the analyte sensor properly exposed, while avoiding the sensor cap from being a loose article and dropping out of the container body.

In some embodiments, the interface element comprises a ramp extending along an outer surface of the sensor cap. For example, the ramp can extend partly in a lengthwise manner and partly in a circumferential manner along the outer surface. For example, the ramp can extend in a generally helical shape. The ramp can be used to interact with the interface element to guide the movement of the sensor cap relative to the container body in response to the proximal force. The retaining element can then cause movement of the interface element rotationally. This can provide the rotation of the sensor cap in response to the proximal force.

In some embodiments, the sensor cap comprises an end stop at the distal end of the ramp, and wherein the retaining element is configured to engage with the end stop to prevent further proximal movement of the sensor cap relative to the container body in the second configuration to retain the sensor cap within the container body. This limits the movement of the interface element along the ramp, and retains the sensor cap to prevent release of the sensor cap. For example, the ramp can be U-shaped.

In some embodiments, the container further comprises a plug configured to engage a second end of the sensor cap opposite the first end, wherein the sensor cap and the plug are together configured to seal the analyte sensor. This can seal the sensor to maintain sterility.

In some embodiments, the plug is configured to engage the container body to support the sensor cap. This can be used to keep the analyte monitoring assembly in place and align the analyte monitoring assembly.

In some embodiments, the plug is integral with the container body. This means the container body can become part of the sterile interface. In other examples, the plug is a separate component which is attached to the sensor cap, such as before loading the sensor cap into the container body. This allows the sensor cap to be sealed and sterilized.

In some embodiments, the container body is configured to support the analyte monitoring assembly in position within the container body. The container body can be used to hold the analyte monitoring assembly in position, such as by retaining the sensor control device.

In some embodiments, the sensor control device comprises a housing. For example, the housing can comprise a shell having a lower shell and an upper shell. The sensor electronics can be housed within the housing (or shell). The housing (or shell) can be supported by the container body and/or the closure.

In some embodiments, the sensor control device comprises an adhesive patch attached to a base surface of the housing. For example, the adhesive patch can be attached to the lower shell of the shell. The adhesive patch can be used for attaching the sensor control device to the skin. The sensor control device can be attached to the skin when the analyte sensor is inserted into the skin.

In some embodiments, the container body comprises at least one alignment feature for aligning the sensor control device within the container body. This allows the sensor control device to be properly positioned and oriented to allow for easier removal by the insertion apparatus.

In some embodiments, the at least one alignment feature comprises a plurality of alignment posts configured to be received within respective alignment holes of the sensor control device. The alignment posts can be used to prevent rotation of the sensor control device. The sensor control device, for example the housing, can thus have alignment holes for receiving the alignment posts. This allows for easier alignment of the insertion apparatus with the sensor control device for removing the analyte monitoring assembly.

In some embodiments, the sensor control device is arranged such that a clearance is provided between the adhesive patch and the container body. This prevents the adhesive attaching to the container body.

In some embodiments, the closure comprises a support element configured to engage the analyte monitoring assembly. This means the closure can be used to support the analyte monitoring assembly in position during storage until use and the closure is removed. For example, the support element can engage the sensor control device, such as the housing.

In some embodiments, the container body comprises an insertion apparatus alignment feature for engaging with the insertion apparatus. For instance, a surface feature on the outer surface of the container body can aid alignment of the insertion apparatus for removing the analyte monitoring assembly. Thus, the container is adapted for engaging with the insertion apparatus to allow removal of the analyte monitoring assembly.

In some embodiments, the container body comprises a gripping feature on an outer surface of the container body. The gripping feature can aid user grip for improving ease of use in removing the analyte monitoring assembly from the container.

In some embodiments, the container body comprises a first portion for housing the sensor control device.

In some embodiments, the container body comprises a second portion for housing at least a portion of the sensor.

In some embodiments, the second portion has an outer width smaller than an outer width of the first portion. This can provide a smaller diameter portion being easier to hold in the hand of the user.

In some embodiments, the container further comprises a desiccant. This can absorb moisture and unwanted outgassing. In some examples, one or more desiccants (e.g., a plurality of desiccants) can be provided.

In some embodiments, the container further comprises a sharp for assisting insertion of at least a portion of the analyte sensor into the skin. The sharp (otherwise referred to as a needle) can be inserted into the skin, and the sensor can follow, allowing the sensor to be inserted without the sensor penetrating the skin directly. In other embodiments, the sensor can be configured to penetrate the skin and no sharp is required. In some examples, the sharp can be part of the analyte monitoring assembly. For example, the analyte monitoring assembly can comprise the sharp.

In some embodiments, the container further comprises a sharp hub configured to support the sharp. The sharp hub (otherwise referred to as a sharp module or needle hub) can support the sharp and provide an interface for retraction of the sharp following insertion. The sharp hub can be part of the analyte monitoring assembly. Thus, the analyte monitoring assembly can comprise the sharp and the sharp hub. The sharp (and, optionally, the sharp hub) can be removed from the container as part of the analyte monitoring assembly. In some examples, the insertion apparatus is configured to remove the sharp (and, optionally, the sharp hub) from the container body.

In some embodiments, the sharp is arranged to extend through an aperture in the sensor control device, and wherein the sharp is arranged to extend adjacent at least a portion of the analyte sensor. The sharp can be arranged to extend through the sensor control device, such as through an aperture in the housing. The sharp can be arranged to extend adjacent to the analyte sensor, for example, the analyte sensor can extend within the sharp. The analyte sensor can also extend through at least part of the aperture in the sensor control device. For example, the housing of the sensor control device can have an aperture from the upper surface to the lower surface (e.g., in both the upper shell and the lower shell). The sharp can extend through the entire sensor control device, in through the upper shell and out through the lower shell. The analyte sensor can be arranged to extend through the aperture in the lower shell, but the proximal portion is configured to be in electrical contact with the sensor electronics, so is enclosed within the housing and cannot extend through the upper shell.

In some embodiments, the analyte sensor comprises an in vivo glucose sensor configured to measure a glucose level in a bodily fluid of the subject. For example, the sensor can be an implantable sensor such as a partially implantable sensor, wherein a portion of the sensor is implantable (and the other portion is in the sensor control device). The sensor can be a transcutaneous sensor. The sensor can be implantable into bodily fluid such as interstitial fluid of the subject.

According to a second aspect of the present disclosure, there is provided a system comprising: a container as disclosed herein; and an insertion apparatus for inserting the at least a portion of the analyte sensor into the skin of the subject, wherein the insertion apparatus is configured to engage the container and remove the analyte monitoring assembly from the container body of the container. For example, the container can be the container of the first aspect. In some embodiments, the insertion apparatus can be a reusable applicator.

In some embodiments, the insertion apparatus is further configured to insert the at least a portion of the analyte sensor into the skin of the subject and place the sensor control device onto the skin of the subject. In some examples, the insertion apparatus is configured to withdraw the sharp after insertion of the analyte sensor. After withdrawal of the sharp, the sharp can be deposited into the container. Thus, the container can be configured to receive the sharp after insertion of the analyte sensor. In this regard, the container can be used as a receptacle for a used sharp. Additionally, this allows the insertion apparatus to be reusable since the used sharp has been removed.

According to a third aspect of the present disclosure, there is provided a container for storing an analyte monitoring assembly, the container comprising: a container body; an analyte monitoring assembly arranged within the container body, wherein the analyte monitoring assembly comprises: an analyte sensor, wherein at least a portion of the analyte sensor is configured for insertion into skin of a subject; and a sensor control device comprising sensor electronics for operating the analyte sensor; wherein the analyte sensor is coupled to the sensor control device; and wherein the container is configured for engagement with an insertion apparatus to remove the analyte monitoring assembly from the container body for inserting the at least a portion of the analyte sensor into the skin of the subject. In some embodiments, the container can be provided with a separate closure configured to seal the container body with the analyte monitoring assembly arranged therein, when the closure is applied to an open end of the container. In this manner, the closure can be provided separately. In these examples, the insertion apparatus can engage the container after removal of the closure.

According to a fourth aspect of the present disclosure, there is provided a reset tool for resetting an applicator, the reset tool comprising a shaft comprising a hollow interior, a spring-loaded plunger configured to telescopically slide relative to the shaft, the plunger further configured to be inserted into a channel of the applicator, and a tip portion configured to extend into a channel of a sharp carrier of the applicator, wherein the reset tool is configured to advance in a distal direction into the applicator in response to a force, wherein the plunger is further configured to drive the sharp carrier towards a device carrier of the applicator until a portion of the device carrier engages with the sharp carrier, and wherein the shaft is configured to drive a sheath of the applicator in a distal direction upon the portion of the device carrier engaging with the sharp carrier. For example, the applicator may be an applicator for inserting an analyte sensor into skin of a subject. For example, the applicator may be an applicator, such as the reusable applicator, as described herein. This reset tool allows the applicator to be reused, by resetting the components for inserting another sensor. This reduces cost and waste, improving the environmental impact.

The telescopic sliding may refer to the plunger being slidable relative to the shaft, in particular where one component is arranged to be received within the other. The plunger may be coupled to the shaft to prevent detachment but allowing relative sliding. The plunger may be arranged within the hollow interior of the shaft. A proximal end of the plunger may be contained within the hollow interior to prevent detachment. A spring of the reset tool may also be arranged within the hollow interior. The end of the plunger within the hollow interior may engage the spring. The spring may be engaged against a top surface of the shaft, such as against a cap. In the compressed state, the plunger may extend into the hollow interior.

The channel of the applicator may refer to an opening in the outer housing of the applicator. For example, the opening may be in a top portion of the housing.

The tip portion may be part of the plunger. In other words, the plunger may comprise the tip portion. The tip portion may be an end of the plunger, for example opposite to the end contained within the shaft.

The force may be provided by a user. For example, a manual force may be applied to the reset tool (such as against a handle of the shaft) to push the reset tool in a proximal direction. As the tip portion engages the sharp carrier, the force may be translated to the sharp carrier, pushing the sharp carrier in a distal direction until it engages with the device carrier. This force may be against the spring of the applicator to reset the applicator.

The portion of the device carrier engaging the sharp carrier may comprise carrier arms engaging the sharp carrier, as described herein.

In some embodiments, the reset tool can further comprise a compressible spring housed with the hollow interior of the shaft. In some examples, the spring can bias the plunger towards a distal end of the shaft. The compressible spring may be retained between an upper surface of the shaft (such as a cap) and the plunger. A proximal force on the plunger can therefore compress the spring.

In some embodiments, the plunger is further configured to collapse within the shaft and compress the spring, and the compressed spring is configured to drive the shaft in a proximal direction.

In some embodiments, the compressed spring is configured to have a first force that is greater than a second force of a spring within the applicator. In this manner, the spring comprises a force strong enough to overcome a force of the spring within the applicator so as to allow the reset tool to be removed from the applicator.

In some embodiments, the shaft comprises a first cylindrical section and the plunger comprises a second cylindrical section, wherein a diameter of the shaft is greater than a diameter of the plunger. In this manner, the plunger is able to telescopically slide relative to the shaft and be received within the shaft. Other shapes are possible in other examples.

In some embodiments, the shaft further comprises a handle and a cap, wherein the cap is configured to cover a top portion of the handle. In this regard, the handle can provide for ergonomic use of the reset tool. In some examples, the handle can be provided without a cap, and vice versa.

In some embodiments, the tip portion of the reset tool comprises a stepped cylindrical section, wherein a diameter of the tip portion is smaller than a diameter of the plunger. In this manner, the stepped cylindrical section extends or at least partially extend into a channel of the applicator so as to interface with the sharp carrier. The stepped cylindrical section may comprise the tip portion.

In some embodiments, the applicator comprises a spring, and wherein the spring of the applicator is configured to recompress in response to the sharp carrier driving towards the device carrier of the applicator.

Disclosed herein is a reset tool for resetting an applicator for inserting an analyte sensor, the reset tool comprising a shaft comprising a hollow interior, a spring-loaded plunger configured to telescopically slide relative to the shaft, the plunger further configured to be inserted into a channel of the applicator, wherein the reset tool is configured to advance in a distal direction in response to a force, wherein the plunger is configured to compress a retraction spring of the applicator to reset the applicator. For example, the reset tool may then be used to advance the sheath, as described herein.

The applicator may be used to insert an analyte sensor, and following insertion the sharp can be retracted by a retraction spring. By compressing the retraction spring with the reset tool, the applicator can be reset to allow subsequent insertion and retraction. This allows the applicator to be reused with another sensor.

Aspects of the present disclosure can be provided in conjunction with each other and features of one aspect can be applied to other aspects. Any feature in one aspect of the present disclosure can be applied to other aspects of the present disclosure, in any appropriate combination. For instance, features of the container of the first aspect can be used in combination with features of the system of the second or third aspect. It should also be appreciated that particular combinations of the various features described and defined in any aspects of the present disclosure can be implemented and/or supplied and/or used independently.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

Embodiments of the present disclosure are described below, by way of example only, with reference to the accompanying figures.

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
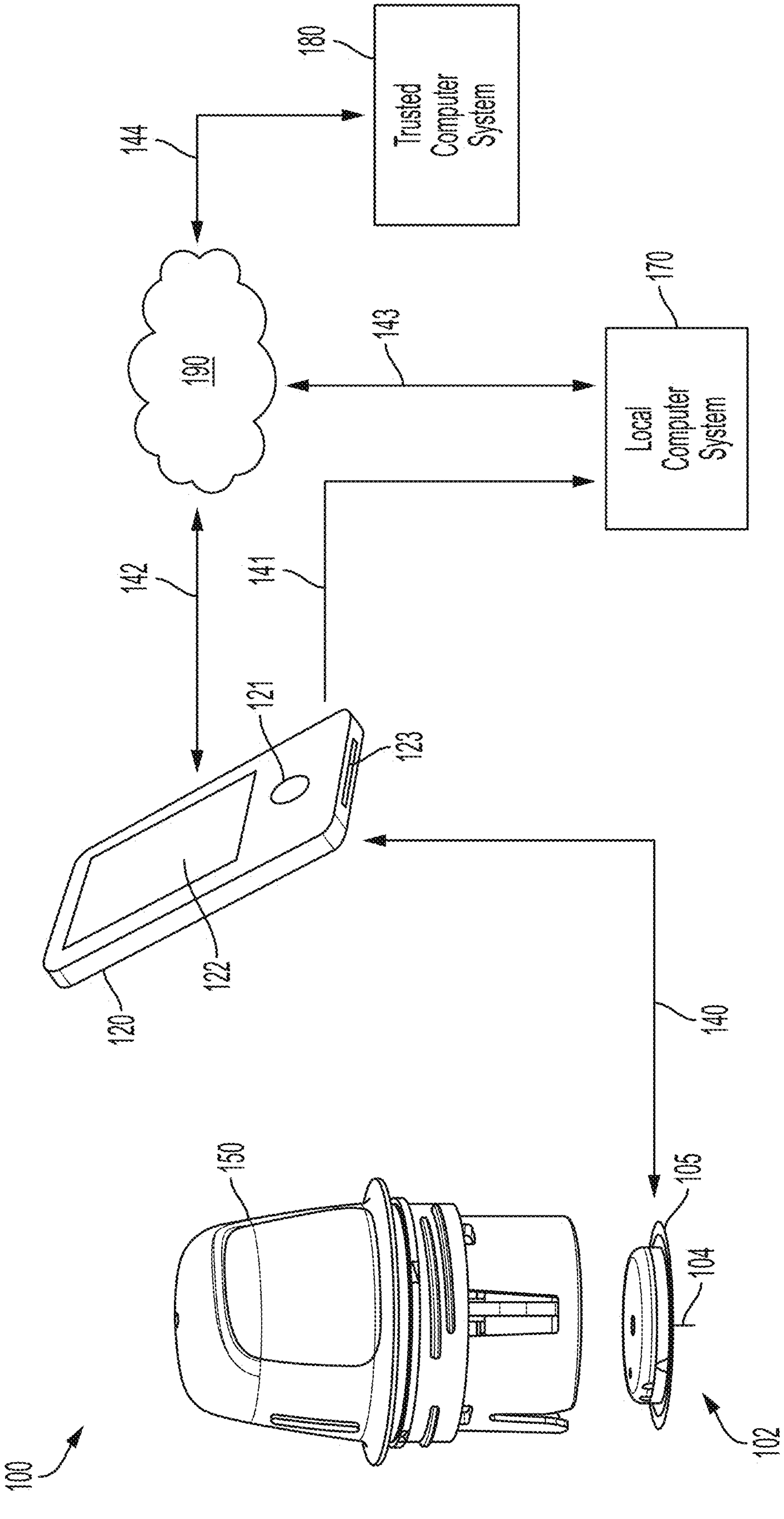
FIG. 1 is a system overview of a sensor applicator, reader device, monitoring system, network, and remote system.

Before the present disclosure is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer's bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for improved sensor insertion devices for use with in vivo analyte monitoring systems. Many embodiments of the present disclosure are designed to: improve the method of sensor insertion with respect to in vivo analyte monitoring systems, minimize trauma to an insertion site during a sensor insertion process, and reduce overall interference with sensor performance. These embodiments allow for a smaller skin penetration and, thus, create a smaller wound with less trauma at the insertion site, which can reduce the chance of early signal attenuation ("ESA"). Overall, these embodiments can improve the likelihood of a successful sensor insertion and reduce the amount of trauma at the insertion site, to name a few advantages.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein.

The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Exemplary In Vivo Analyte Monitoring System

FIG. 1 is a conceptual diagram depicting an example embodiment of an analyte monitoring system 100 that includes a sensor applicator 150, a sensor control device 102, and a reader device 120. Sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy, Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Exemplary Reader Device

Figure 2A:
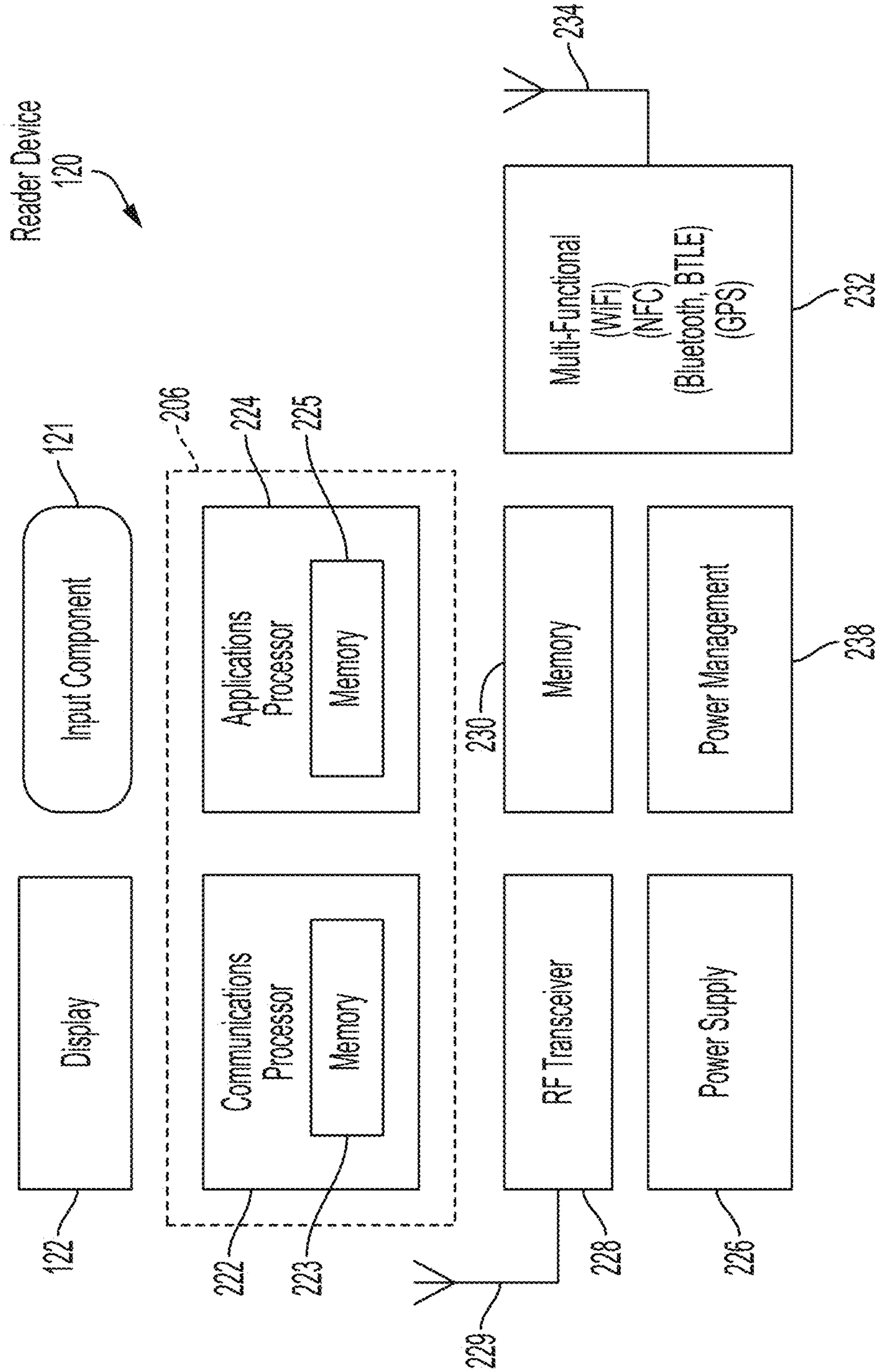
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multi-functional transceiver 232 which can communicate over Wi-Fi, NFC, Bluetooth, BTLE, and GPS with an antenna 234. As understood by one of skill in the art, these components are electrically and communicatively coupled in a manner to make a functional device.

Exemplary Sensor Control Devices

Figure 2B:
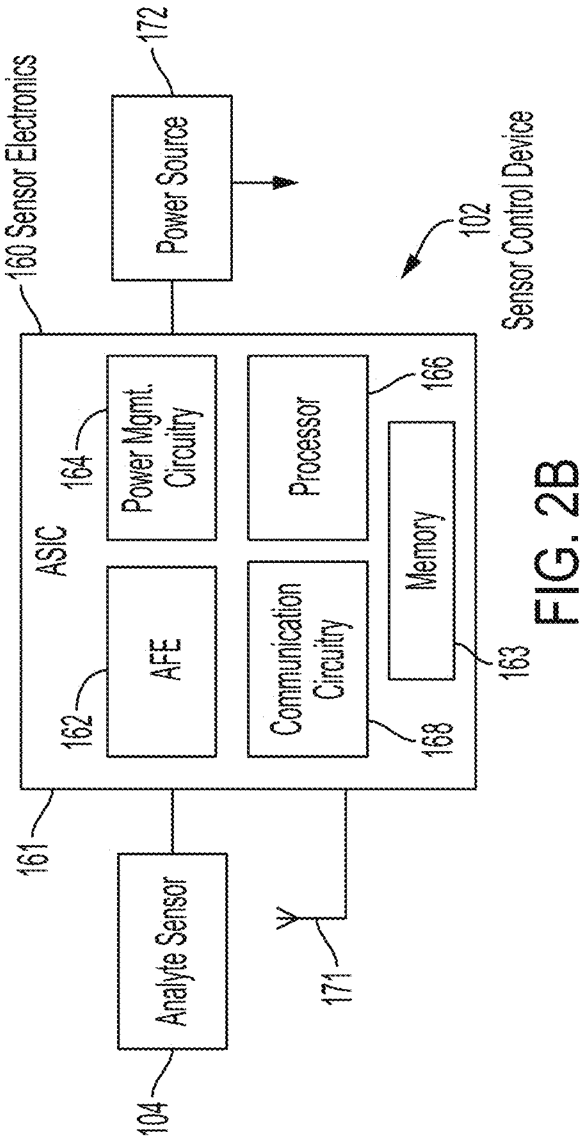
FIGS. 2B and 2C are block diagrams depicting example embodiments of sensor control devices.
Figure 2C:
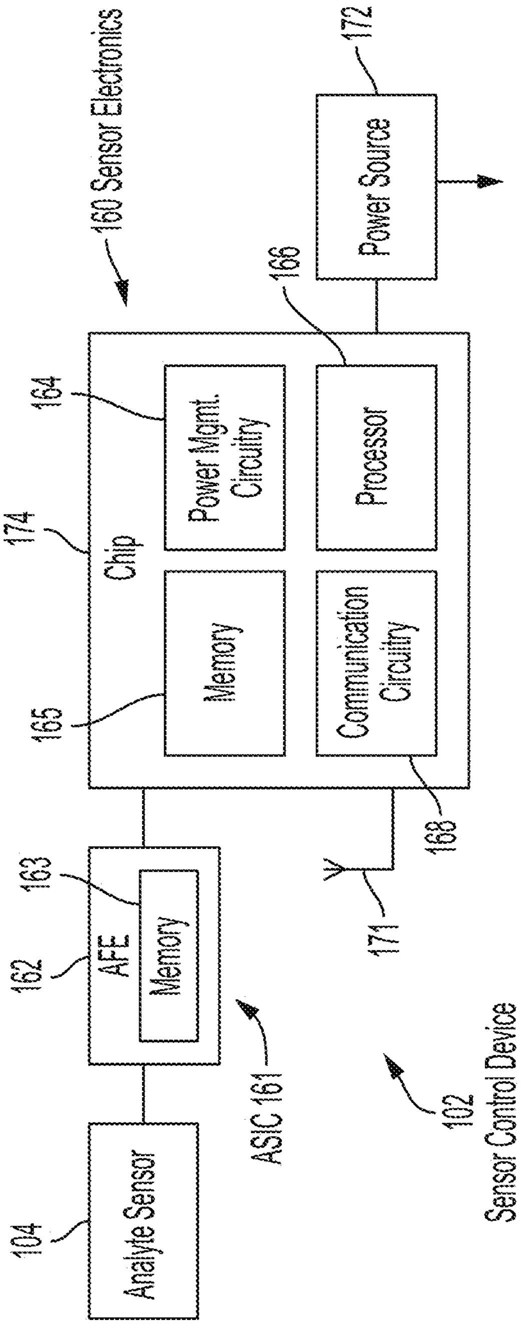

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 172, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiment of Sensor Applicator Device

Figure 3C:
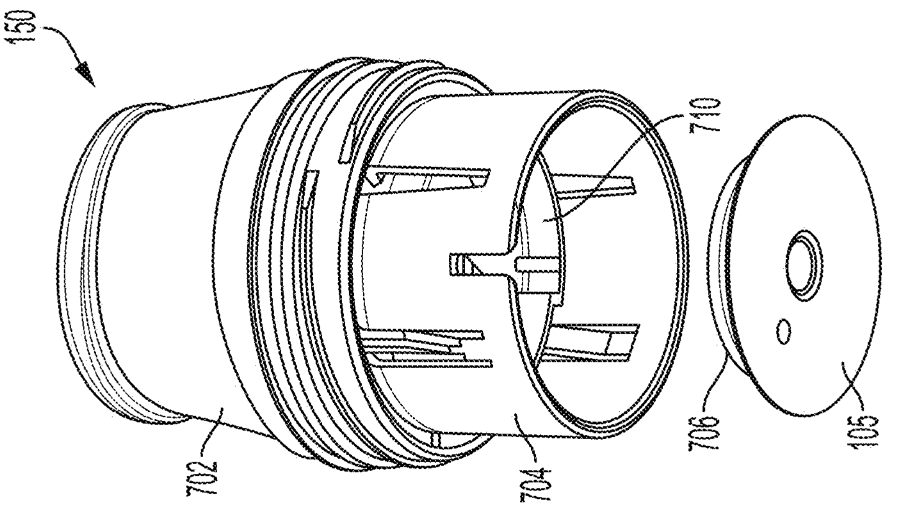
FIG. 3C is a perspective view depicting an example embodiment of a distal end of an applicator device and electronics housing.
Figure 3B:
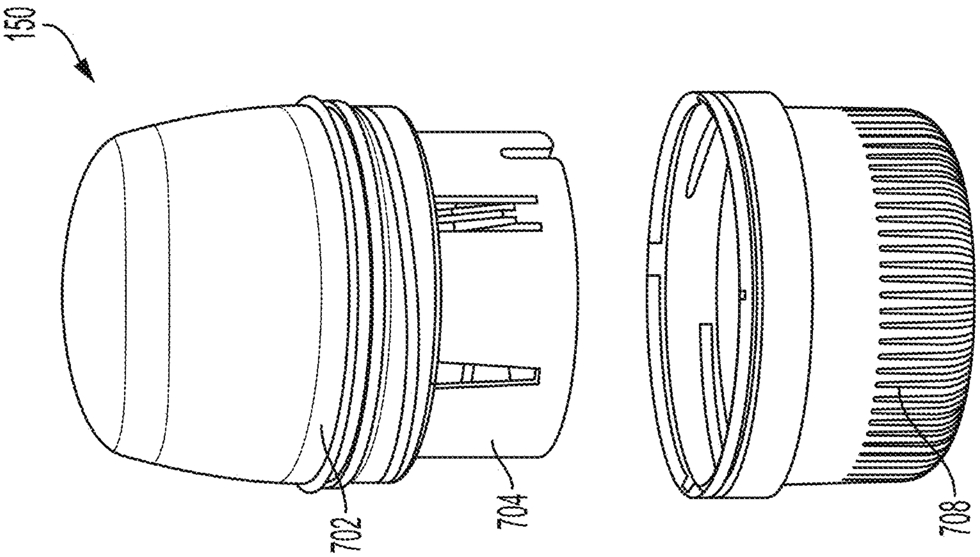
FIG. 3B is a side perspective view depicting an example embodiment of an applicator device and cap decoupled.
Figure 3A:
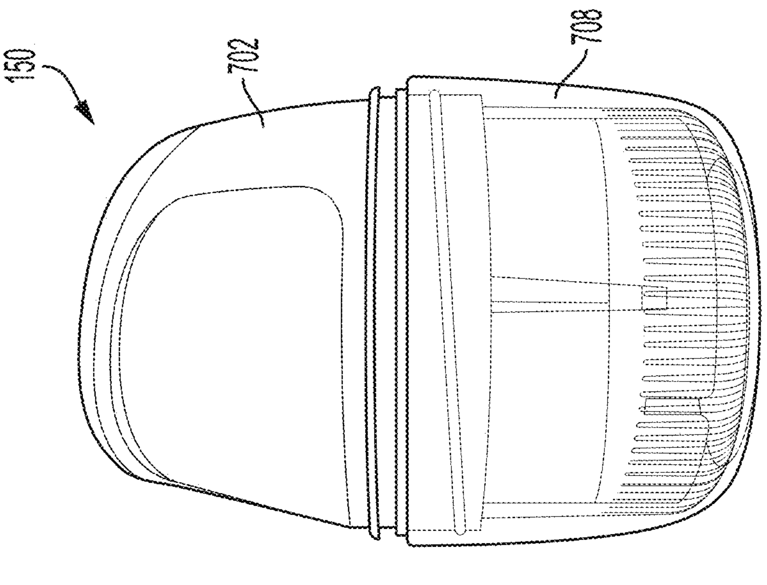
FIG. 3A is a side view depicting an example embodiment of an applicator device coupled with a cap.

FIG. 3A is a side view depicting an example embodiment of an applicator device 150 coupled with screw cap 708. This is one example of how applicator 150 is shipped to and received by a user, prior to assembly by the user with a sensor. In other embodiments, applicator 150 can be shipped to the user with the sensor and sharp contained therein. FIG. 3B is a side perspective view depicting applicator 150 and cap 708 after being decoupled. FIG. 3C is a perspective view depicting an example embodiment of a distal end of an applicator device 150 with electronics housing 706 and adhesive patch 105 removed from the position they would have retained within device carrier 710 of sheath 704, when cap 708 is in place.

Example Embodiment of Applicator Housing

Figure 4A:
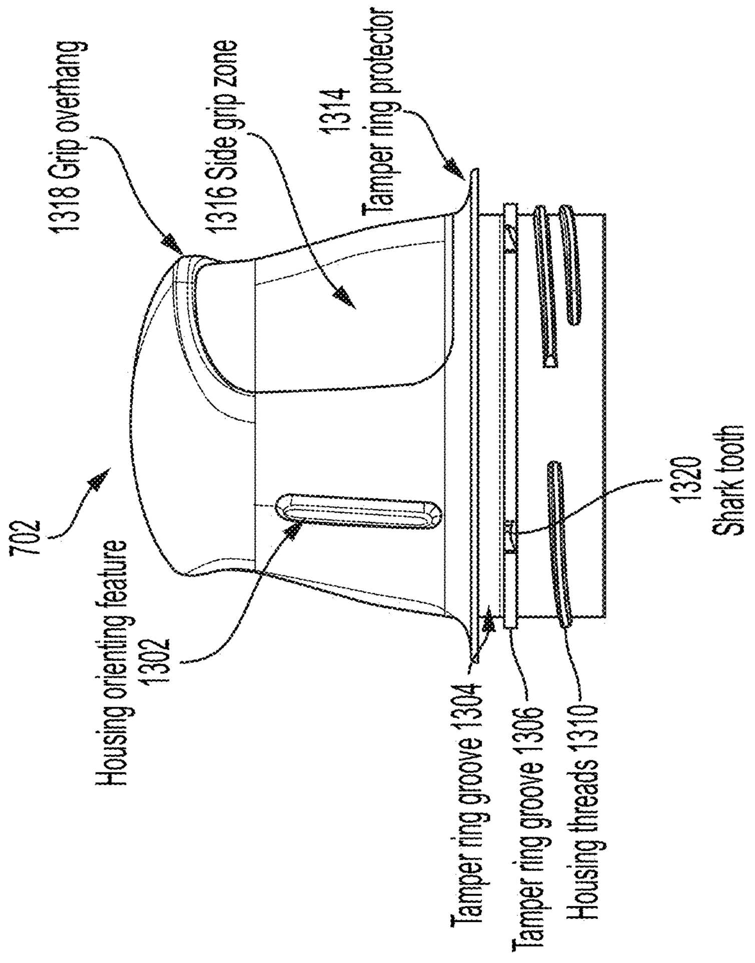
FIG. 4A is side view depicting an example embodiment of a housing.

FIG. 4A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 3A and 3B) by aligning with complimentary cap threads and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in case of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 4B:
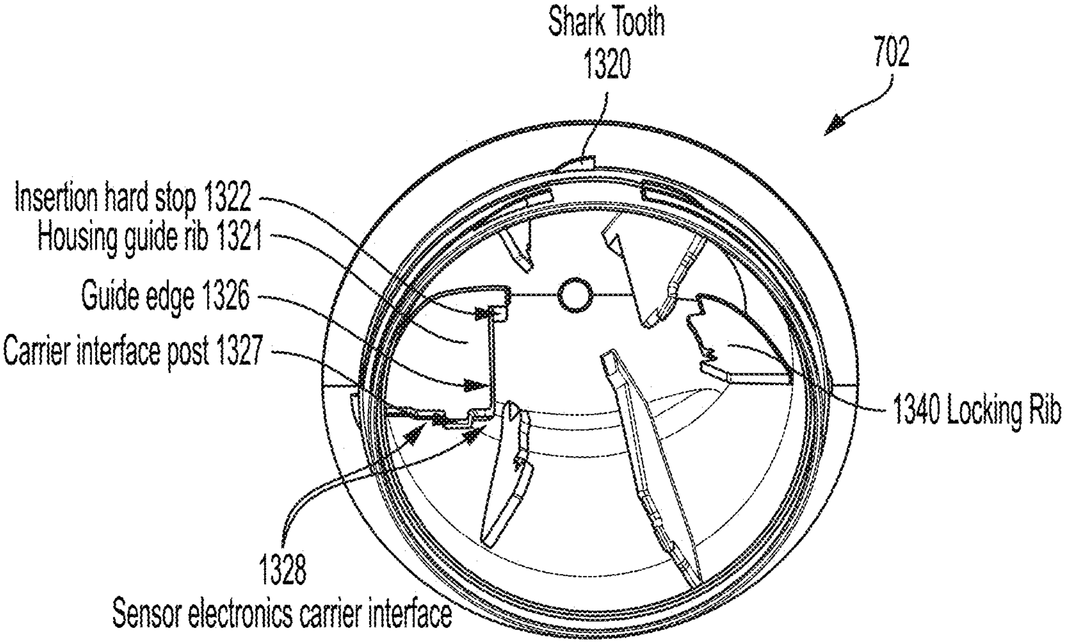
FIG. 4B is a perspective view depicting an example embodiment of a distal end of a housing.
Figure 4C:
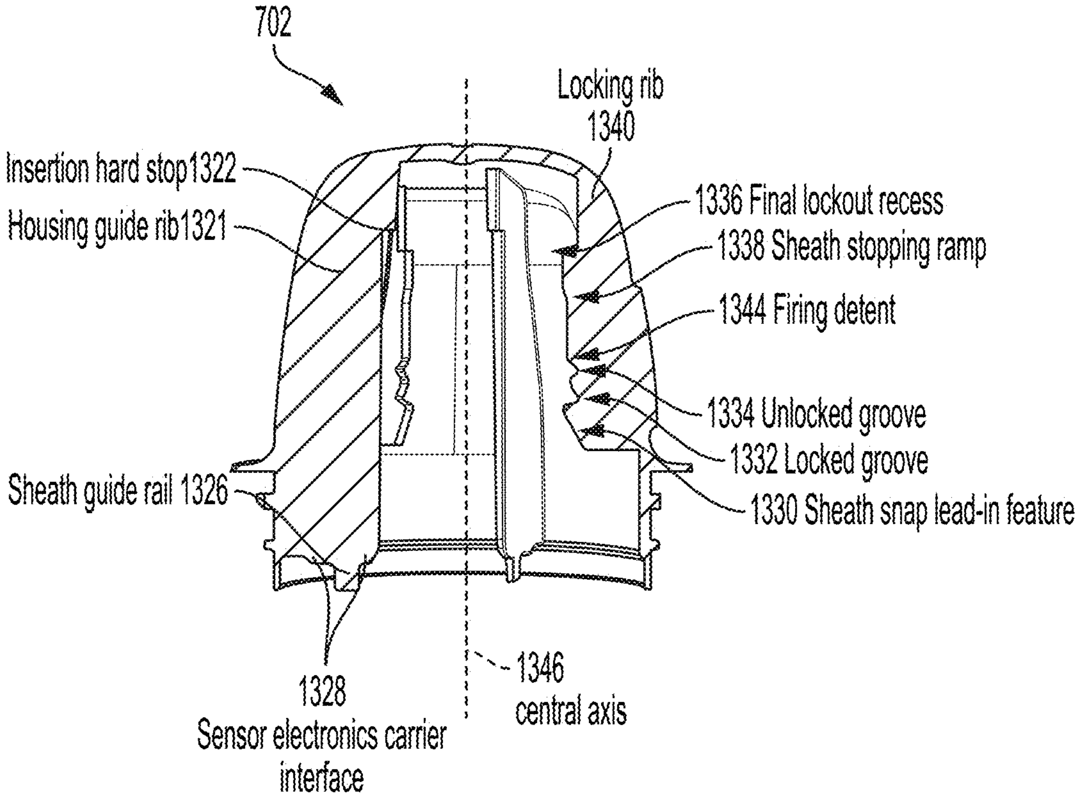
FIG. 4C is a side cross-sectional view depicting an example embodiment of a housing.

FIG. 4B is a perspective view depicting a distal end of housing 702. Here, three housing guide structures (or "guide ribs") 1321 are located at 120 degree angles with respect to each other, and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 5A). An insertion hard stop 1322 can be a flat, distally facing surface of housing guide rib 1321 located near a proximal end of housing guide rib 1321. Insertion hard stop 1322 provides a surface for a device carrier travel limiter face 1420 of a sheath 704 (FIG. 5B) to abut during use, preventing device carrier travel limiter face 1420 from moving any further in a proximal direction. A carrier interface post 1327 passes through an aperture 1510 (FIG. 6A) of device carrier 710 during an assembly. A device carrier interface 1328 can be a rounded, distally facing surface of housing guide ribs 1321 which interfaces with device carrier 710.

FIG. 4A is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 5C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 5C.

As housing 702 moves further in a proximal direction toward the skin surface, and as sheath 704 advances toward the distal end of housing 702, detent snaps 1402 shift into the unlocked grooves 1334, and applicator 150 is in an "armed" position, ready for use. When the user further applies force to the proximal end of housing 702, while sheath 704 is pressed against the skin, detent snap 1402 passes over firing detent 1344. This begins a firing sequence due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging device carrier travel limiter face 1420.

Example Embodiment of Applicator Sheath

Figure 5A:
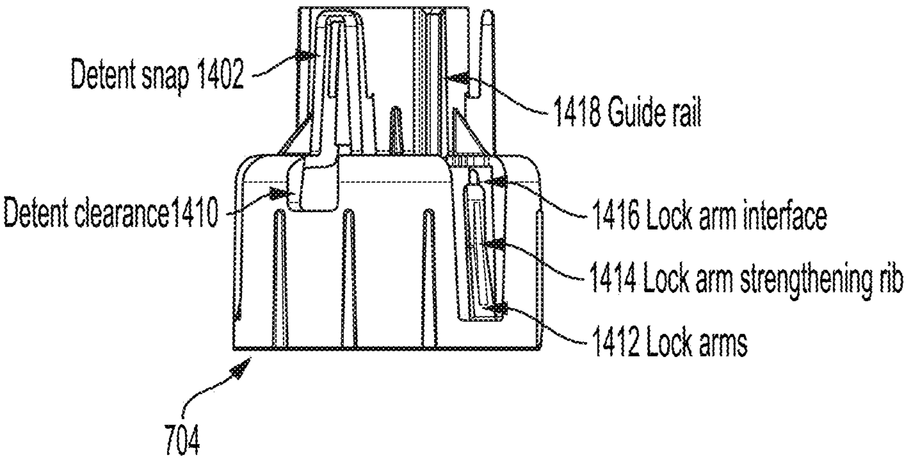
FIG. 5A is a side view depicting an example embodiment of a sheath.
Figure 5B:
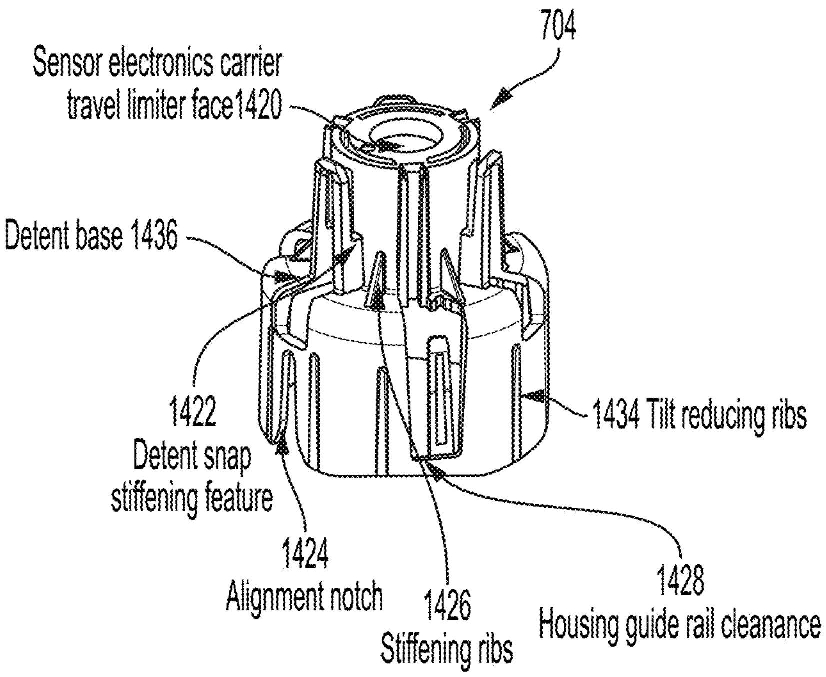
FIG. 5B is a perspective view depicting an example embodiment of a proximal end of a sheath.

FIGS. 5A and 5B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 5C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between device carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock device carrier 710 to sheath 704 when lock arm interface 1416 of lock arms 1412 engage lock interface 1502 of device carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 5C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

Figure 5D:
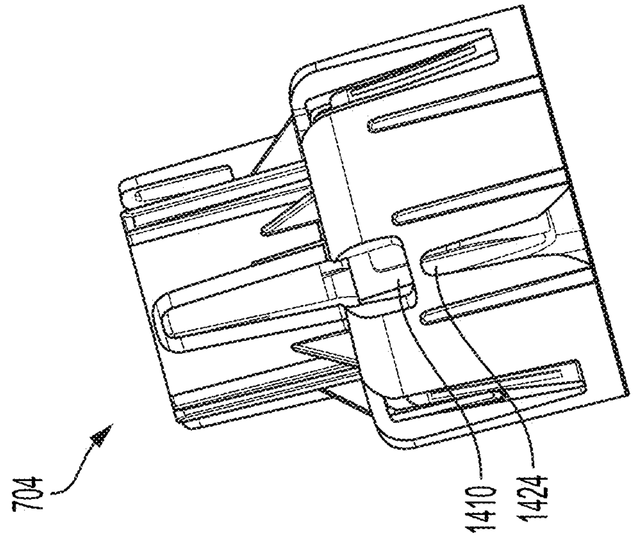
FIG. 5D is a side view depicting an example embodiment of features of a sheath.
Figure 5C:
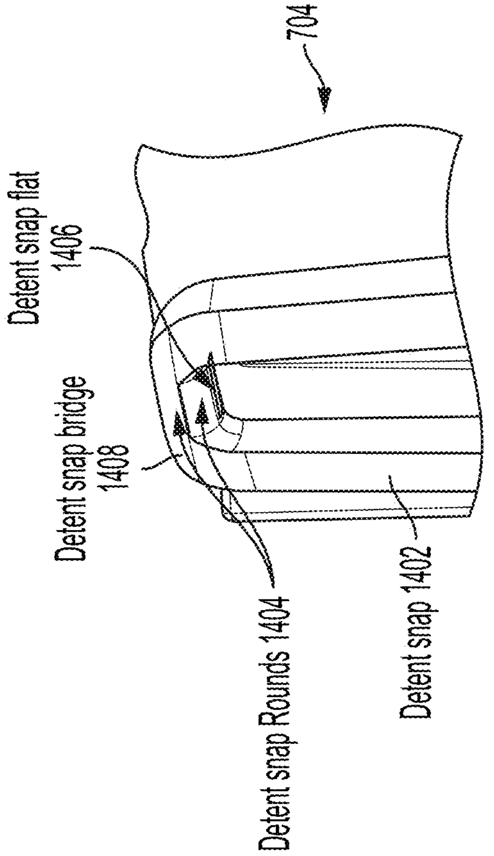
FIG. 5C is a close-up perspective view depicting an example embodiment of a distal side of a detent snap of a sheath.

FIG. 5D is a side view depicting an example embodiment of sheath 704. Here, alignment notch 1424 can be relatively close to detent clearance 1410. Detent clearance 1410 is in a relatively proximal location on distal portion of sheath 704.

Figure 5E:
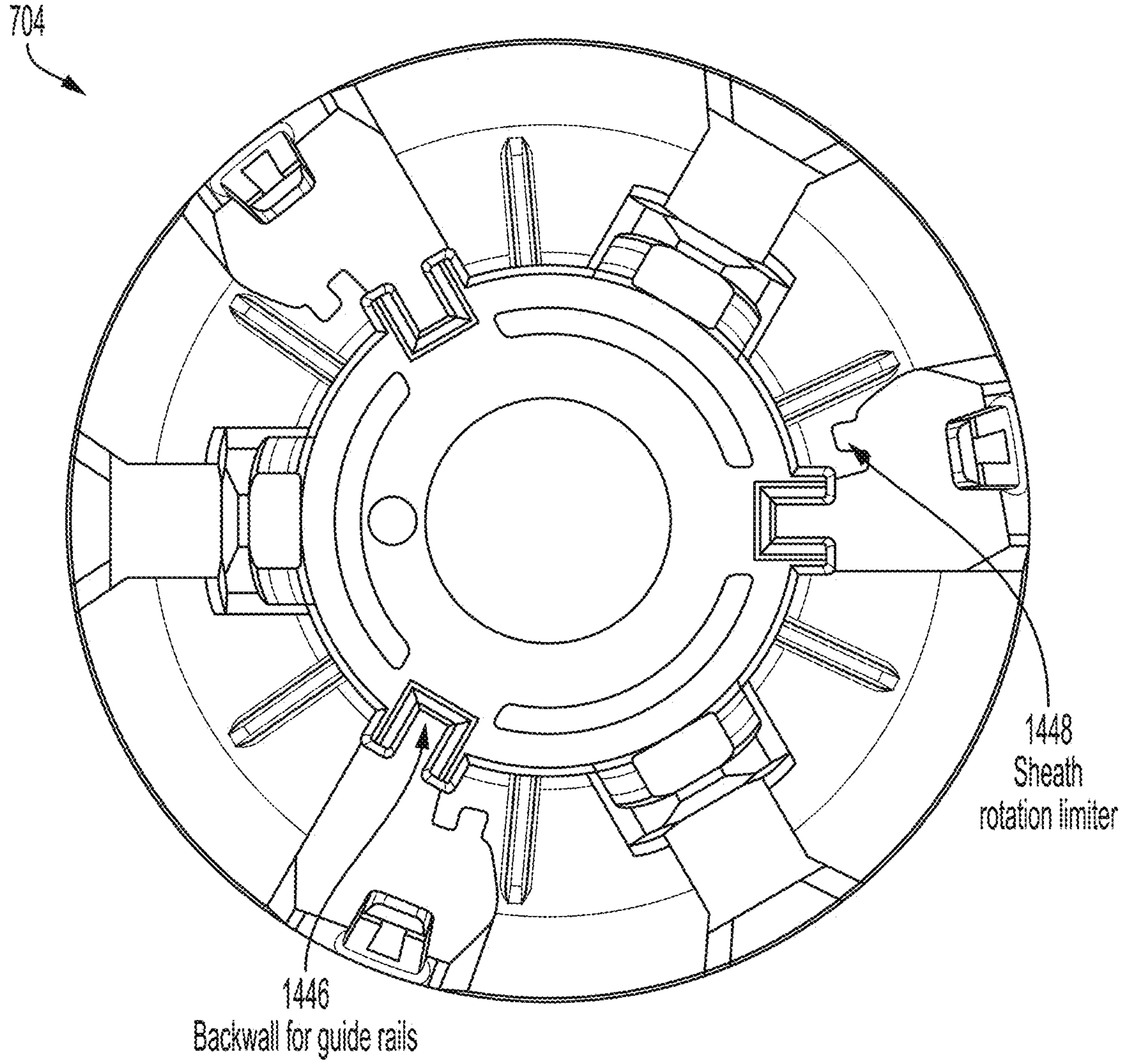
FIG. 5E is an end view of an example embodiment of a proximal end of a sheath.

FIG. 5E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704. In a general sense, the embodiments described herein operate by flattening and stretching a skin surface at a predetermined site for sensor insertion. Moreover, the embodiments described herein can also be utilized for other medical applications, such as, e.g., transdermal drug delivery, needle injection, wound closure stitches, device implantation, the application of an adhesive surface to the skin, and other like applications.

By way of background, those of skill the art will appreciate that skin is a highly anisotropic tissue from a biomechanical standpoint and varies largely between individuals. This can affect the degree to which communication between the underlying tissue and the surrounding environment can be performed, e.g., with respect to drug diffusion rates, the ability to penetrate skin with a sharp, or sensor insertion into the body at a sharp-guided insertion site.

Example Embodiments of Device Carriers

Figure 6A:
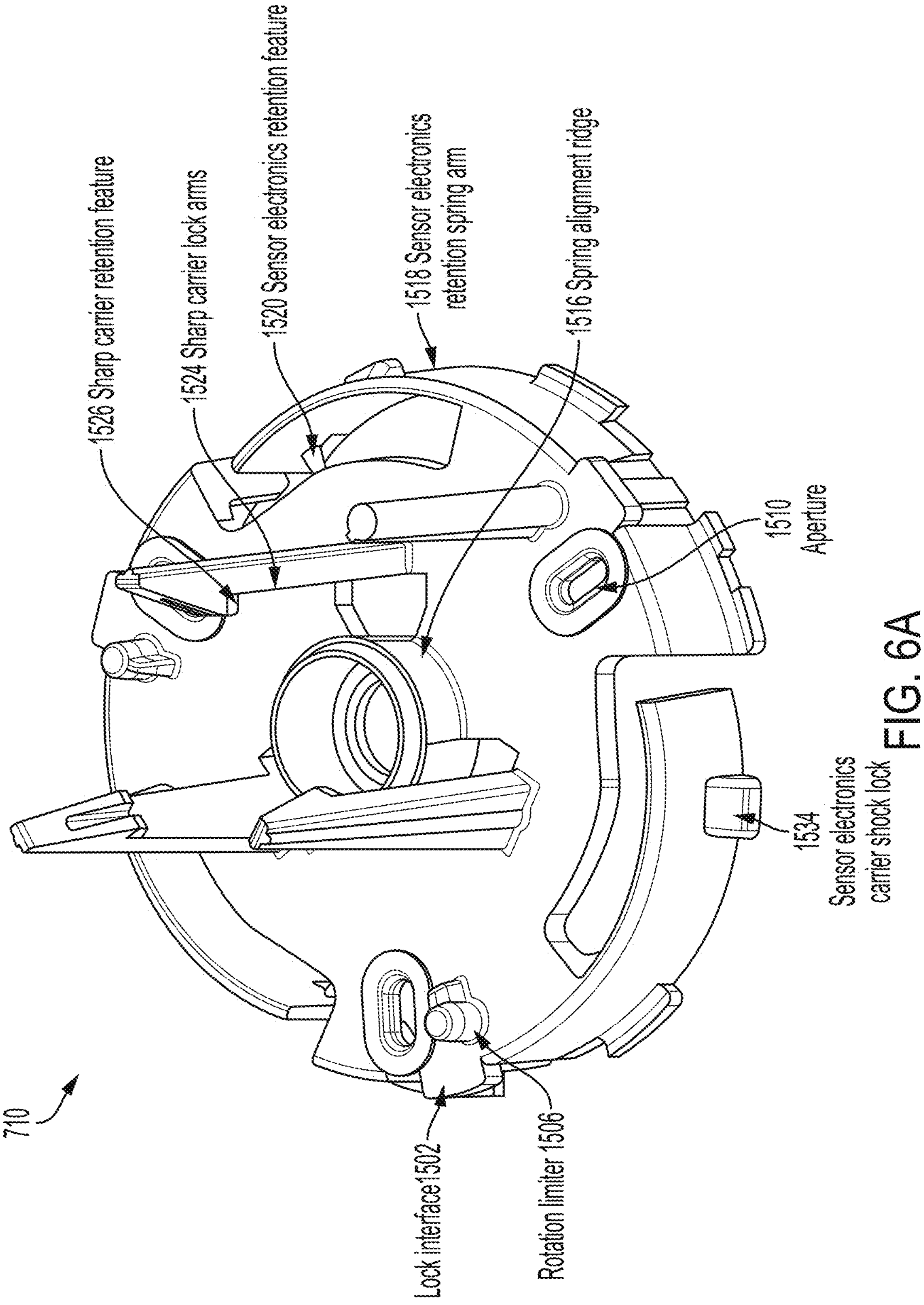
FIG. 6A is a proximal perspective view depicting an example embodiment of a device carrier.

FIG. 6A is a proximal perspective view depicting an example embodiment of device carrier 710 that can retain sensor electronics within applicator 150. It can also retain sharp carrier 1102 with sharp module 2500. In this example embodiment, device carrier 710 generally has a hollow round flat cylindrical shape, and can include one or more deflectable sharp carrier lock arms 1524 (e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of device carrier 710 extending outward and can lock device carrier 710 for added safety prior to firing. Rotation limiter 1506 can be a proximally extending relatively short protrusion on a proximal surface of device carrier 710 which limits rotation of carrier 710. Sharp carrier lock arms 1524 can interface with sharp carrier 1102 as described with reference to FIGS. 7 and 8 below.

Figure 6B:
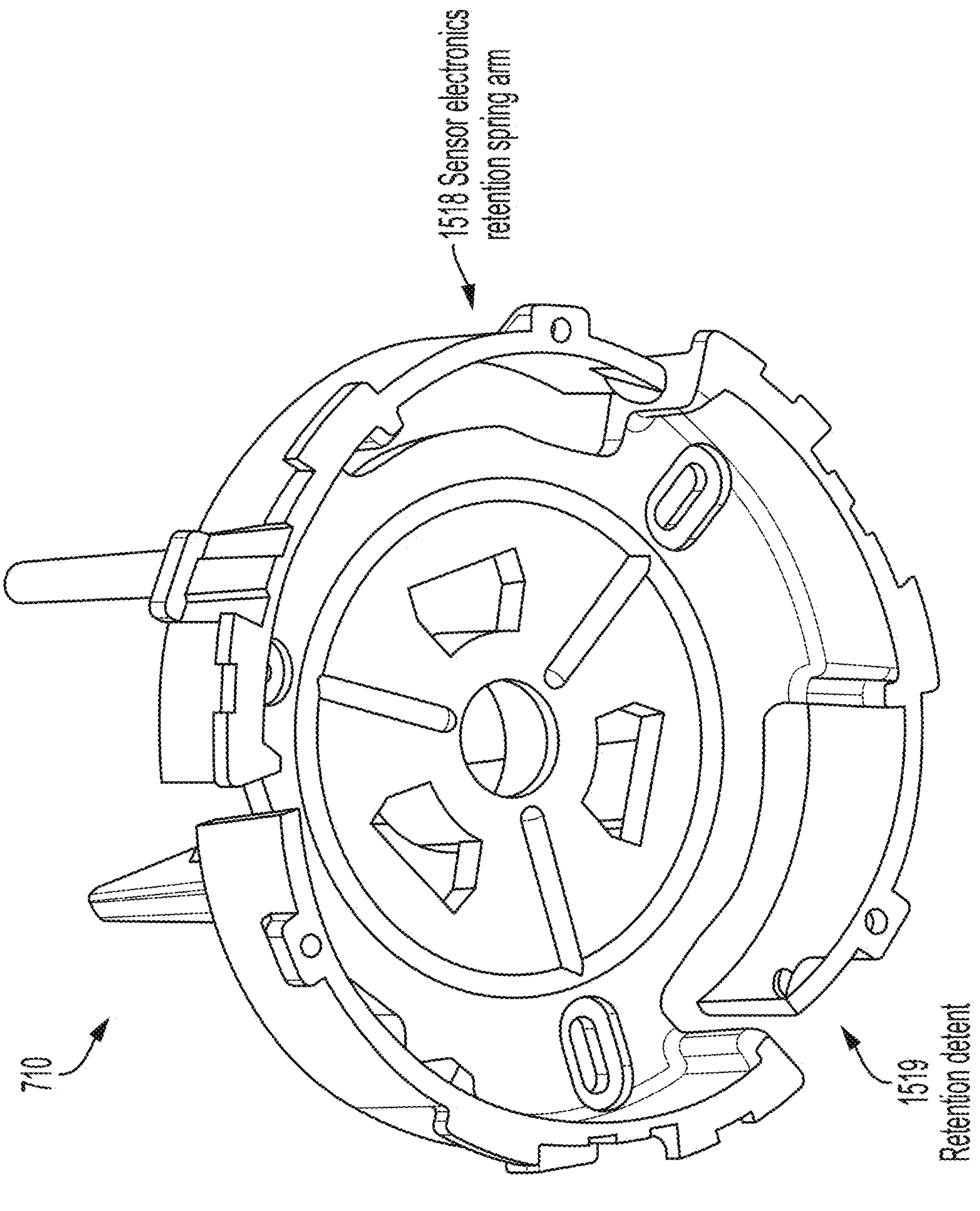
FIG. 6B is a distal perspective view depicting an example embodiment of a device carrier.

FIG. 6B is a distal perspective view of device carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Example Embodiments of Sharp Carriers

Figure 7:
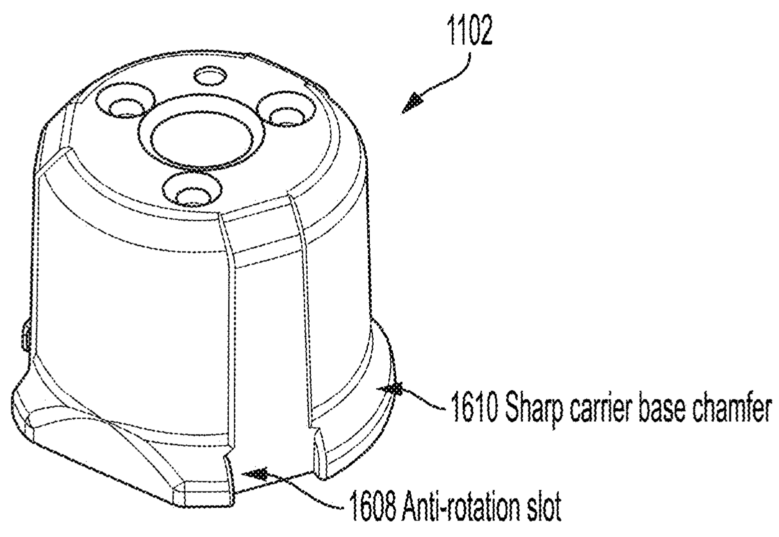
FIG. 7 is a proximal perspective view of an example embodiment of a sharp carrier.
Figure 8:
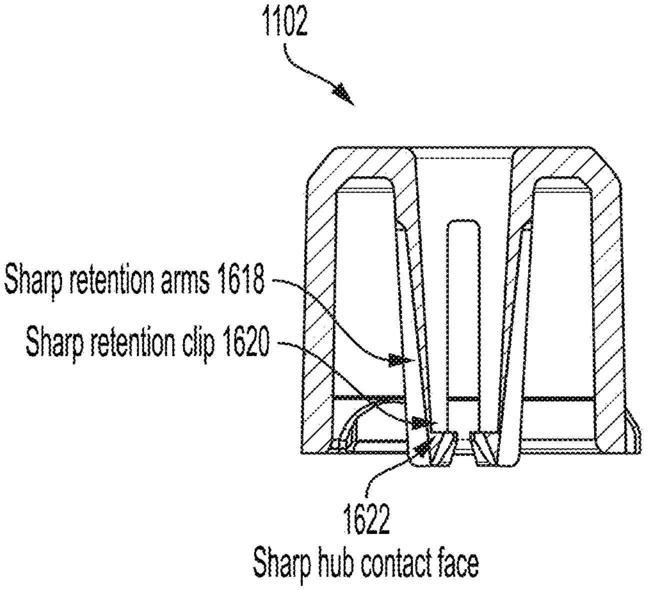
FIG. 8 is a side cross-sectional view depicting an example embodiment of a sharp carrier.

FIGS. 7 and 8 are a proximal perspective view and a side cross-sectional view, respectively, depicting an example embodiment of sharp carrier 1102. Sharp carrier 1102 can grasp and retain sharp module 2500 within applicator 150. Near a distal end of sharp carrier 1102 can be anti-rotation slots 1608 which prevent sharp carrier 1102 from rotating when located within a central area of sharp carrier lock arms 1524 (as shown in FIG. 6A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

As shown in FIG. 8, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub.

Exemplary Sensor Modules

Figure 9A:
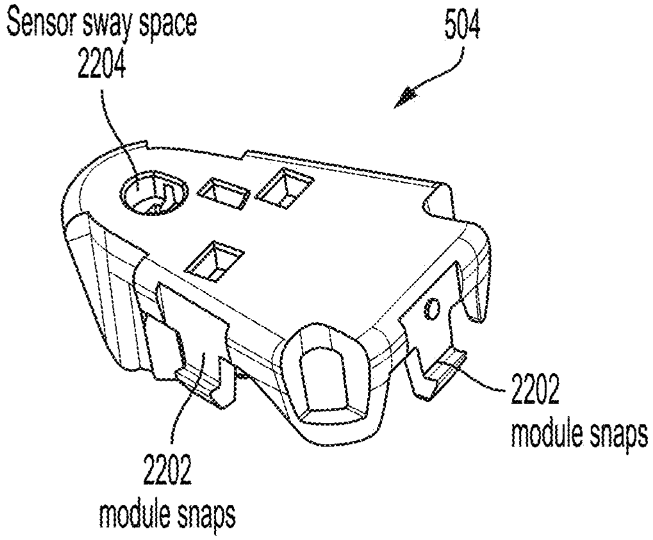
FIGS. 9A to 9B are top and bottom perspective views, respectively, depicting an example embodiment of a sensor module.
Figure 9B:
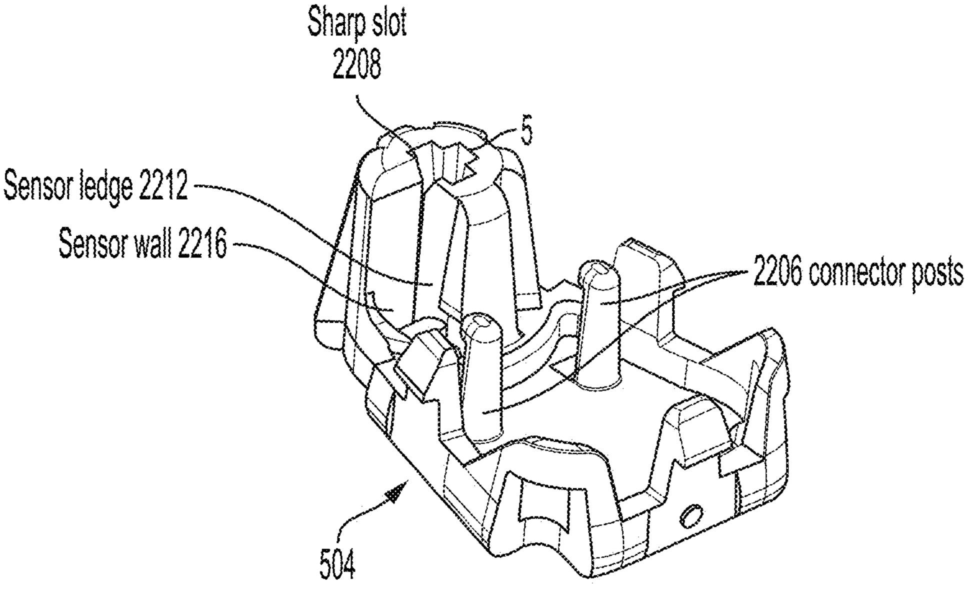

FIGS. 9A and 9B are a top perspective view and a bottom perspective view, respectively, depicting an example embodiment of sensor module 504. Module 504 can hold a connector 2300 (FIGS. 10A and 10B) and a sensor 104 (FIG. 11A). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figure 10A:
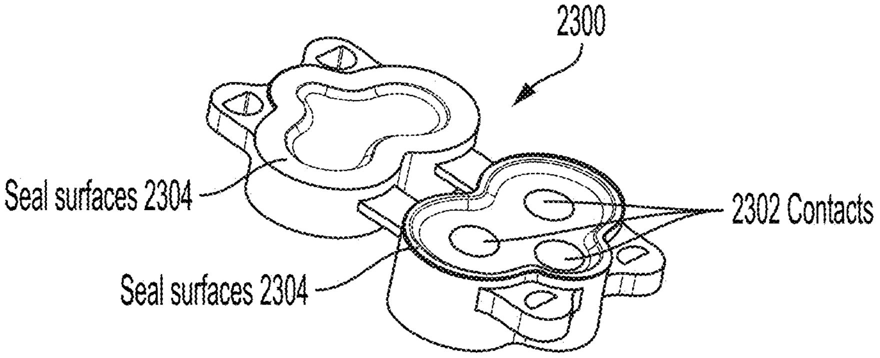
FIGS. 10A and 10B are perspective and compressed views, respectively, depicting an example embodiment of a sensor connector.
Figure 10B:
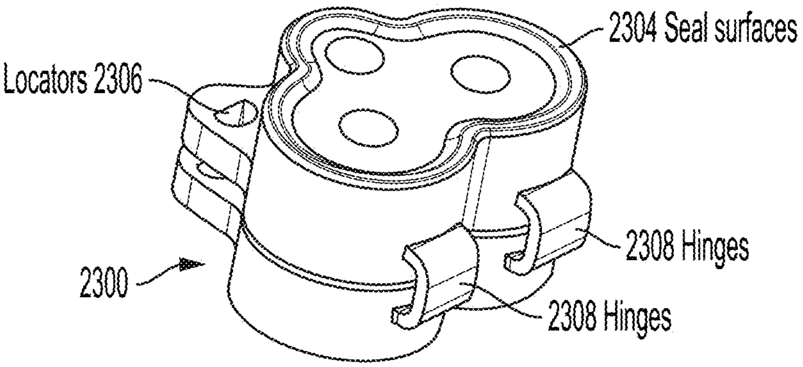
Figure 11A:
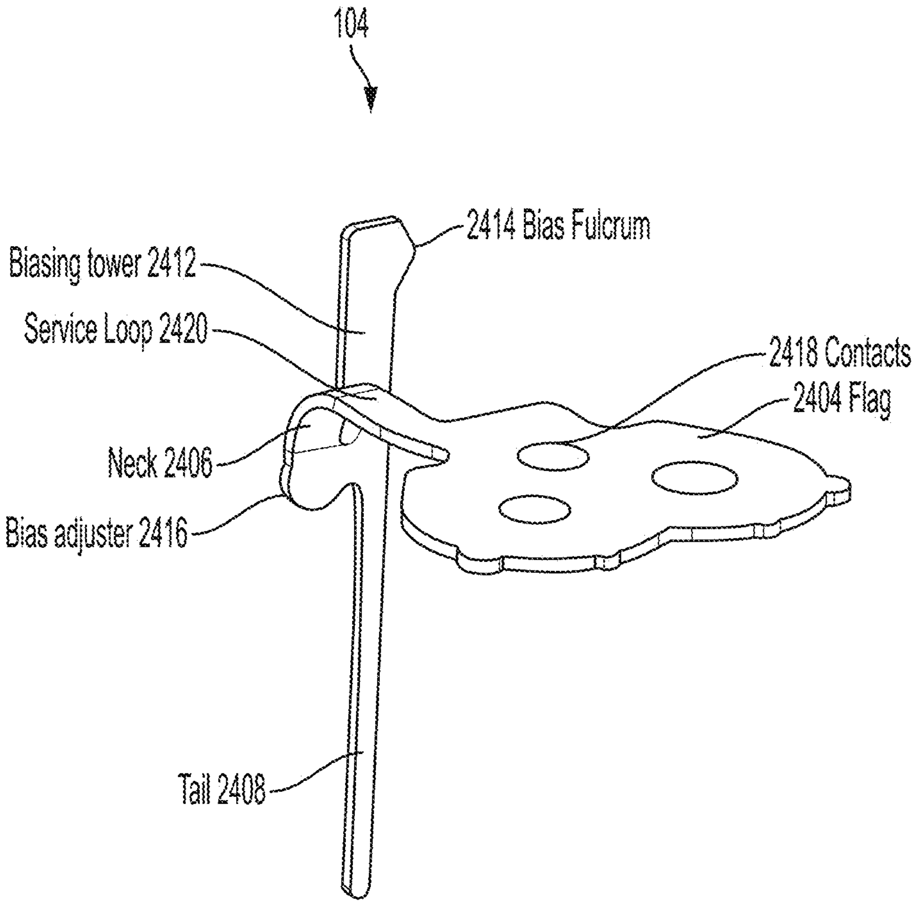
FIG. 11A is a perspective view depicting an example embodiment of a sensor.

FIGS. 10A and 10B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2208 can connect two distal and proximal portions of connector 2300.

FIG. 11A is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 9B).

Figure 11B:
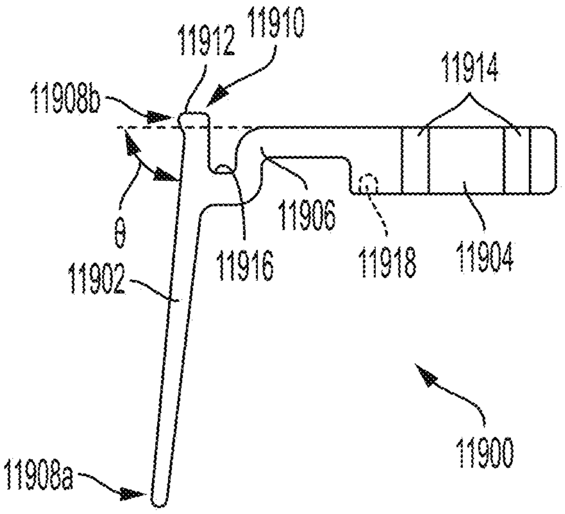
FIG. 11B is a side view of an example embodiment of a sensor.

FIG. 11B is a side view of an example sensor 11900, according to one or more embodiments of the disclosure. The sensor 11900 can be similar in some respects to any of the sensors described herein and, therefore, can be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane can cover the chemistry. In use, the tail 11902 is transcutaneously received beneath a user's skin, and the chemistry included thereon helps facilitate analyte monitoring in the presence of bodily fluids.

The tail 11902 can be received within a hollow or recessed portion of a sharp (not shown) to at least partially circumscribe the tail 11902 of the sensor 11900. As illustrated, the tail 11902 can extend at an angle Q offset from horizontal. In some embodiments, the angle Q can be about 85°. Accordingly, in contrast to other sensor tails, the tail 11902 may not extend perpendicularly from the flag 11904, but instead at an angle offset from perpendicular. This can prove advantageous in helping maintain the tail 11902 within the recessed portion of the sharp.

The tail 11902 includes a first or bottom end **11908*a* and a second or top end 11908*b* opposite the bottom end 11908*a*. A tower 11910 can be provided at or near the top end 11908*b* and can extend vertically upward from the location where the neck 11906 interconnects the tail 11902 to the flag 11904. During operation, if the sharp moves laterally, the tower 11910 will help pivot the tail 11902 toward the sharp and otherwise stay within the recessed portion of the sharp. Moreover, in some embodiments, the tower 11910 can provide or otherwise define a protrusion 11912 that extends laterally therefrom. When the sensor 11900 is mated with the sharp and the tail 11902 extends within the recessed portion of the sharp, the protrusion 11912 can engage the inner surface of the recessed portion. In operation, the protrusion 11912 can help keep the tail 11902** within the recessed portion.

The flag 11904 can comprise a generally planar surface having one or more sensor contacts 11914 arranged thereon. The sensor contact(s) 11914 can be configured to align with a corresponding number of compliant carbon impregnated polymer modules encapsulated within a connector.

In some embodiments, as illustrated, the neck 11906 can provide or otherwise define a dip or bend 11916 extending between the flag 11904 and the tail 11902. The bend 11916 can prove advantageous in adding flexibility to the sensor 11900 and helping prevent bending of the neck 11906.

In some embodiments, a notch 11918 (shown in dashed lines) can optionally be defined in the flag near the neck 11906. The notch 11918 can add flexibility and tolerance to the sensor 11900 as the sensor 11900 is mounted to the mount. More specifically, the notch 11918 can help take up interference forces that can occur as the sensor 11900 is mounted within the mount.

Figure 11C:
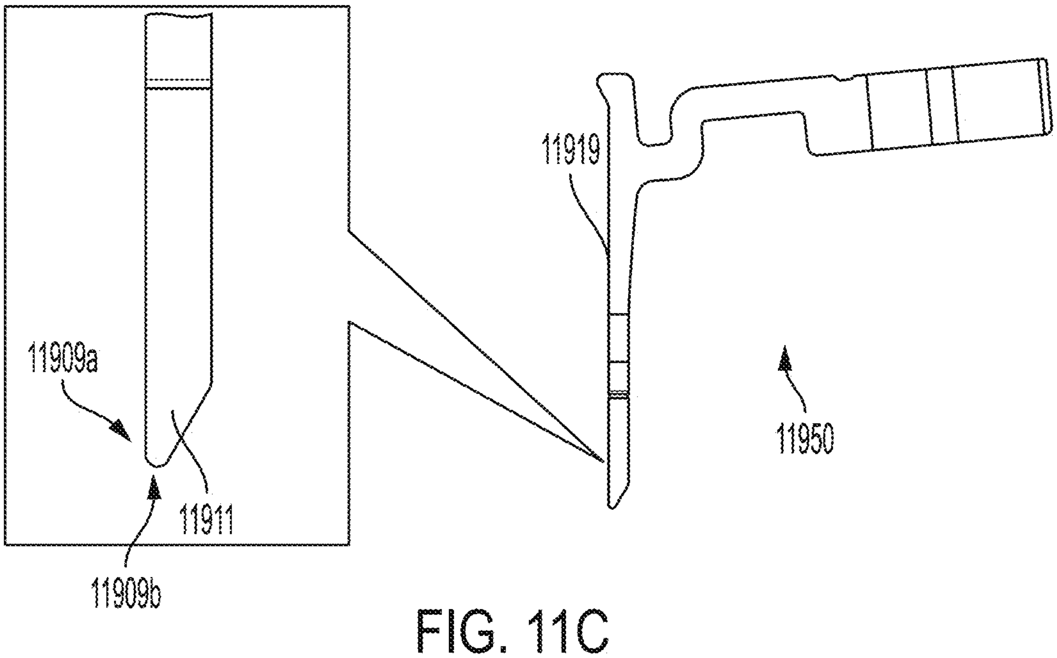
FIG. 11C is a side view of example embodiment of a sensor and a callout view of a tip portion thereof.

FIG. 11C illustrates one embodiment of a sensor 11950 including a modified tail 11919. In some embodiments, the first or bottom end **11909*a* is chiseled or tapered so as to form a bottom end 11909*a* having one or more beveled edges. In some embodiments, the bottom end 11909*a* comprises a single beveled edge 11911. More specifically, the sensor tail 11919 comprises a bottom end 11909*a* which forms a tip portion 11909*b* having a sharpened, V-shaped vertex. This sensor design can be advantageous in that reduces the overall footprint of the sensor 11950, and minimizes the size of skin penetration and puncture wound as it dilates the tissue during sensor insertion. Consequently, the risk of ESA created by wound trauma can be mitigated by the sensor's 11950 bottom end 11909*a* having a V-shaped tip portion 11909*b*** with a sharpened vertex.

Generally, the sensor can be understood as including a tail, a flag, and a neck aligned along a planar surface having a vertical axis and a horizontal axis. The spring-like structure can be created by various orientations of turns in the bend of the neck of a sensor. Between the tail and the flag, the neck can include at least two turns in relation to the vertical axis providing a spring-like structure. The at least two turns can provide, in relation to an axis of the planar surface shared by the tail, the flag, and the neck, overlapping layers of the structure of the neck, where the neck itself remains unbroken. These overlapping turns make up the spring-like structure. In some embodiments, the overlapping layers of the neck are vertically-oriented. In some embodiments, the overlapping layers of the neck are horizontally-oriented.

The turns of the neck can be created by folding the neck of the sensor from a larger neck structure, laser cutting the sensor from a sheet of the material comprising the sensor, printing the sensor having the configuration with turns, stamping the sensor from a sheet of material of which the sensor is composed, or other suitable manufacturing processes for providing precision bends in the neck.

Example Embodiments of Sharp Modules

Figure 12A:
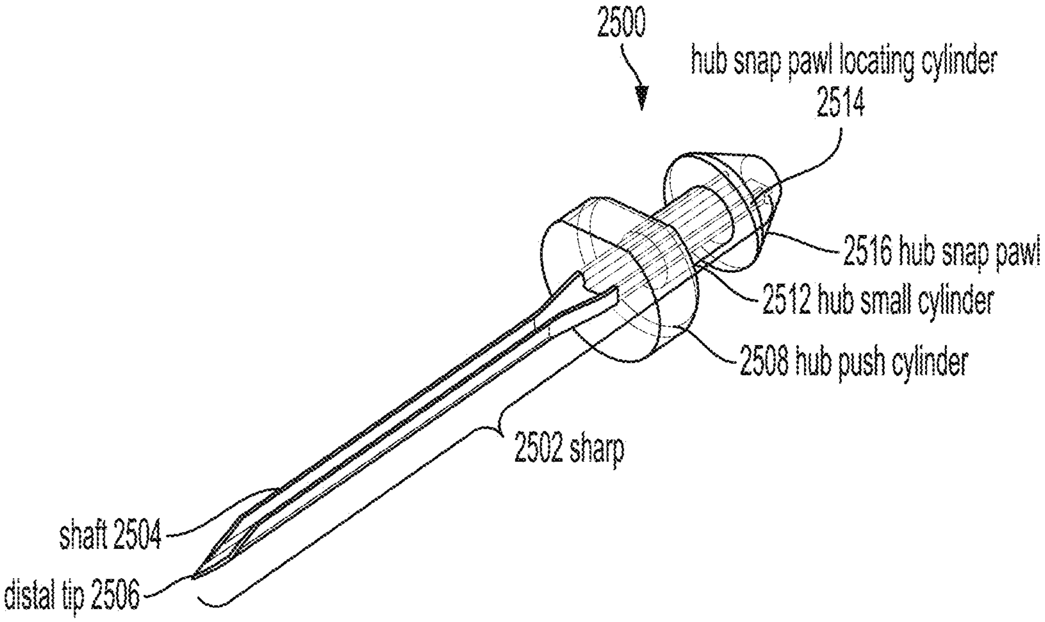
FIG. 12A is a perspective view depicting an example embodiment of a sharp module.

FIG. 12A is a perspective view depicting an example embodiment of sharp module 2500 prior to assembly within sensor module 504 (FIGS. 9A and 9B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 8). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500. Further details regarding embodiments of sharp modules, sharps, their components, and variants thereof, are described in U.S. Patent Publication No. 2014/0171771, which is incorporated by reference herein in its entirety and for all purposes.

Figure 12B:
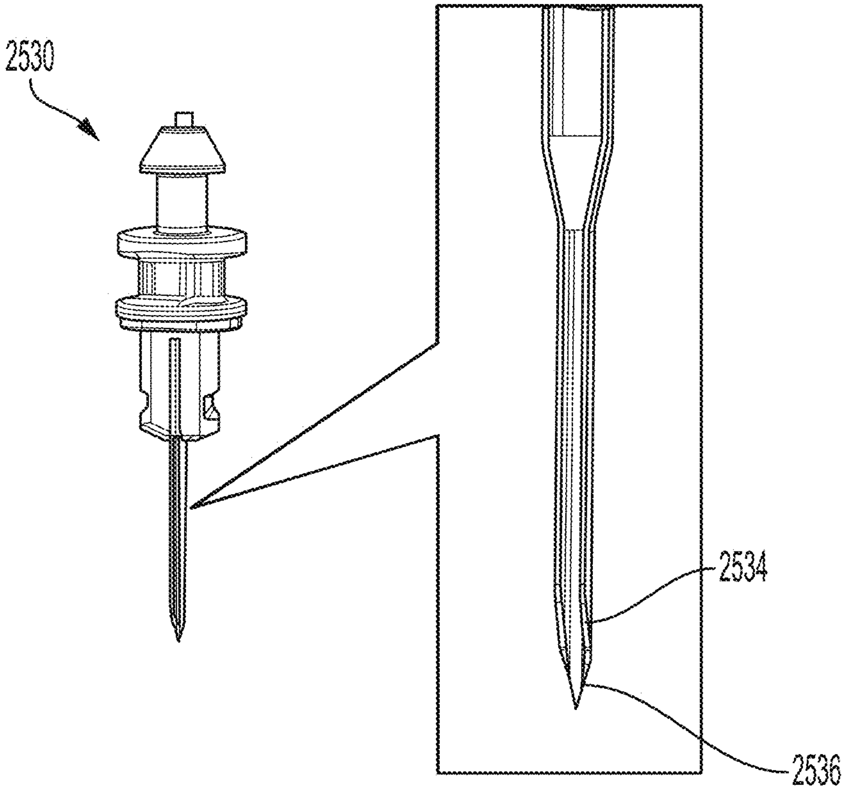
FIG. 12B is a perspective view depicting an example embodiment of a sharp module, and a callout view of the distal tip thereof.
Figure 12C:
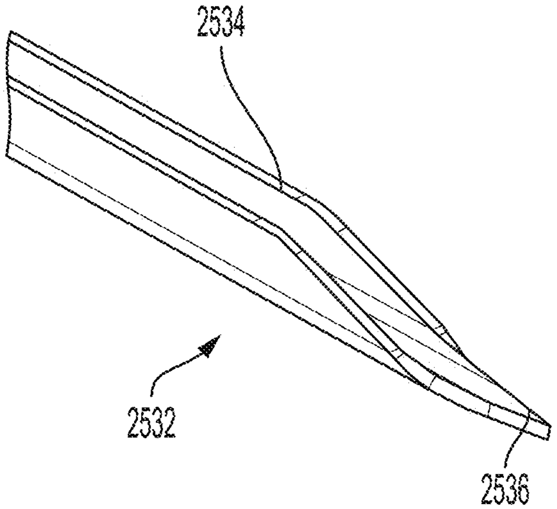
FIG. 12C is a close-up side perspective view depicting the distal tip of the sharp module illustrated in FIG. 12B.
Figure 12D:
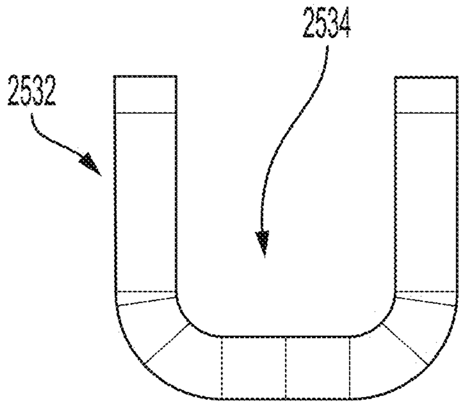
FIG. 12D is a cross-sectional view of a sharp embodiment for the sharp module illustrated in FIG. 12B.

FIG. 12B depicts another example embodiment of a sharp module 2530, and a callout view of the distal portion thereof, depicting the hollow or recess of sharp shaft 2534 and its distal tip 2536. FIG. 12C further illustrates a close-up side perspective view of distal tip 2536 which can penetrate the skin while carrying sensor tail (not shown) in a hollow or recess of sharp shaft 2534 to put the active surface of the sensor tail into contact with bodily fluid. The U-shaped implement of sharp 2532 is further illustrated in the cross-sectional view shown in FIG. 12D.

Figure 12F:
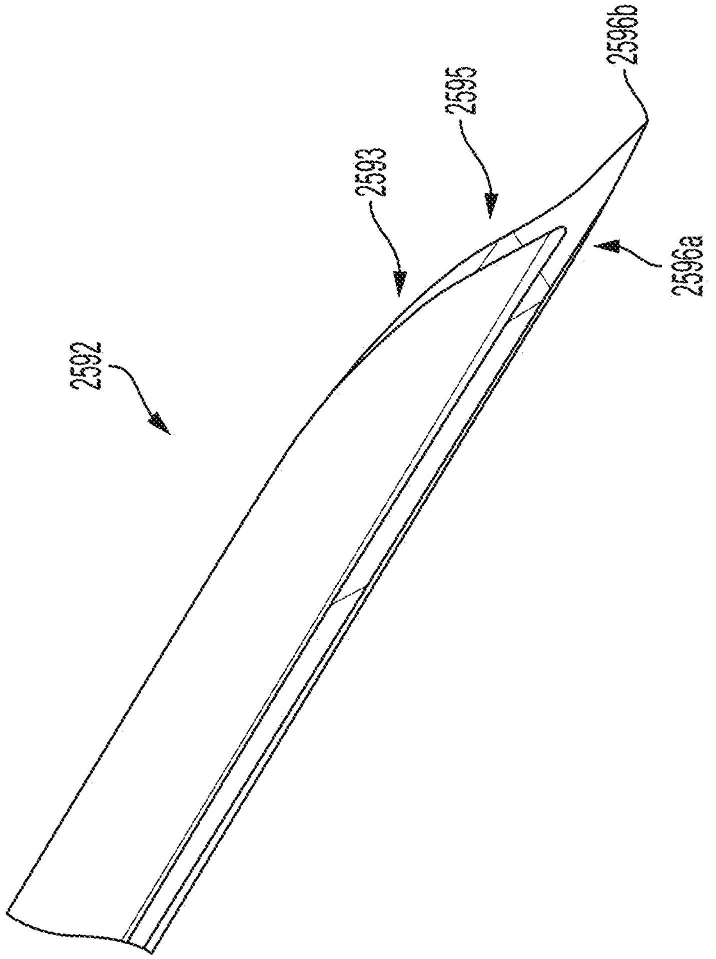
FIG. 12F is a close-up side view of an example embodiment of a sharp.
Figure 12E:
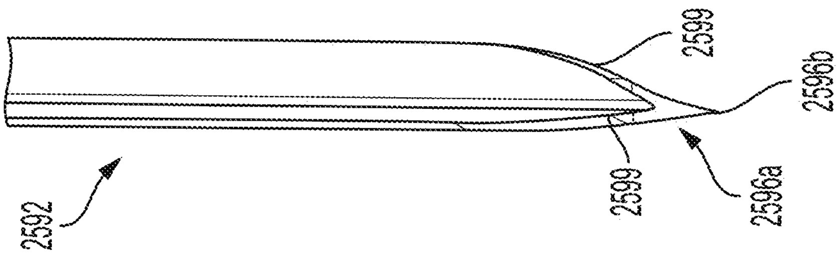
FIG. 12E is a close-up perspective view of an example embodiment of a sharp.

Example embodiments of a sharp designed to reduce trauma during a sensor insertion and retraction process will now be described. FIG. 12E is a close-up perspective view of a sharp 2592. In FIG. 12E, the sharp distal tip 2596*a* includes double beveled edges or transitions 2599 that adjoin at a proximal portion of the distal tip 2596*a* to form a distal tip 2596*a* having a vertex 2596*b*. Specifically, the double beveled edges 2599 are concavely sloped so as to form the sharp distal tip 2596*a*. Referring to FIG. 12E once more, the distal portion is provided with a concavely angled distal tip 2596*a*. As shown in FIG. 12F, the angled distal tip 2596*a* can be provided with a first concavely angled tip portion 2593 and a second steep-angled tip portion 2595. More specifically, the first concavely angled tip portion 2593 slopes into the second steep-angled tip portion 2595. The exemplary configuration, which includes multiple edges and faces, provides a sharp point to reduce penetration force, trauma, and bleeding for the subject. The sharp 2592 has a substantially V-shaped profile in this embodiment.

Figure 12G:
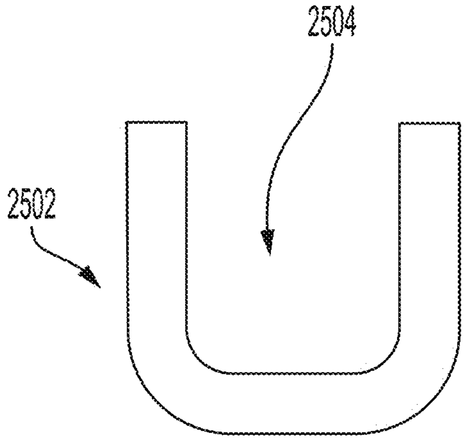
FIG. 12G. is a cross-sectional view of an example embodiment of a sharp.
Figure 12H:
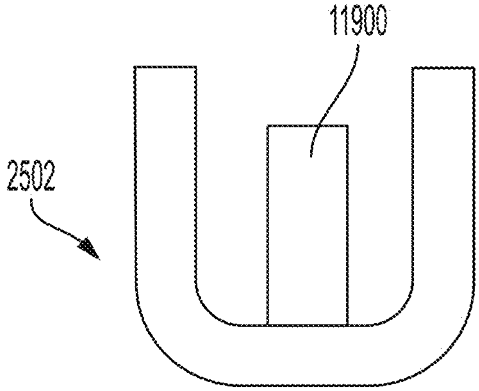
FIG. 12H is a cross-sectional view of the sharp depicted in FIG. 12G, further comprising an example embodiment of a sensor.
Figure 12I:
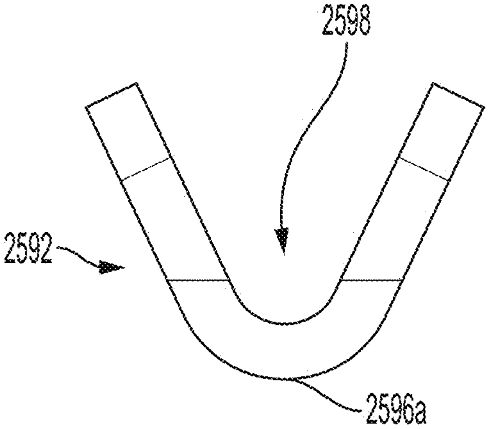
FIG. 12I is a cross-sectional view of an example embodiment of a sharp.
Figure 12J:
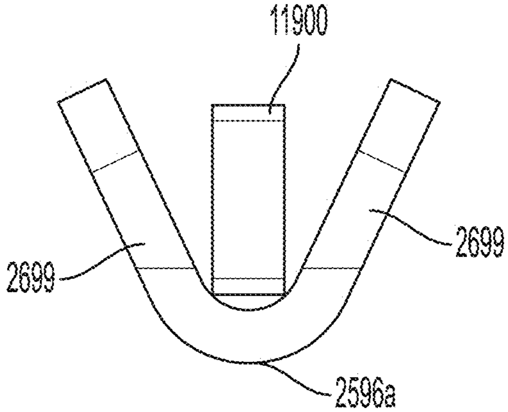
FIG. 12J is a cross-sectional view of the sharp depicted in FIG. 12I, further comprising an example embodiment of a sensor.

FIGS. 12G and 12I are cross-sectional view of two embodiments of the sharps described herein. FIG. 12G is a cross-sectional view of a previous embodiment, illustrating a substantially U-shaped cross-sectional area of sharp 2502. FIG. 12I is a cross-sectional view of an embodiment depicting a V-shaped cross-sectional area of sharp 2592, having a vertex 2596*a*. In some embodiments, the vertex 2596*a* includes a bottom portion of the cross-sectional area with no sharp edges. Additionally, the bottom portion of the cross-sectional area, unlike some U-shaped embodiments, such as the sharp embodiment illustrated in FIG. 12G, is not flattened. FIGS. 12H and 12J are cross-sectional views of the embodiments depicted in FIGS. 12G and 12I, respectively, illustrating the sharp embodiments supporting a sensor, for example, sensor 11900 or sensor 11950, respectively.

Figure 12K:
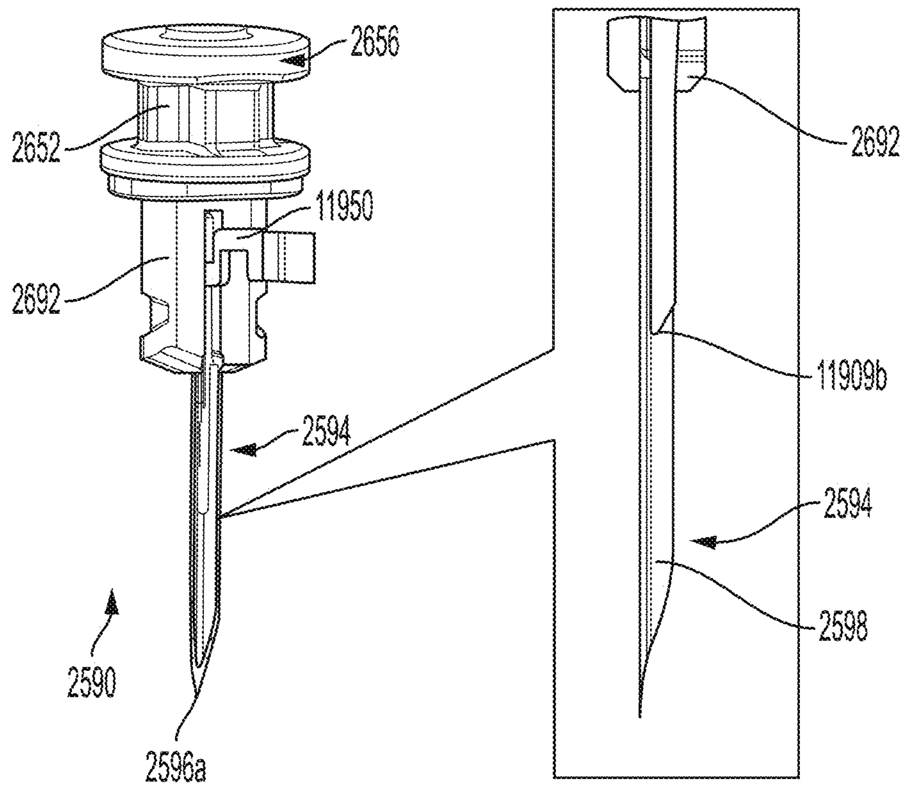
FIG. 12K is a partial perspective view of an example embodiment of a sharp module, and a callout view of the distal tip thereof.

FIG. 12K is a perspective view depicting an example embodiment of a sharp module 2590 having one or more beveled edges and V-shaped geometry configured to create a smaller opening in the skin relative to other sharps (e.g., sharp 2502 depicted in FIG. 12A). Sharp module 2590 is shown here prior to assembly with sensor module 504 (FIGS. 9A and 9B), and can include components similar to those of the embodiment described with respect to FIG. 12A, including sharp 2592, sharp shaft 2594, sharp distal tip 2596*a*, hub push cylinder (not shown), hub small cylinder 2652, hub snap pawl 2656 and hub snap pawl locating cylinder (not shown). Similar to the previously described sharp module 2500, and as shown in the callout view also depicted in FIG. 12K, sharp module 2590 can include a sharp shaft 2594 coupled to a distal end of the hub portion 2692 at a proximal end, sensor channel 2598 configured to receive at least a portion of an analyte sensor, such as analyte sensor 11950, for example, and a distal tip 2596*a* configured to penetrate a skin surface during the sensor insertion process.

Figure 12L:
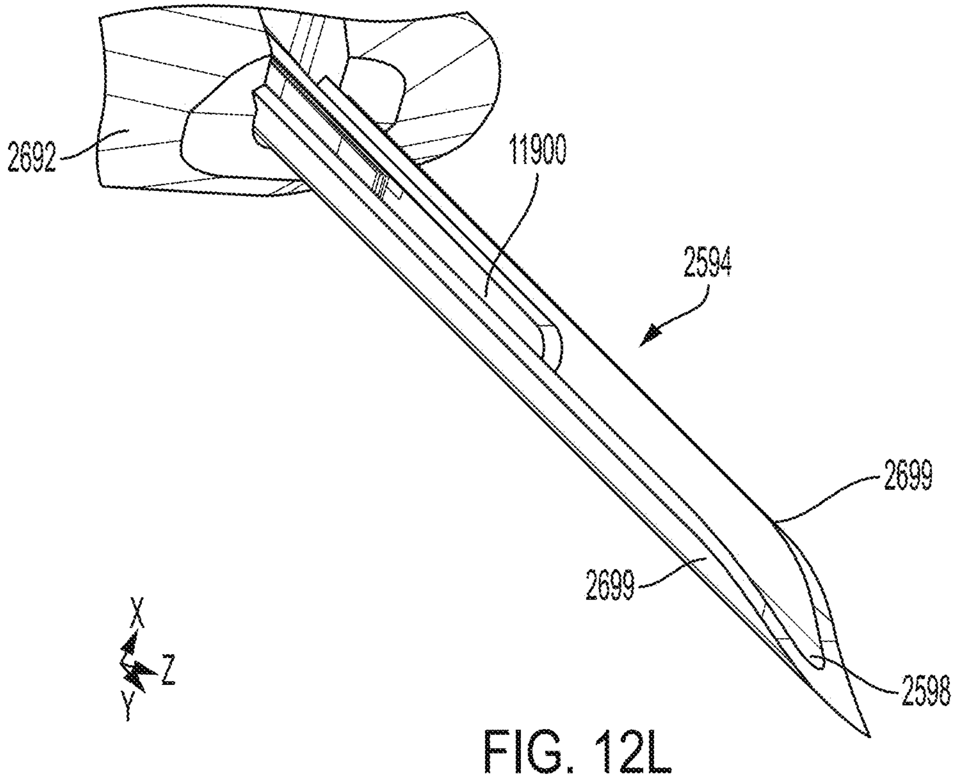
FIG. 12L is a close-up perspective view of the distal tip of an example embodiment of a sharp module comprising a sensor.

In FIG. 12K, a front perspective view of sharp shaft 2594 is depicted, and includes a sharp module 2590 comprising one or more sidewalls 2699 and a longitudinally-extending sensor channel 2598 that together form the sharp's V-shaped cross-sectional area comprising a vertex 2596*b*. Further, the sensor channel 2598 is configured to receive at least a portion of any analyte sensor which has been described herein, such as analyte sensor 1900 or 11950, for example. In some embodiments, such as the embodiment which is illustrated in FIG. 12L, sensor channel 2598 is configured to receive at least a portion of analyte sensor 11900. According to one aspect of the embodiments, one or all of the sharp portion 2592, the sharp shaft 2594, and/or the sharp distal tip 2596*a* of a sharp 2592 can comprise one or more concave beveled edges.

Referring to FIGS. 12K and 12L, according to one aspect of the embodiment, one or more sidewalls 2699 that form sensor channel 2598 are disposed along sharp shaft 2594 and are adjacent to the distal tip 2596*a*. Specifically, the one or more sidewalls 2699 are disposed along the sharp shaft 2594 such that the terminus of the one or more sidewalls 2699 is distal to the terminus of the sensor channel 2598. In some embodiments, for example, the terminus of the one or more sidewalls 2699 extend from the vertex 2596*b* of the sharp distal tip 2596*a*. The terminus of the one or more sidewalls 2699 adjoin at the proximal end of the distal tip 2596*a* so as to form the one or more beveled edges thereof. The one or more beveled edges are configured such that they concavely slope and define the vertex 2596*b* of the distal tip 2596*a*. In some embodiments, the vertex 2596*b* is centrally located at the sharp distal tip 2596*a*. According to one aspect of the embodiment, a sharp 2592 can be characterized as having a sharpened V-shaped distal tip 2596*a* with all other edges comprising double beveled edges.

The V-shaped tip portion 2596*a* of the sharp 2592 is designed such that it provides less surface area and includes a reduced cross-sectional footprint relative to, for example, distal tip 2506 of sharp module 2500. The cross-sectional area of the distal tip 2596*a* is the smallest cross-sectional area of the sharp module 2590. During insertion, as the sharp 2592 moves into the skin surface, the sharp point geometry and V-shaped cross-sectional area of the sharp 2592, as illustrated in FIGS. 12E-12L, penetrate the skin by making a smaller wound due to the smaller size of the tip portion. With respect to sensor insertion, puncture wounds can contribute to ESA in sensors. In this regard, the embodiments described herein provide for less trauma and, consequently, a reduced risk of ESA result during the sensor insertion process.

Furthermore, it will be understood by those of skill in the art that the sharp 2592 embodiment described herein can similarly be used with any of the sensors described herein, including in vivo analyte sensors that are configured to measure an analyte level in a bodily fluid of a subject. Moreover, the sharp embodiments described herein can similarly be used with in vivo analyte sensors comprising a V-shaped tip. For example, in some embodiments, as shown in FIG. 12K, sharp 2592 can include a sensor channel 2598 configured to receive at least a portion of an analyte sensor 11950 with a V-shaped tip 11909*b*. Further, the V-shaped tip portion 11909*b* of the sensor 11950 is adjacent to the sharp 2592 and permits the sharp 2592 to create an insertion path for the sensor 11950. In this embodiment, the sharp design itself, and the positioning of the needle with respect to the sensor can be implemented such that the assembly causes less trauma during the insertion process. The distal section of the sensor body has a width sized to fit within the sensor channel 2598. For example, the V-shaped tip portion 11909*b* of the sensor 11950 is designed to have a complementary shape to the V-shaped cross-sectional area of the sharp 2592. In this embodiment, the V-shaped tip portion 11909*b* of the sensor 11950 is optimized such that its tip portion 11909*b* is co-axial to the vertex 2596*b* of the sharp 2592 so as to better follow the distal tip 2596*a* as it penetrates the subject's skin.

Example Embodiments of a Container

With reference to FIGS. 13A to 13L, example embodiments of a container 3100 will now be described.

The container 3100 is provided for use with an insertion apparatus (otherwise referred to as an applicator) such as the insertion apparatus described herein. In particular, the container 3100 is provided for use with an insertion apparatus to be used for inserting at least a portion of a sensor into skin of a subject, for example inserting an analyte sensor (such as an in vivo glucose sensor). In other examples, the container 3100 can be referred to as a tray.

The container 3100 depicted in FIGS. 13A-13L includes the sensor, sharp, and the electronics to be loaded into the insertion apparatus (e.g., the applicator 150, 702). This allows the sensor and electronics to already be assembled, and to enable the insertion apparatus to be reusable. As such, the container 3100 is provided for storing an analyte monitoring assembly until loading into an insertion apparatus.

In more detail, as will be explained herein, the container 3100 is a disposable container 3100 for use with a reusable insertion apparatus (otherwise referred to as a reusable applicator or a resettable applicator). In other words, a single insertion apparatus can be used with multiple containers 3100 for inserting a plurality of sensors over time. Instead of discarding the insertion apparatus after inserting a single sensor, the insertion apparatus can be reset and used to insert another sensor using another disposable container 3100. For example, the container 3100 may be used with the resettable applicator 5150 (and reset tool 5100).

Figure 13A:
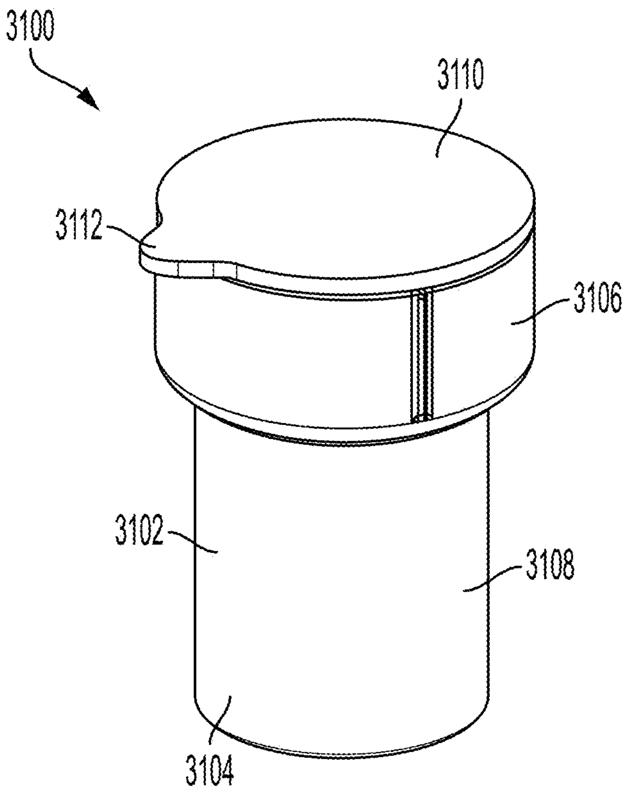
FIG. 13A is a perspective view of a container, in accordance with an exemplar embodiment of the disclosure.
Figure 13B:
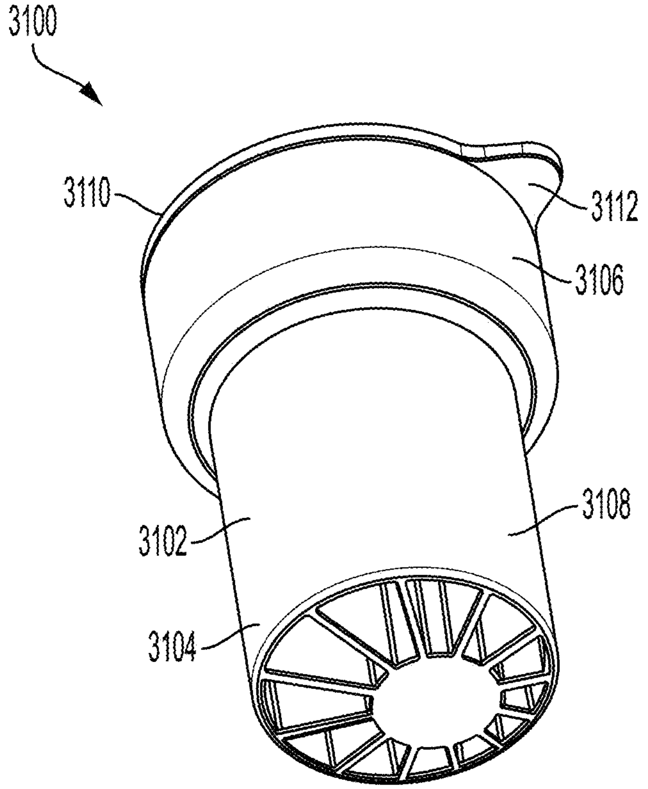
FIG. 13B is a perspective view from below of the container of FIG. 13A.

Referring in particular to FIGS. 13A and 13B, the container 3100 is shown from the outside. The container 3100 comprises a container body 3102. The container body 3102 is generally cylindrical. In other words, the container body 3102 has an elongate tube shape. The container body 3102 has a length and a width smaller than the length. The length of the container body 3102 extends from a proximal end at the top of FIG. 13A to a distal end at the bottom of FIG. 13A. In some embodiments, the container body 3102 has a circular cross section, and thus the width is a diameter. The container body 3102 has an outer surface 3104. In some embodiments, the outer surface 3104 defines a generally cylindrical surface around the container body 3102. The container body 3102 has a first end and a second end. The first end is at the proximal end of the container body 3102, which is shown towards the top of FIG. 13A. The second end is opposite the first end. The second end is at the distal end of the container body 3102, which is shown towards the bottom of FIG. 13A. In some embodiments, the first end of the container body 3102 is an open end (with a closure applied, as described herein), and the second end is a closed end. In other words, the container body 3102 forms a cup shape. The container 3012 can take the form of other shapes in other embodiments.

Still referring to FIGS. 13A and 13B, the container body 3102 comprises a first portion 3106 and a second portion 3108. The first portion 3106 is arranged at the top of the container body 3102. In other words, the first portion 3106 is arranged towards the first end of the container body 3102. Thus, the first portion 3106 is adjacent the proximal end. The second portion 3108 is adjacent the first portion 3106. The second portion 3108 is arranged at the bottom of the container body 3102. In other words, the second portion 3108 is arranged towards the second end of the container body 3102. Thus, the second portion 3108 is adjacent the distal end.

In some embodiments, and as best shown in FIGS. 13A and 13B, the first portion 3106 has an outer width which is larger than an outer width of the second portion 3108. In particular, as the cross section is circular, the diameter (and thus circumference) of the first portion 3106 is larger than the diameter (and thus circumference) of the second portion 3108. This means that the container body 3102 is generally formed from two cylindrical sections of different diameters. The first portion 3106 towards the proximal end of the container 3102 is wider, whereas the second portion 3106 is narrower. Thus, the generally cylindrical shape of the container body 3102 is formed from two cylindrical sections of different diameter. This forms a ledge between the first portion 3106 and the second portion 3108. At the ledge, the outer surface 3104 can form a sloped surface joining the first portion 3106 to the second portion 3108 or the ledge can extend radially to provide a flat surface. The first portion 3106 has a length which is less than a length of the second portion 3108. In some embodiments, the second portion 3108 is longer than the first portion 3106, in particular at least twice as long. In other examples, the container body 3102 does not include two portions, and instead can have a constant diameter (e.g., a cylinder) or a tapered configuration, and other shapes are possible.

The second portion 3108 is configured as a handle. In particular, the second portion 3108 is provided to be held by a user. The second portion 3108 can thus be sized to fit within a user's hand. Because the second portion 3108 has an elongated length, this improves case of handling by a user. Additionally, the ledge between the first portion 3106 and the second portion 3108 due to the different widths improves the case of handling.

In some embodiments, the container body 3102 can include features to promote grip. In particular, the container body 3102 can comprise one or more gripping elements on the outer surface 3102. For instance, the outer surface 3102 can comprise protruding or recessed elements such as ridges, bumps, or grooves, or other surface features to improve grip for the user.

According to an aspect of the embodiments, the container 3100 also comprises a closure 3110 (e.g., FIGS. 13A-13B). The closure 3110 can be referred to as a lid or a cap. The closure 3110 is arranged at the first end of the container body 3102. The closure 3110 is configured to close the otherwise open first end of the container body 3102. The closure 3110 is sized to fit into the first end of the container body 3102. In other words, the closure 3110 has an outward-facing rim with a width (e.g. diameter) substantially equal to the width (e.g. diameter) of an inward-facing rim of the first portion 3106 at the first end of the container body 3102. In some embodiments, the closure 3110 has an outer diameter substantially equal to the first portion 3106. In other examples, the closure 3110 fits around the first end such that the closure 3110 has an inward-facing rim fitting against an outward-facing rim of the outer surface 3104 of the first portion 3106. In some embodiments, the closure 3110 is removable from the container 3100. In some examples, the closure 3110 can couple to the container body 3102, for example by an interference fit, a threaded engagement, or other method. In other examples, the closure 3110 can be integral with the container body 3102 and can be opened while maintaining coupling, such as via a hinge. For example, the closure 3110 could be connected to the container body 3102. In some embodiments, the closure 3110 is rigid to provide protection for the contents of the container 3100, and also to provide support for the analyte monitoring assembly. In other examples, the closure 3110 could take the form of a flexible closure such as a film.

As shown in FIG. 13A, the closure 3110 has a flat upper surface. The closure 3110 is generally circular. According to an aspect of the embodiments, the closure 3110 comprises a tab 3112. The tab 3112 is arranged at a position along the outer circumference of the closure 3110. The tab 3112 protrudes in the radial direction of the closure 3110. In particular, the tab 3112 protrudes beyond the first portion 3106. The closure 3110 is generally circular with an outer diameter substantially equal to an outer diameter of the first portion 3106 such that the closure 3110 is flush with the side of the outer surface 3104, except for the tab 3112. The tab 3112 projects from outer surface 3104. The tab 3112 is provided for a user to grip to pull the closure 3110 to remove the closure 3110 from the container body 3102. In other examples, other tabs or mechanisms for closure removal/opening can be provided.

Figure 13C:
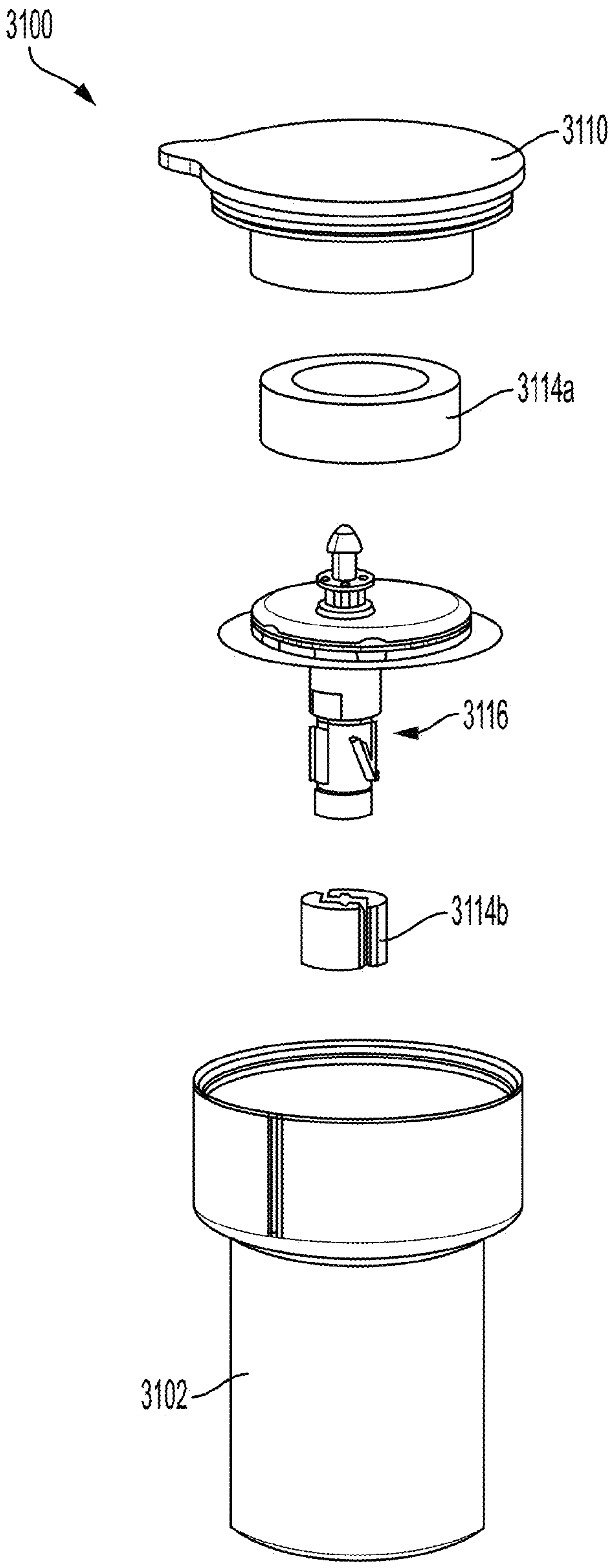
FIG. 13C is an exploded view of the container of FIG. 13A.

Referring in particular to FIG. 13C, the contents of the container 3100 are shown in an exploded view. The container 3100 comprises the container body 3102 and the closure 3110 for closing the container body 3102, as described in relation to FIGS. 13A and 13B. In some embodiments, optional desiccant(s) 3114 can be provided. For example, FIG. 13C shows optional desiccants 3114*a*, 3114*b*. Additionally, FIG. 13C illustrates an analyte monitoring assembly 3116 that is to be housed in the container body 3102. The analyte monitoring assembly 3116 is positioned within the container body 3102, and the closure 3110 is closed over the first end of the container body 3102 to seal the analyte monitoring assembly 3116 in the container body 3102. The desiccant(s) 3114 can be provided to absorb water and maintain a dry environment. The desiccant(s) 3114 can absorb unwanted outgassing or moisture. The desiccant 3114 can be snapped, press fit, or two-shot molded, for example. FIG. 13C best depicts two alternative locations for the desiccant(s) 3114*a*, 3114*b*, which can be positioned above and/or below the analyte monitoring assembly 3116. In some embodiments, the desiccant 3114 is arranged within the cap 3110 and around the support post 3140 (described below), but in other examples can be provided in one or other of these locations. In some embodiments, the desiccant(s) 3114 is not present.

Figure 13D:
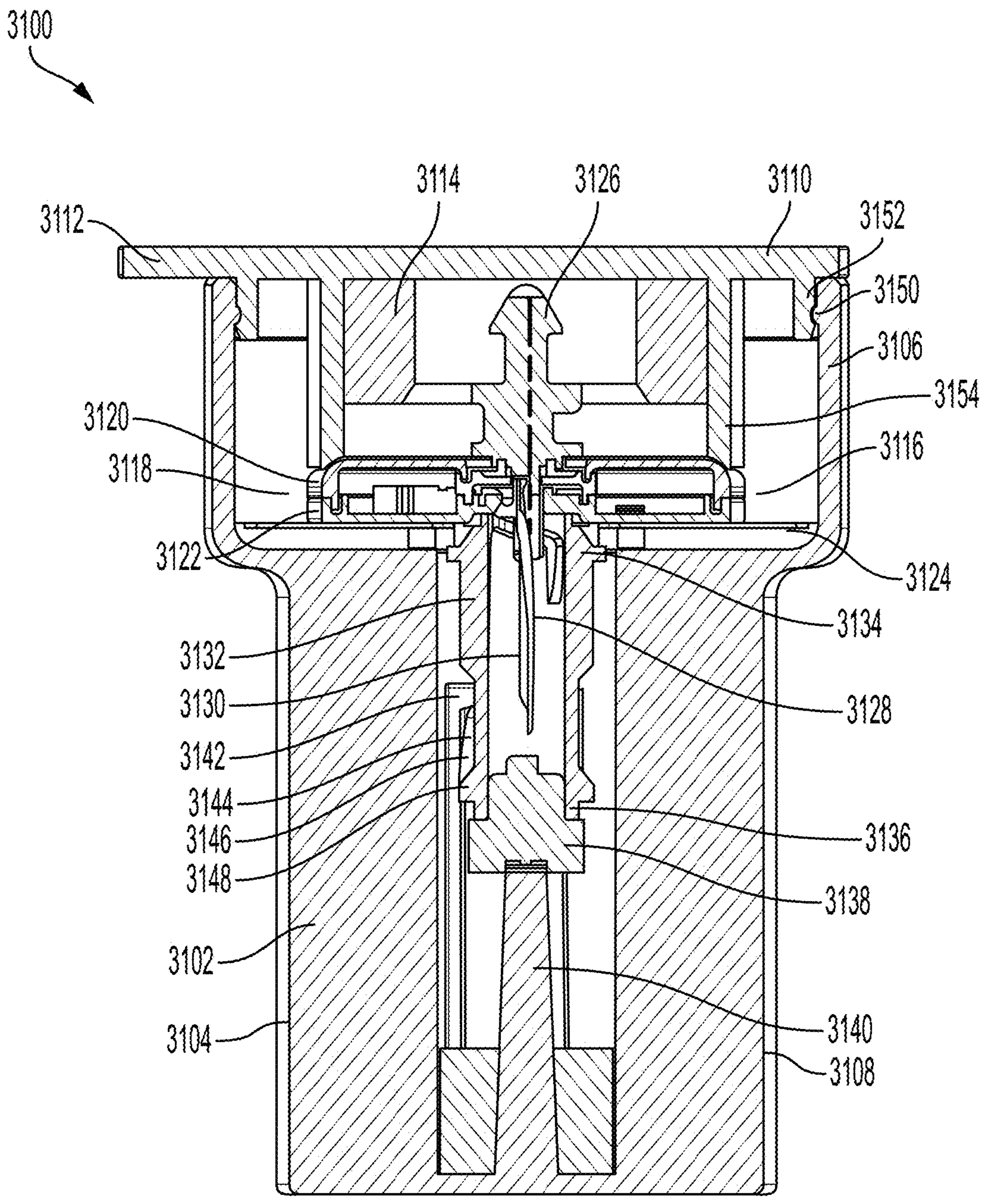
FIG. 13D is a side cross-sectional view of the container of FIG. 13A.
Figure 13E:
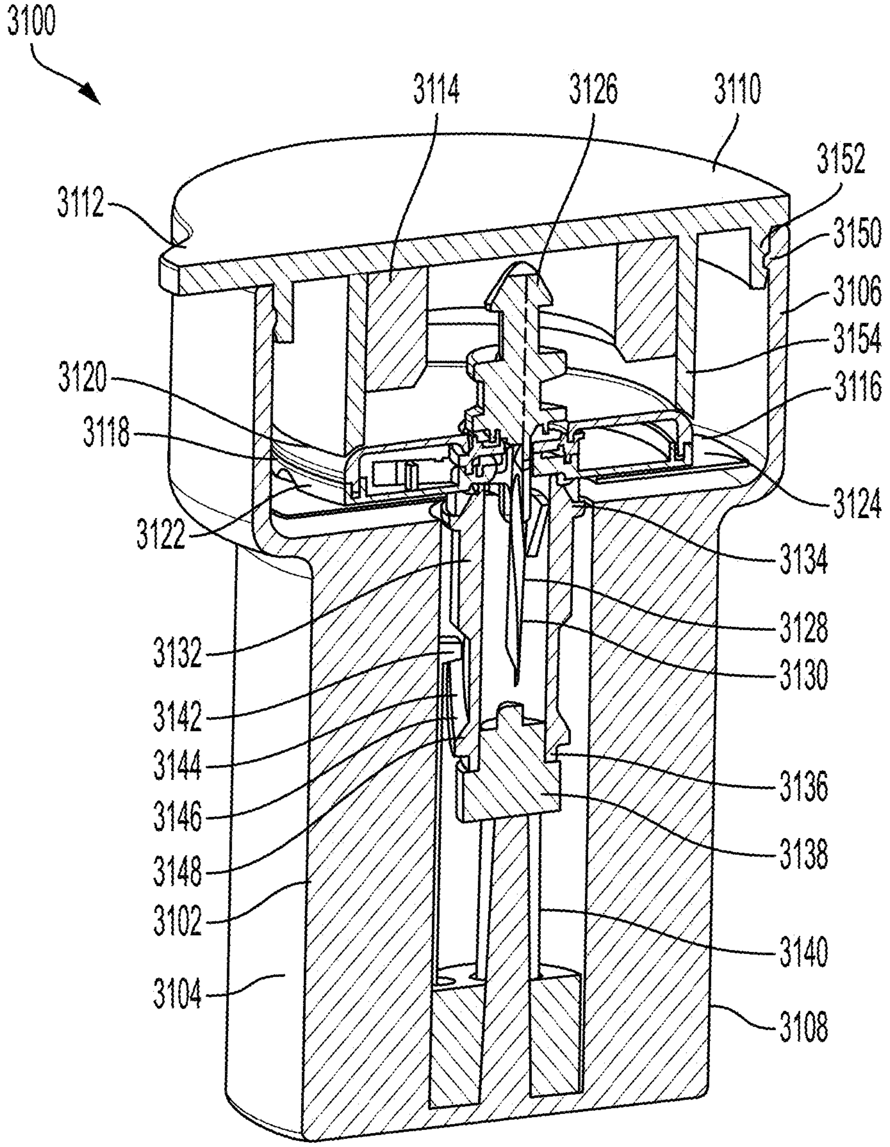
FIG. 13E is a perspective cross-sectional view of the container of FIG. 13A.

Referring in particular to FIGS. 13D and 13E, the container 3100 is shown in cross-section with the closure 3110 applied to the container body 3102 to close the otherwise open first end of the container body 3102. The container 3100 comprises the analyte monitoring assembly 3116 housed within the container body 3102.

The analyte monitoring assembly 3116 is a combination of components used for monitoring an analyte of the subject, such as glucose. The analyte monitoring assembly 3116 provides the components to be removed by the reusable insertion apparatus. In particular, the analyte monitoring assembly 3116 comprises a sensor control device 3118. The sensor control device 3118 can comprise one or more features of the sensor control device as described herein. For example, the sensor control device 3118 can be similar to the sensor control device 102 as described herein.

In exemplar embodiments, and as best shown in FIGS. 13D-13G, the sensor control device 3118 comprises a housing, and in particular in this embodiment takes the form of a shell. In particular, the sensor control device 3118 comprises an upper shell 3120 and a lower shell 3122. The upper shell 3120 and the lower shell 3122 interface to form a shell with a hollow interior. In some embodiments, the upper shell 3120 clips into a groove defined in the lower shell 3122, but other attachment configurations are possible. Other configurations for providing a housing are possible. The sensor control device 3118 is configured to house sensor electronics within the housing. The sensor control device 3118 also comprises an adhesive patch 3124. The adhesive patch 3124 is arranged on the base surface of the housing, which, in some embodiments, is on a distal surface of the lower shell 3122 (in other words, facing away from the closure 3110). The adhesive patch 3124 comprises an adhesive on the distal surface. The adhesive patch 3124 is provided for attaching the sensor control device 3118 to the subject's skin. In some embodiments, the adhesive patch 3124 is spaced away from the container body 3102.

Figure 13F:
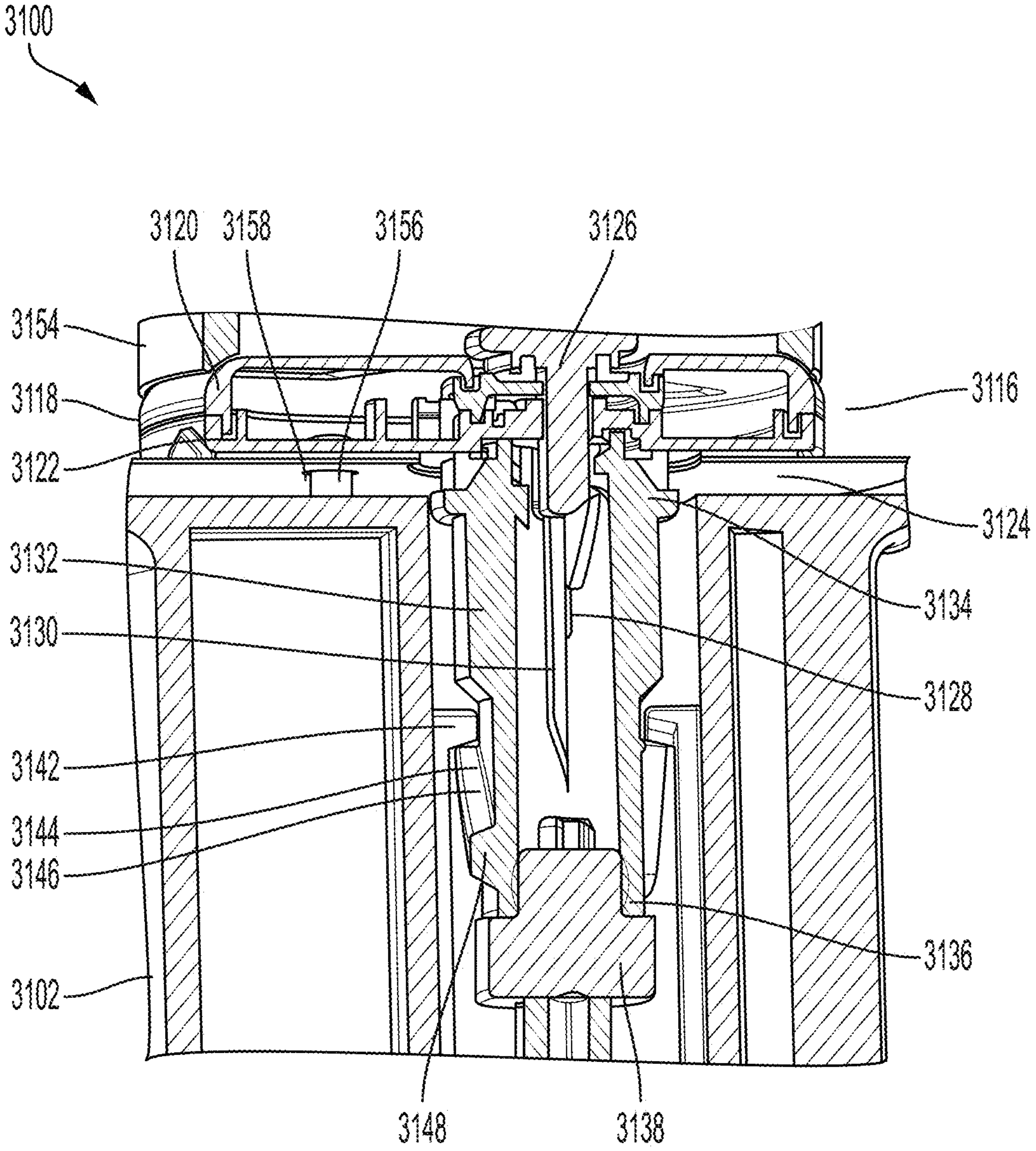
FIG. 13F is a close-up perspective cross-sectional view of the container of FIG. 13A.

As best depicted in FIGS. 13D-13F, the analyte monitoring assembly 3116 comprises an analyte sensor 3128. The sensor 3128 can comprise one or more features of the sensor as described herein. For example, the sensor 3128 can be similar to the sensor 104, 11900, 11950 as described herein. In some exemplar embodiments, the sensor 3128 is an analyte sensor such as a glucose sensor, but other sensors are possible.

With reference to FIGS. 13D-13F, the sensor 3128 protrudes below the sensor control device 3118 as described herein. In particular, the sensor 3128 extends distally from the lower shell 3122 of the sensor control device 3118. This means that as the sensor control device 3118 is placed onto the skin, at least a portion (e.g., a distal portion) of the sensor 3128 is inserted into the skin. For example, this allows the sensor to be in contact with interstitial fluid of the subject. Another portion of the sensor 3128 (e.g., a proximal portion) can be coupled to the sensor control device 3118, such as via electrical contacts. In exemplar embodiments, the distal portion is arranged longitudinally (e.g., vertically) while the proximal portion is at an angle such as perpendicular (e.g., horizontal) within the housing of the sensor control device 3118.

In some embodiments, and as best shown in FIGS. 13D-13G, and 13J, the container 3100 comprises a sharp hub 3126. The sharp hub 3126 can be referred to as a needle hub or a sharp/needle module. The sharp hub 3126 can comprise one or more features of the sharp module as described herein. For example, the sharp hub 3126 can be similar to the sharp module 2500 as described herein.

According to example embodiments, and with reference to FIGS. 13D-13F, the container 3100 also comprises a sharp 3130. The sharp 3130 can comprise one or more features of the sharps as described herein. For example, the sharp 3130 can be similar to the sharp 2502, 2532, 2592 as described herein. In some embodiments, the sharp 3130 is at least partially aligned with the sensor 3128. In particular, the sensor 3128 is arranged adjacent and inside the sharp 3130 as described herein. In some embodiments, the sharp 3130 comprises a sensor channel configured to receive at least a portion of the sensor 3128. More specifically, the distal section or tail of the sensor 3128 has a width sized to fit within the sensor channel. This allows the sharp 3130 to be used to insert the sensor 3128. The sharp 3130 can move freely axially relative to the sensor 3128. In other examples, a sharp 3130 is not provided and instead the sensor 3128 can be configured to be inserted into the skin without use of a sharp 3130.

According to one aspect of the embodiments, the sharp 3130 extends through the analyte monitoring assembly 3116. In particular, the sharp 3130 extends through an aperture in the housing of the sensor control device 3118. The sensor control device 3118 is configured to receive the sharp 3130 therethrough. The aperture is aligned with the sensor 3128 so that the sharp 3130 can be arranged adjacent the sensor 3128. In some embodiments, the aperture extends through the upper shell 3120 and the lower shell 3122. The sharp 3130 can thus extend through the upper shell 3120, through the housing, and through the lower shell 3122.

Figure 13G:
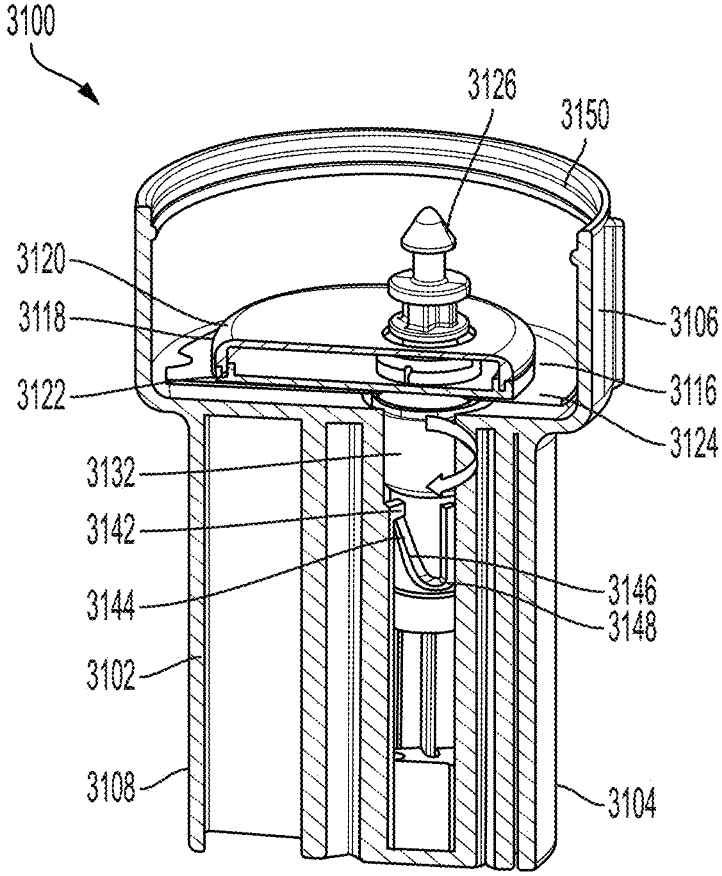
FIG. 13G is a perspective cross-sectional view of the container of FIG. 13A, with the closure removed.

Referring to FIGS. 13D-13F, the sharp 3130 and the sharp hub 3126 can be part of the analyte monitoring assembly 3116. Thus, the sharp 3130 and the sharp hub 3126 can be removed from the container body 3102 along with the sensor control device 3118 and the analyte sensor 3128 as part of the analyte monitoring assembly 3116. As best illustrated in FIGS. 13D, 13E, and 13G, the sharp hub 3126 is arranged at the proximal end of the analyte monitoring assembly 3116 for maneuvering the sharp 3130. In particular, the sharp hub 3126 comprises a cone-shape (e.g., similar to hub snap pawl 2516 of sharp module 2500) which can be used by an insertion apparatus (e.g. using sharp carrier 1102) to leverage the sharp hub 3126 and to withdraw the sharp 3130 from the analyte monitoring assembly 3116 once the sensor 3128 has been inserted using the sharp 3130. Thus, the sharp hub 3126 is removable from the sensor control device 3118 in response to a proximal force, and can withdraw the sharp 3130.

Referring to FIGS. 13D-13G, the sensor 3128 is coupled to the sensor control device 3118, such as to sensor electronics. In particular, the sensor 3128 is configured to be electrically coupled to the sensor electronics of the sensor control device 3118. This allows the sensor 3128 to provide an electrical signal to the sensor electronics for obtaining measurement data.

As best depicted in FIGS. 13D, 13E, and 13G, in some exemplar embodiments, the sensor control device 3118 is arranged in the first portion 3106 of the container body 3102. The outer surface 3104 of the container body 3102 defines the outer circumference of the first portion 3106 and the second portion 3108 (e.g., FIG. 13D-13E). The container body 3102 also comprises an inner surface. The inner surface is parallel to the outer surface 3104 along the wall of the first portion 3106, defining a thickness of the wall. This defines a cylindrical interior of the first portion 3106, in which the sensor control device 3118 is arranged. In some embodiments, the sensor control device 3118 is circular and the first portion 3106 is correspondingly circular, but different shapes can be provided, for example, if the sensor control device 3118 is a different shape.

Still referring to FIGS. 13D, 13E, and 13G, the inner surface then defines a lower surface of the first portion 3106. In particular, the inner surface extends radially inwards perpendicular to the height of the first portion 3106 (e.g., horizontally). The lower surface extends part way to the center of the first portion 3106. The lower surface is arranged adjacent the distal end of the first portion 3106 joining the second portion 3108. The lower surface of the first portion 3106 effectively partially separates the first portion 3106 from the second portion 3108. The lower surface provides a support for the sensor control device 3118. However, the adhesive patch 3124 is positioned above, spaced away from, and not in contact with, the lower surface. In other words, the container 3100 comprises a clearance between the adhesive patch 3124 and the container body 3102 (in particular to the lower surface of the first portion 3106).

The inner surface then extends distally along the length of the second portion 3108, parallel to the outer surface 3104 at the second portion 3108. This defines a cylindrical interior of the second portion 3108. The cylindrical interior defined by the inner surface in the second portion 3108 has a smaller diameter than the cylindrical interior defined by the inner surface in the first portion 3106. The second portion 3108 is configured to house at least part of the sensor 3128. In some embodiments, the inner surface is spaced from the outer surface 3104 in the second portion 3108, and a hollow space is provided between. This reduces the amount of material required, reducing weight and cost. As best shown in FIG. 13B, the underside (distal end) of the container 3100 includes a plurality of radial spokes from the outer surface 3104 of the second portion 3108 to the cylindrical interior. This maintains the structure whilst reducing the amount of material. The distal end of the cylindrical interior is closed. The cylindrical interior is off-center from the center of the circular cross section of the second portion 3018 in order to house the sensor 3128 which is off-center from the sensor control device 3118 (best shown in FIGS. 13C and 13G). In other embodiments, the sensor 3128 is centered or longitudinally aligned with the sensor control device 3118.

According to some aspects of the embodiments, and with reference to FIGS. 13D-13G, the container 3100 further comprises a sensor cap 3132. The sensor cap 3132 is generally cylindrical. As best illustrated in FIG. 13F, the sensor cap 3132 has a first end 3134 which is a proximal end, and a second end 3136 opposite the first end 3134, wherein the second end 3136 is a distal end. The first end 3134 is the proximal end of the cylindrical shape, and the second end 3136 is the distal, opposite end of the cylindrical shape. In some embodiments, both the first end 3134 and the second end 3136 are open ends.

Still with reference to FIGS. 13D-13G, the sensor cap 3132 is arranged distally of the sensor control device 3118. In particular, the first end 3134 is coupled to the analyte monitoring assembly 3116, specifically to the sensor control device 3118. In more detail, the first end 3134 is screwed onto the housing of the sensor control device 3118. In some embodiments, the first end 3134 of the sensor cap 3132 is screwed onto the sensor control device 3118 via the lower shell 3122. In other examples, the sensor cap 3132 can be coupled to the sharp hub 3126 should this extend through the aperture of the sensor control device 3118. The sensor cap 3132 is arranged over at least a portion of the sensor 3128. According to an aspect of the embodiments, the sensor cap 3132 covers the sensor 3128 which protrudes distally from the lower shell 3122 of the sensor control device 3118. In some embodiments, the sensor cap 3132 also covers the sharp 3130. This ensures that the sensor 3128 (and the sharp 3130) is protected. As the first end 3134 of the sensor cap 3132 is coupled to the sensor control device 3118, the sensor cap 3132 is closed at the first end 3134. In some embodiments, the sensor cap 3132 is sealed at the first end 3134. The sensor cap 3132 is arranged to extend through the lower surface of the inner surface of the first portion 3106 of the container body 3102. In other words, the lower surface extends radially inwards, but leaves room for the sensor cap 3132. This allows the sensor cap 3132 to pass between the second portion 3108 and the first portion 3106, to connect to the sensor control device 3118.

In some embodiments, and as best illustrated in FIGS. 13D-13F, the second end 3136 of the sensor cap 3132 is coupled to a plug 3138. The plug 3138 is configured to close the second end 3136. Thus, the sensor cap 3138 is sealed at the second end 3136. The plug 3138 is supported on a support post 3140 which is connected to the base of the container body 3102. In this manner, the sensor cap 3132 is sealed over the sensor 3128. This is useful because it can isolate the sensor 3128 from contaminants. In particular, the sensor 3128 can be kept sterile. This also supports the analyte monitoring assembly 3116 because the plug 3138, supported by the support post 3140, engages the sensor cap 3132, which in turn engages the analyte monitoring assembly 3116. In this manner, the analyte monitoring assembly 3116 is supported proximally. This also allows the sensor control device 3118 to be supported away from the container body 3102 and to provide a clearance between the lower shell 3122 (and the adhesive patch 3124) and the lower surface of the first portion 3106 of the container body 3102.

In some embodiments, and as best depicted in FIGS. 13D-13G, the container body 3102 also comprises a retaining element 3142. The retaining element 3142 is formed from the inner surface of the container body 3102, but in other examples can be separate and attached to the inner surface of the container body 3102. The retaining element 3142 is formed on the inner surface at the second portion 3108. According to an aspect of the embodiments, the retaining element 3142 comprises a tab. The retaining element 3142 can otherwise be referred to as a protrusion, a projection, or an extension. In some examples, the retaining element 3142 can be referred to as an overhang. The retaining element 3142 is configured to engage with the sensor cap 3132. In particular, the sensor cap 3132 comprises an interface element 3144. The interface element 3144 is arranged on the outer surface of the sensor cap 3132. The interface element 3144 can be referred to as a protrusion, a projection, or an extension. The interface element 3144 protrudes from the outer surface of the sensor cap 3132.

Still referring to FIGS. 13D-13G, in some embodiments, the interface element 3144 comprises a ramp 3146. The ramp 3146 extends along a length of the outer surface of the sensor cap 3132. The ramp 3146 is an element that projects from the outer surface of the sensor cap 3132 and extends both around the outer surface of the sensor cap 3132 and along the length of the sensor cap 3132. In other words, the ramp 3146 extends in a helical shape around the outer surface of the sensor cap 3132.

As shown in FIGS. 13D-13G, the retaining element 3142 of the container body 3102 is positioned proximally of the ramp 3146. In FIGS. 13D and 13E, the retaining element 3142 is shown above the ramp 3146 (i.e., closer to the first end 3134 of the sensor cap 3132). The retaining element 3142 extends radially inwards proximally of the ramp 3146 such that the retaining element 3142 is aligned with the protrusion of the ramp 3146 in a direction along the length of the sensor cap 3132. The retaining element 3142 thereby prevents the sensor cap 3132 from moving proximally past the retaining element 3142. As described herein, the retaining element 3142 is configured to move along the ramp 3146 during use.

In some embodiments, the sensor cap 3132 also comprises an end stop 3148. The end stop 3148 is arranged at the bottom of the ramp 3146, and is used to limit the movement of the retaining element 3142 along the ramp 3146. As best shown in FIG. 13G, the end stop 3148 is shown as a projection extending along a portion of the circumference and facing proximally. In this manner, the end stop 3148 prevents proximal movement of the sensor cap 3132 due to the retaining element 3142 engaging the end stop 3148. According to an aspect of the embodiments, the ramp 3146 and the end stop 3148 form a U-shape. This retains the retaining element 3142, preventing the sensor cap 3132 from being released by the container body 3102. This prevents the sensor cap 3132 from falling out of the container body 3102 after removal of the analyte monitoring assembly 3116 from the container body 3102, improving convenience, and ensuring the proper exposure of the sensor 3128 and the sharp 3130 for insertion.

Referring back to FIGS. 13D-13G, in some exemplar embodiments, the container 3100 comprises two ramps 3146 on opposing sides of the sensor cap 3132, and two corresponding retaining elements 3142 (only one shown in FIGS. 13D, 13E, and 13G) for engaging the ramps 3146. This can improve stability by engaging the sensor cap 3132 at multiple (e.g., opposite) locations. In other embodiments, other arrangements are possible, such as a single ramp 3146 and retaining element 3142, or more than two, for example.

In some embodiments, and as best depicted in FIGS. 13D-13E, the container body 3102 comprises a lip 3150. The lip 3150 is arranged adjacent the first end (proximal end) of the first portion 3106 of the container body 3102. The lip 3150 is arranged around the inner surface of the first portion 3106. The lip 3150 is an annular inward projection around the inner circumference of the container body 3102 and extends inwards towards the central axis of the first portion 3106. The lip 3150 is configured to retain the closure 3110 in place when the closure 3110 closes the first end. In particular, the closure 3100 comprises an engagement surface 3152 (FIGS. 13D-13E) which is a cylindrical surface extending distally from the closure 3110. The engagement surface 3152 is thus perpendicular to the flat upper surface of the closure 3110. The engagement surface 3152 is configured to engage the inner surface of the container body 3102 at the first end. The engagement surface 3152 is configured to engage with the lip 3150 to retain the closure 3110 in place to close the first end of the container body 3102.

According to an aspect of the embodiments, and as best depicted in FIGS. 13D-13E, the engagement surface 3152 is configured to snap over the lip 3150 to secure the closure 3110 in place. The engagement surface 3152 of the closure 3110 and the lip 3150 of the container body 3102 thus form a snap fit to secure the closure 3110 to close the container body 3102. The fit forms a seal which provides a moisture barrier. This seal prevents passage of moisture to prevent moisture from entering the container 3100. This can be used to increase the shelf-life of the container 3100. In some examples, the engagement surface 3152 can comprise a projection for snap fitting distally of the lip 3150 (or into a recess in the container body 3012) and/or a recess for receiving the lip 3150.

In other examples, the closure 3110 and the container body 3102 can form other fits, such as an interference fit, or press fit, or friction fit. In yet other examples, the closure 3110 can be screwed onto the container body 3102. For instance, the lip 3150 can define a thread for interacting with a screw thread of the closure 3110. The screw connection can provide a moisture barrier in a similar manner to the snap fit. In some examples, a seal can be provided, such as by a compressible member such as an O-ring or gasket, between the container body 3102 and the closure 3110 to form a moisture seal.

As illustrated in FIGS. 13D-13E, in some embodiments, the closure 3110 also comprises a support element 3154. The support element 3154 is a cylindrical wall which extends distally from the closure 3110. The support element 3154 is thus perpendicular to the flat upper surface of the closure 3110 and parallel to the engagement surface 3152. The support element 3154 extends distally to engage the sensor control device 3118. In particular, the support element 3154 contacts the housing, in this example at the upper shell 3120 of the sensor control device 3118. In this manner, the support element 3154 supports the sensor control device 3118 and prevents proximal movement of the sensor control device 3118 when the closure 3110 is applied to the container body 3102. In this manner, the closure 3110 supports the sensor control device 3118. In some embodiments, the support element 3154 engages the upper shell 3120 at the corner between the upper surface and the side edge. In this manner, the support element 3154 can prevent radial movement as well as proximal movement. In this manner, the analyte monitoring assembly 3116 is securely held between the support post 3140 of the container body 3102 and the support element 3154 of the closure 3110. This reduces movement during storage and transport, avoiding damage before use.

In other examples, the container body 3102 can support the sensor control device 3118, such as by providing a support element to hold the sensor control device 3118 in place (e.g., at the housing such as at the upper shell 3120). In such examples, the support element of the container body 3102 can be retractable or resilient such that it can be overcome such that the sensor control device 3118 can be removed from the container body 3102 when desired. In some embodiments, because the support element 3154 is integral with the closure 3110, the support element 3154 is removed from the upper shell 3120 when the closure 3110 is removed, and therefore the sensor control device 3118 is automatically released by the support element 3154 as the closure 3110 is removed.

According to another aspect of the embodiments, the closure 3110 is made from plastic, such as rigid plastic. For example, the plastic can be polypropylene or high-density polyethylene (HDPE). In other examples, the closure 3110 can comprise a removable film which can be removed for exposing the analyte monitoring assembly 3116. However, in some embodiments, the closure 3110 allows the support element 3154 to support the analyte monitoring assembly 3116 in position during shelf-life and transit, as well as protecting the analyte monitoring assembly 3116 from drop, shock, or vibration, for example.

In exemplar embodiments, a desiccant 3114 is arranged proximally of (e.g., above) the sensor control device 3118 (see, e.g., FIGS. 13D-13E). In particular, desiccant 3114 is arranged within the circumferential wall of the support element 3154. The desiccant 3114 can be attached to the closure 3110 and can be removed with the closure 3110 (or can be removed separately) to expose the analyte monitoring assembly 3116.

Referring in particular to FIG. 13F, the container 3100 comprises an alignment post 3156. In particular, the alignment post 3156 extends proximally from the lower surface of the inner wall of the first portion 3106 of the container body 3102. In some embodiments, the container 3100 comprises three alignment posts 3156 over the lower surface (only one is clearly shown in FIG. 13F). In other examples, other numbers of alignment posts 3156 can be provided, such as at least one (e.g., one) or at least two (e.g., two).

In some embodiments, and still with particular reference to FIG. 13F, the alignment post 3156 extends proximally through an alignment hole 3158 in the lower shell 3122 of the sensor control device 3118 (and also through a corresponding hole in the adhesive patch 3124). The alignment post 3156 is thus received by the sensor control device 3118. Thus, the alignment post 3156 is configured to align the sensor control device 3118 relative to the container body 3102. Further, the alignment post 3156 allows the sensor control device 3118 to be supported away from the container body 3102 and provides a clearance between the lower shell 3122 (and the adhesive patch 3124) and the lower surface of the first portion 3106 of the container body 3102. The alignment post 3156 is also configured to retain the sensor control device 3118 in position. This prevents damage, and also allows the insertion apparatus to easily remove the analyte monitoring assembly 3116 as it is located in a known position. Furthermore, by providing at least two alignment posts 3156 received into corresponding alignment holes 3158 in the lower shell 3122, the container body 3102 can prevent rotation of the sensor control device 3118 about a single alignment post 3156. However, if the sensor control device 3118 is moved proximally (e.g., once the closure 3110 is removed), then the sensor control device 3118 can be withdrawn and removed from the alignment posts 3156 without interference.

In other examples, other alignment features can be provided for aligning the sensor assembly 3116 relative to the container body 3102. For example, though not illustrated, the container body 3102 can comprise snap(s) configured to limit radial and/or axial motion of the sensor control device 3118 and retain the sensor control device 3118 in position within the container body 3102 until withdrawn by the insertion apparatus. In this regard, the snaps support and stabilize the sensor control device 3118 after the closure 3110 is removed and prior to withdrawal of the analyte monitoring assembly 3116 by the insertion apparatus. Further, the alignment features, (e.g., snaps) can protect the sensor control device 3118 from drop, shock, vibration, or the like. Further, the force exerted by the snaps can be overcome by features in the reusable insertion apparatus which can lock onto the sensor control device 3118 so as to pull it in a proximal direction away from the container 3100.

Referring in particular to FIGS. 13A to 13G, the container 3100 is shown in a first configuration. In the first configuration, the analyte monitoring assembly 3116 is arranged in the container body 3102, and the closure 3110 is applied to close the container body 3102 (FIGS. 13A-13E). The sensor cap 3132 is coupled to the analyte monitoring assembly 3116 (specifically to the sensor control device 3118) and to the plug 3138, sealing the sensor 3128. The retaining element 3142 is positioned proximally of the ramp 3146. The sensor control device 3118 is retained in position by the alignment posts 3156 of the container body 3102 through the alignment holes 3158 in the lower shell 3122, and by the support element 3154 of the closure 3110 against the upper shell 3120 (best shown in FIG. 13F). In the first configuration, the analyte monitoring assembly 3116 is retained in position in the container body 3102.

In the first configuration, the sensor 3128 is sealed from the interior of the container body 3102. This means that the container body 3102 can be sterilized to a different degree, for instance using a different method, than the sensor 3128. This allows the sensor 3128 to be sterilized, for example using electron beam sterilization (e-beam). As e-beam sterilization can damage sensitive electronics, the sensor control device 3118 can be sterilized separately, such as by using ethylene oxide. The sensor cap 3132 thus forms a sterile barrier to the sensor 3128. In the first configuration, the closure 3110 forms a sterile barrier between the interior of the container body 3102 and the outside environment. In this regard, the container body 3102 does not require sterilization.

In some embodiments, the sensor 3128 and the sharp 3130 are sterilized. This is achieved by mounting the sensor 3128 to the lower shell 3122 of the sensor control device 3118. In particular, the proximal portion is attached to the lower shell 3122 for later connection to the electronics, while the distal portion extends perpendicularly from the lower shell 3122. The lower shell 3122 also includes the adhesive patch 3124. The sharp 3130 is supported by the sharp hub 3126, and the sharp hub 3126 engages the lower shell 3122 such that the sharp 3130 extends through an aperture in the lower shell 3122 and the sharp 3130 extends adjacent the sensor 3128 (similar to the embodiment shown in FIG. 14A, which will be later described herein). The sensor cap 3132 is attached to the lower shell 3122 over the sensor 3128 and the sharp 3130, and the plug 3138 is attached to the sensor cap 3132 to seal the sensor 3128 and the sharp 3130. These components together form a sterile sub-assembly (SSA). This can be sterilized together, such as by e-beam sterilization. The electronics can then be loaded onto the lower shell 3122 and the upper shell 3120 can be attached to form the housing of the sensor control device 3118. The sensor control device 3118 together with the SSA is best illustrated in FIG. 13C. This can be inserted into the container body 3102 for storage. In particular, the plug 3138 can engage the post 3140 and the lower shell 3122 can be aligned with the alignment posts 3156 (see, e.g., FIG. 13F). In other examples, other methods of sterilization can be performed, such as sterilizing and assembling different components in different orders, or by using different sterilization techniques such as ethylene oxide.

The container 3100 can be operated by moving the sensor cap 3132 from the first configuration into the second configuration in which the analyte monitoring assembly 3116 can be removed.

During operation, the closure 3110 can be removed by pulling the tab 3112 to overcome the seal between the lip 3150 and the engagement surface 3152 (tab 3112, lip 3150 and engagement surface 3152 best shown in FIGS. 13D and 13E). For instance, the user can remove the closure 3110 by hand. By removing the closure 3110, the analyte monitoring assembly 3116 is exposed, and the sensor control device 3118 is no longer supported distally by the supporting element 3154 (e.g., FIG. 13G). The container 3100 with the closure 3110 removed is shown in FIG. 13G. Following this, and as best depicted in FIGS. 13H-13J, an insertion apparatus 902 (otherwise referred to as an applicator or reusable applicator) can be used for removing the analyte monitoring assembly 3116 from the container body 3102 of the container 3100.

Figure 13J:
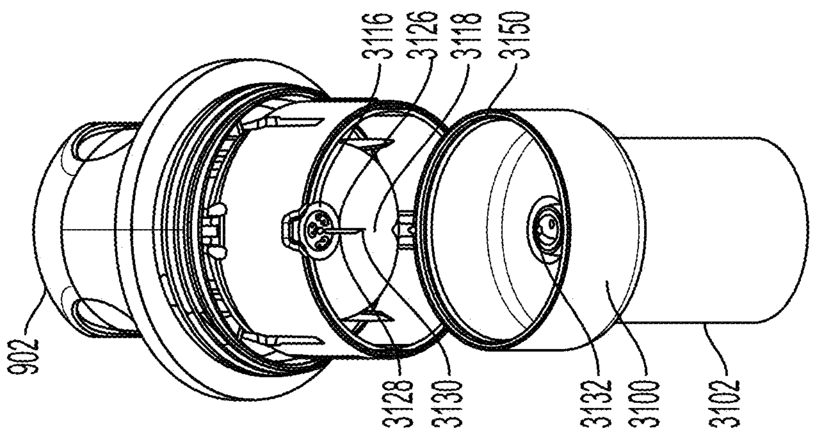
FIGS. 13H-13J are progressive views of the container in FIG. 13A in various stages of operation.
Figure 13I:
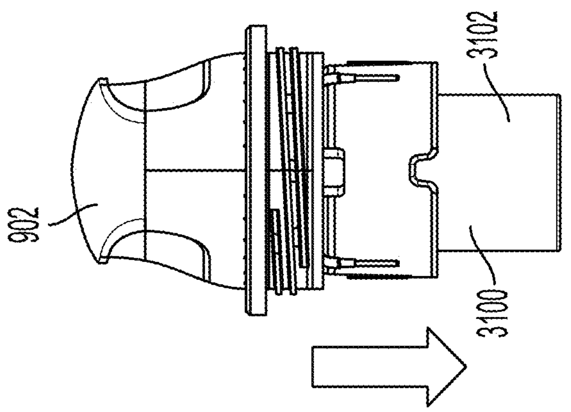
Figure 13H:
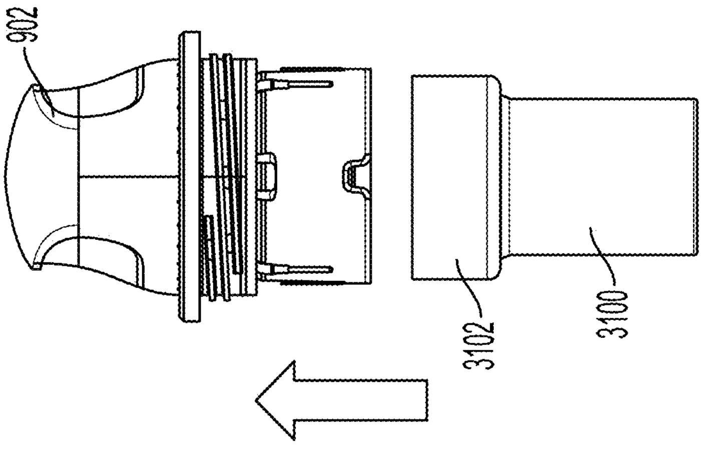

FIGS. 13H-13J depict the container 3100 in various stages of operation, wherein container 3100 is depicted with closure 3110 removed, and wherein the analyte monitoring assembly 3116 is withdrawn from container body 3102 of the container 3100 by an insertion apparatus 902 (which is similar to the insertion apparatuses described herein, e.g., the applicator 150, 702). As shown in FIGS. 13H-13J, the insertion apparatus 902 can be inserted into the container 3100 for removing the analyte monitoring assembly 3116. In some embodiments, the user can insert the insertion apparatus 902 by hand. In some embodiments, the container 3100 can have alignment features for aligning the insertion apparatus 902 relative to the analyte monitoring assembly 3116. The insertion apparatus 902 can be inserted into the container 3100 (FIGS. 13H-13I) in order to grip the analyte monitoring assembly 3116. According to an aspect of the embodiments, the insertion apparatus 902 is configured to grip the sensor control device 3118 using a device carrier (e.g., similar to the device carrier 710). In other examples, the insertion apparatus 902 can additionally be configured to grip the sharp hub 3126 (e.g., similar to the interaction of the sharp carrier 1102 and the hub snap pawl 2516 of the sharp hub 2500 as described herein).

As best illustrated in FIGS. 13I-13J, the insertion apparatus 902 can then be used to exert a proximal force on the analyte monitoring assembly 3116 relative to the container body 3102. For instance, the user can pull the insertion apparatus 902, and thus the gripped analyte monitoring assembly 3116, in the proximal direction (FIG. 13J). According to an aspect of the embodiments, and as best illustrated in FIG. 13J, the sensor cap 3132 remains within the container body 3102 of the container 3100 after removal of the analyte monitoring assembly 3116.

Figure 13K:
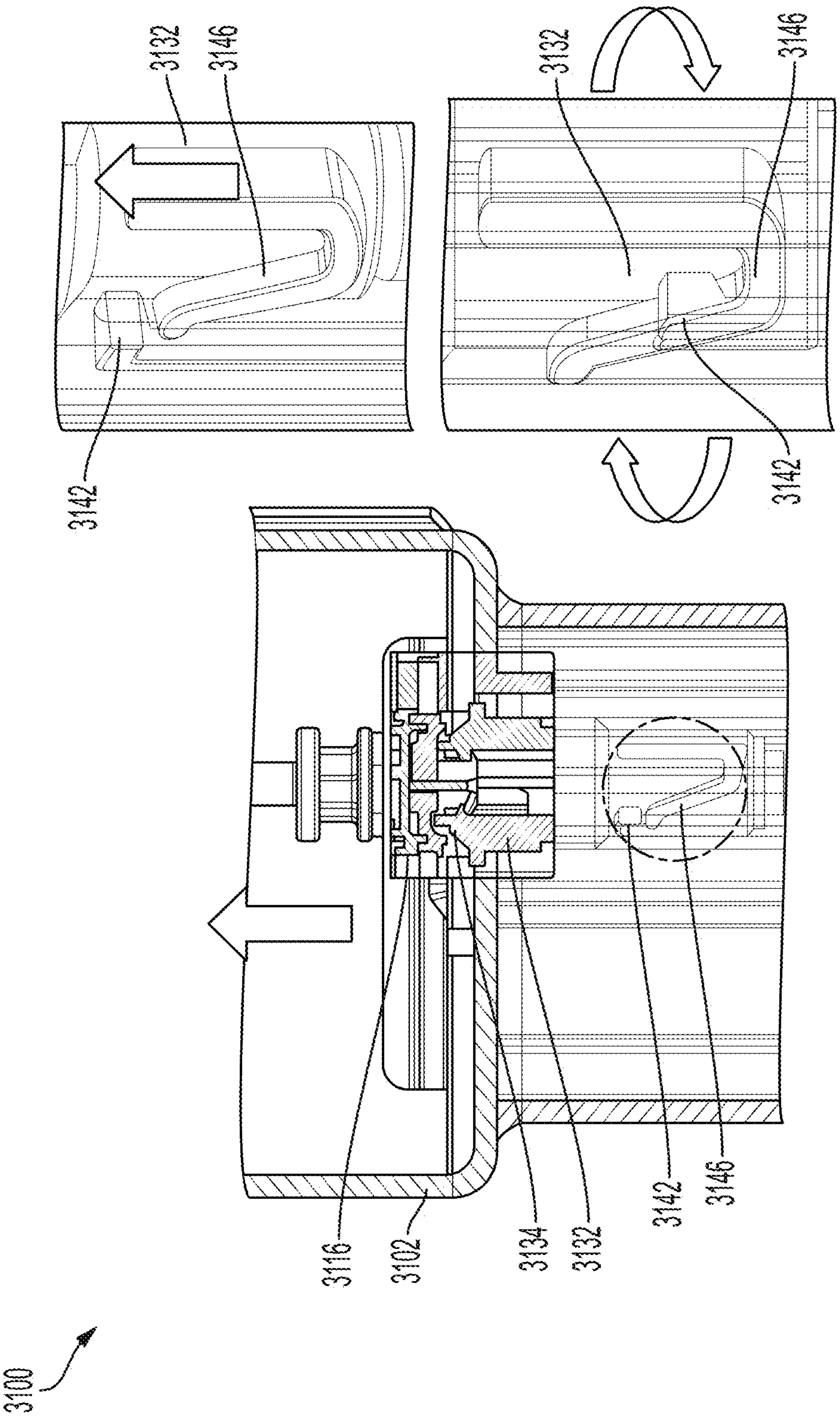
FIG. 13K is a close-up perspective cross-sectional view of the container in FIG. 13A, and a callout view of components therein.

Specifically, FIG. 13K illustrates the mechanism of removing the sensor cap 3132 from the analyte monitoring assembly 3116 as the container 3100 is being pulled away from the insertion apparatus 902 (not illustrated in FIG. 13K). In particular, FIG. 13K depicts a close-up perspective cross-sectional view of the container body 3102, and a callout view (as depicted by the broken-lined circle) of the retaining element 3142 of the container body 3102 engaging with the ramp 3146 of the sensor cap 3132. Due to application of the proximal force, the retaining element 3142 engages the ramp 3146. As previously described herein, this interaction prevents the sensor cap 3132 from being moved proximally under the force. Instead, the proximal force causes the retaining element 3142 to move along the ramp 3146. This forces the sensor cap 3132 to rotate relative to the container body 3102. In other words, the proximal force is converted into rotation of the sensor cap 3132. This rotation unscrews the sensor cap 3132 from the analyte monitoring assembly 3116. In particular, the first end 3134 of the sensor cap 3132 unscrews or detaches from the analyte monitoring assembly 3116 into the second configuration. This allows the analyte monitoring assembly 3116 to be released from the sensor cap 3132. This then allows the analyte monitoring assembly 3116 to be withdrawn from the container body 3102 by the insertion apparatus. Specifically, the analyte monitoring assembly 3116 is removable from the container body 3102 when the sensor cap 3132 is in the second configuration.

As illustrated in FIG. 13J, the analyte monitoring assembly 3116, including the sensor control device 3118 and the sensor 3128, are removed from the container body 3102 and can be loaded into the insertion apparatus 902. Because the sharp 3130 extends through the analyte monitoring assembly 3116 and the sharp hub 3126 engages the upper shell 3120 of the sensor control device 3118, the proximal movement of the analyte monitoring assembly 3116 also moves the sharp 3130 and the sharp hub 3126. The combination of the analyte monitoring assembly 3116 (including the sensor 3128 and the sensor control device 3118) and the sharp 3130 and sharp hub 3126 can together be referred to as a sterile sub-assembly, or an analyte insertion assembly. This assembly is withdrawn from the container body 3102 as one. Further, the sensor cap 3132 is left behind, and the sensor 3128 and the sharp 3130 are exposed.

As described herein, the insertion apparatus 902 can then be used to insert at least a portion of the sensor 3128 into the skin and to place the sensor control device 3118 onto the skin. For instance, the insertion apparatus 902 can be used to insert the sensor 3128 into the skin. In some examples, a portion of the sensor 3128 can be inserted into the skin (such as the tail 2408 of the sensor 104), whilst another portion of the sensor 3128 can remain outside of the skin (such as the contacts 2418). In other examples, the sensor 3128 can be considered as the insertable portion of the sensor structure (such as the tail 2408), and thus the entire sensor 3128 can be considered to be inserted. The sharp 3130 can be used to assist insertion of the sensor 3128. In some examples, the sharp 3130 (and the sharp hub 3126) is not provided at all. For example, the sensor 3128 can be configured to be inserted into the skin, and the insertion apparatus can be needle-free.

By providing the sensor control device 3118 and the sensor 3128 within the container body 3102, the analyte monitoring assembly 3116 can be assembled into the insertion apparatus 902 as a whole. The sharp 3130 and the sharp hub 3126 can also be loaded at the same time. This means that a reusable insertion apparatus can be provided, where the analyte monitoring assembly 3116 is loaded into the insertion apparatus each time. Thus, the container 3100 can be disposable.

Because the sensor cap 3132 is arranged and sealed over the sensor 3128 and the sharp 3130, the sensor 3128 and the sharp 3130 can remain sterile until use. The sensor cap 3132 can then be unscrewed by application of a proximal force in order to remove the sensor cap 3132 and allow removal of the analyte monitoring assembly 3116 from the container body 3102. This allows removal of the analyte monitoring assembly 3116 without contaminating the sensor 3128 or the sharp 3130.

Further, by causing rotation of the sensor cap 3132 in response to the proximal force, the sensor cap 3132 can be unscrewed from the analyte monitoring assembly 3116 without the user imparting a rotational force. This removes a step in the process, simplifying the insertion process.

Figure 13L:
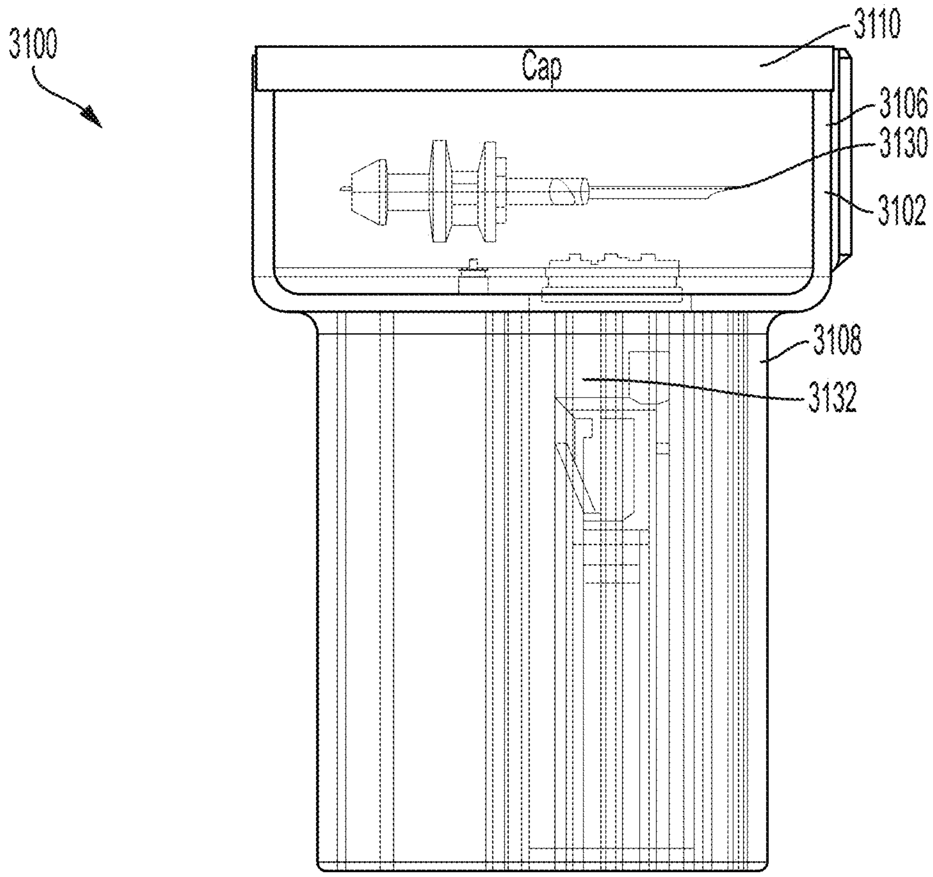
FIG. 13L is a perspective cross-sectional view of the container, in accordance with an exemplar embodiment of the disclosure.

In some embodiments, and with reference to FIG. 13L, after insertion of the sensor 3128 into the skin, the container 3100 can be used to dispose of the sharp 3130 after ejection of the sharp 3130 following insertion of the sensor 3128 (sensor 3128 not depicted in FIG. 13L). Generally, the sharp 3130 is used to insert the sensor 3128 into the skin, and then the sharp 3130 is withdrawn and disposed of. Conventionally, the sharp 3130 can be withdrawn into an insertion apparatus, which is then disposed of as a whole. However, with a reusable insertion apparatus, the entire insertion apparatus is not disposed of. Instead, the insertion apparatus is reused. However, the sharp 3130 must be removed from the insertion apparatus to allow for subsequent use of the insertion apparatus, and a new sharp 3130 is required each time. In some embodiments, the container 3100 can be used to store the sharp 3130 after use. In this regard, the container 3100 can be used as a receptacle for the used sharp 3130. In particular, the insertion apparatus can eject the sharp 3130 back into the container 3100 for safe disposal.

As shown in FIG. 13L, in some embodiments, the sharp 3130 can be ejected into the first portion 3106 of the container body 3102. Specifically, the sharp 3130 can be housed within the first portion 3106 of the container body 3102 in a horizontal orientation so as to not extend into the second portion 3108 of the container body 3102. Those of skill in the art will recognize that the sharp 3130 can be positioned in various orientations within the container body 3102. Further, the closure 3110 (e.g., a cap) can be applied to the container body 3102 so as to seal the container 3100 comprising the used sharp 3130 and prevent inadvertent contact therewith. In some embodiments, the container 3100 is disposable and the container 3100 comprising the used sharp 3130 and sensor cap 3132 can be disposed.

In other embodiments, a ramp 3146 may not be provided. Instead, the retaining element 3142 can engage the sensor cap 3132, and the user can manually rotate the container body 3102 relative to the insertion apparatus in order to unscrew the sensor cap 3132.

In other embodiments, the sensor cap 3132 is not be rotatable or screwed onto the analyte monitoring assembly 3116. Instead, the sensor cap 3132 can be removable by proximal movement. For instance, the sensor cap 3132 can be attached to the analyte monitoring assembly 3116 (e.g., sensor control device 3118) by a seal (e.g., a radial seal). In some embodiments, a seal can be formed by using a low strength adhesive configured to be strong enough to withstand drop, shock, and the sterilization process, but separable upon application of sufficient force. In some embodiments, the proximal force pulling on the analyte monitoring assembly 3116 may detach the sensor cap 3132 from the analyte monitoring assembly 3116 by overcoming the seal. The sensor cap 3132 can be attached to the container body 3102, or the retaining element 3142 can be provided to retain the sensor cap 3132 while the analyte monitoring assembly 3116 is released. Although this can simplify the design, ensuring an adequate seal to maintain sterility when needed whilst ensuring the sensor cap 3132 can be detached by pulling proximally can be difficult. Accordingly, the rotation as described with reference to the embodiments disclosed herein has advantages.

Example Embodiments of a Container Without a Separate Plug

Referring to FIGS. 14A-14D, example embodiments of container 4100 is provided.

According to an aspect of the embodiments, the container 4100 is similar to the container 3100, except as set out below. In particular, the container 4100 is identical to the container 3100, except that the container 4100 comprises a plug 4138 instead of a plug 3138.

Figure 14A:
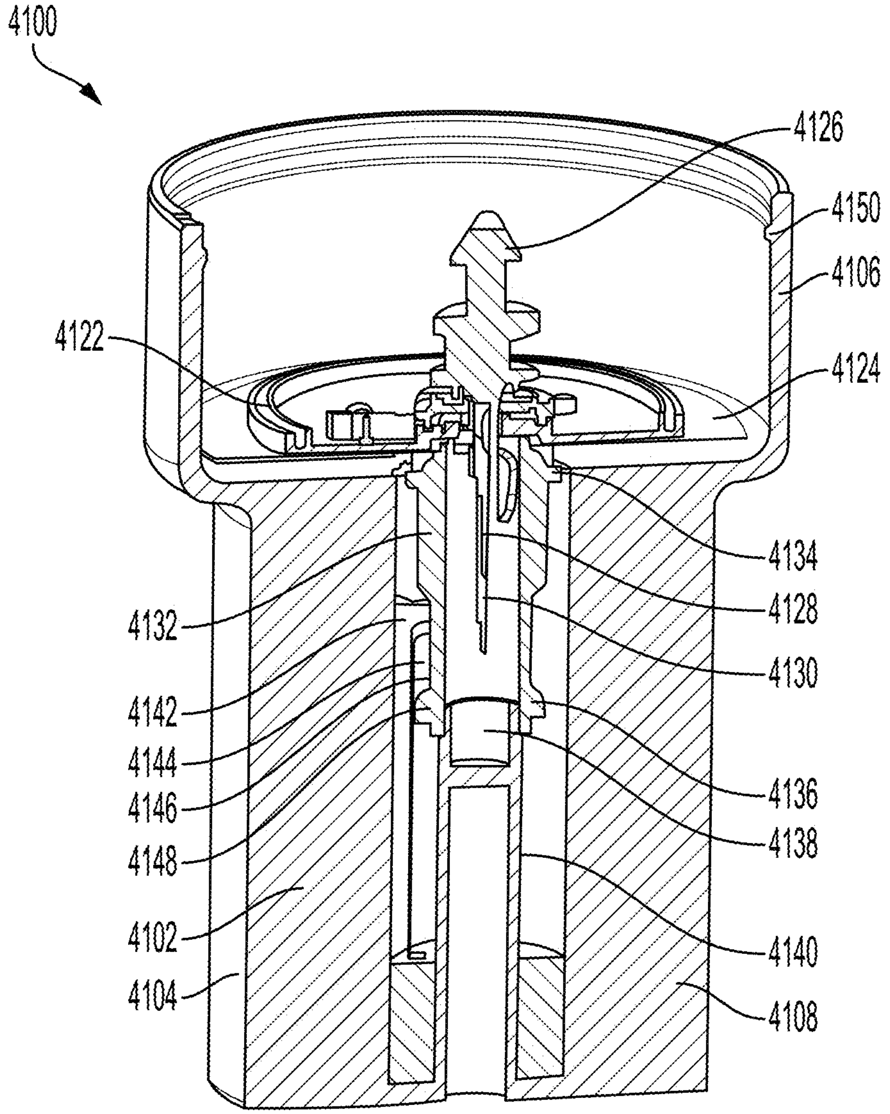
FIG. 14A is a perspective cross-sectional view of a container, in accordance with an exemplar embodiment of the disclosure.

FIG. 14A shows the container 4100 from a similar perspective as FIG. 13E. FIG. 14A shows the container 4100 with the closure 4110 removed similar to FIG. 13G. FIG. 14A also shows the container 4100 with the upper shell 4120 and sensor electronics of the sensor control device 4118 not yet inserted. In particular, FIG. 14A shows a state of partial assembly of the container 4100.

According to another aspect of the embodiments, container 4100 is identical to the container 3100, except that the container 4100 comprises a plug 4138 instead of the plug 3138. In some embodiments, the second end 4136 of the sensor cap 4132 is coupled to the plug 4138. The plug 4138 is integral with the post 4140 connected to the container body 4102. In other words, the plug 4138 is integral with the container body 4102. Thus, there is no separate plug 3138. In this manner, the container body 4102 itself is configured to seal the second end 4136 of the sensor cap 4132. In some embodiments, the second end 4136 fits over the plug 4138 to form a radial seal between the sensor plug 4132 and the container body 4102. In other embodiments, the sensor cap 4132 can fit inside walls of the plug 4138 to form a radial seal, or form another type of seal.

This means that the container body 4102 forms part of the sterile barrier for the sterile sub-assembly (SSA). To achieve this, the container body 4102 is sterilized in the same process as the sterile sub-assembly. In some embodiments, and as best depicted in FIG. 14A, the SSA is assembled into the container body 4102 before sterilization. That is, the sensor 4128 is attached to the lower shell 4122 (and lower shell 4122 has adhesive patch 4124), the sensor cap 4132 is attached to the lower shell 4122, the sharp hub 4126 is attached to the lower shell 4122 such that the sharp 4130 extends through the aperture of the lower shell 4122 and adjacent the sensor 4128, and the sensor cap 4132 is attached to the lower shell 4122 over the sensor 4128 and the sharp 4130, as in the embodiments depicted in FIGS. 13A-13L. The sensor cap 4132 at its second end 4136 is then attached to the plug 4138 of the container body 4102, and the lower shell 4122 is aligned with the alignment posts. Once the SSA is assembled into the container body 4102, the container body 4102 with the loaded components undergoes sterilization (such as e-beam sterilization).

Figure 14B:
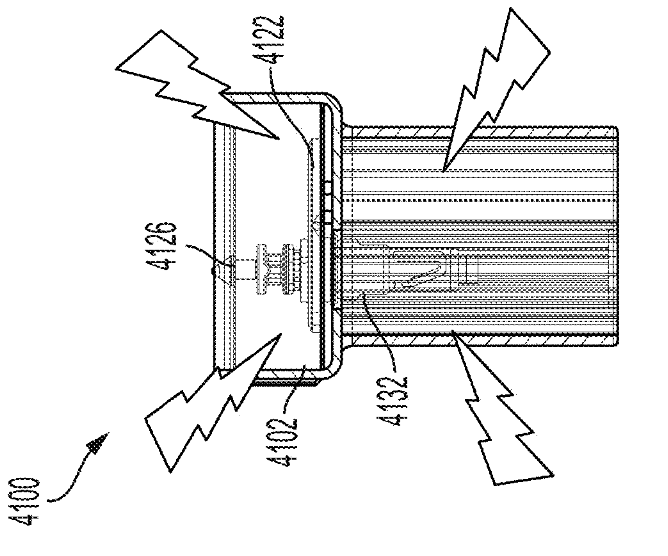
FIGS. 14B-14D are progressive views of the container of FIG. 14A in various stages of the sterilization process.
Figure 14C:
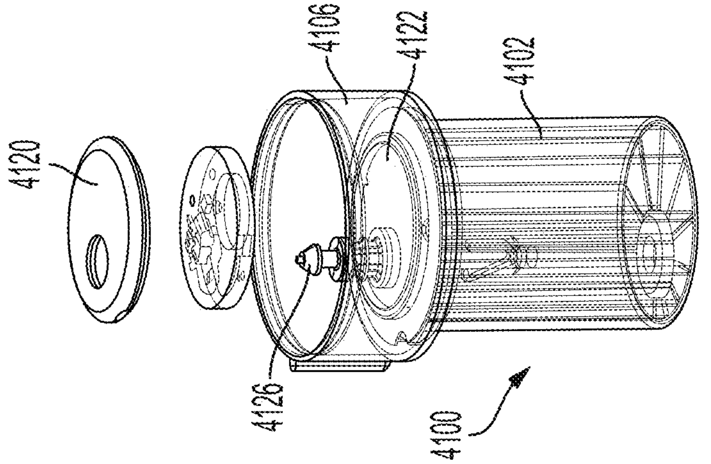
Figure 14D:
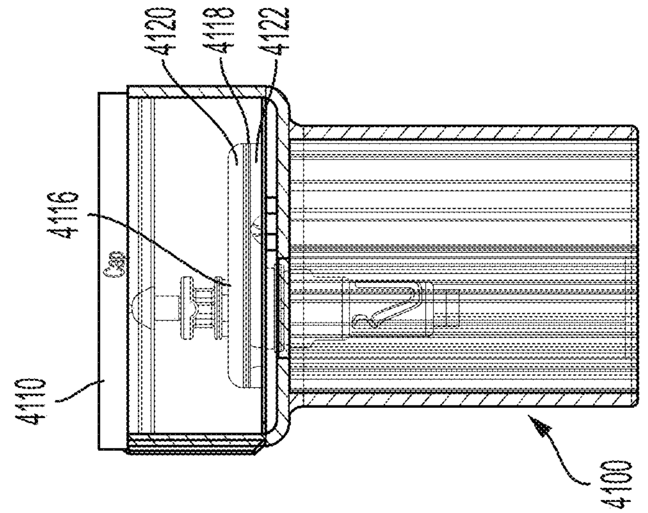

FIGS. 14B-14D are progressive views depicting the container body 4100 in various stages of the sterilization process. According to an aspect of the embodiments, the sterilization process allows the SSA to be sterilized in place. However, this requires assembly of the sensor electronics afterwards. In this way, space can be limited for automation of sensor electronics assembly. Thus, other embodiments, such as the embodiments described with reference to FIGS. 13A-13L, can simplify the automation of assembly.

Specifically, and as previously mentioned, in some embodiments, the container body 4102 undergoes e-beam sterilization with the SSA assembled therein. Thus, sterilization occurs after the SSA has been installed into the container 4100. This ensures that the container body 4102 (in particular the plug 4138, which is not depicted in FIGS. 14B-14D) is sterile so that it can form a sterile barrier with the sensor cap 4132. Following irradiation (e.g., e-beam sterilization of the container body 4102 with the SSA installed therein), sensor electronics can subsequently be installed (FIG. 14C). Specifically, and as illustrated in FIG. 14C, the sensor electronics are configured to be received in the first portion 4106 of the container body 4102 following sterilization of the SSA and container body 4102 of the container 4100. More specifically, upon installation, the sensor electronics and upper shell 4120 can then be assembled onto the lower shell 4122. Further, the upper shell 4120 is configured to interface with the lower shell 4122 so as to house the sensor electronics therebetween and form the sensor control device 4118 (best shown in FIG. 14D). In some embodiments, the upper shell 4120 clips into a groove defined in the lower shell 4122, but other attachment configurations are possible.

With reference to FIG. 14D, and upon installation of the analyte monitoring assembly 4116 within the container body 4102 of the container 4100, a closure 4110, similar to closure 3110, can be applied to the first end of the container body 4102. In this regard, the analyte monitoring assembly 4116 is positioned within the container body 4102 and the closure 4110 is closed over the first end of the container body 4102 to seal the analyte monitoring assembly 4116 in the container body 4102.

Example Embodiments of a Reset Tool

With reference to FIGS. 15A-15G, example embodiments of a reset tool 5100 will now be described.

The reset tool 5100 is provided for use with an applicator, such as the applicator 5150 described herein, wherein applicator 5150 is used for inserting at least a portion of a sensor into skin of a subject (e.g., inserting an analyte sensor, such as an in vivo glucose sensor), and is configured as a resettable applicator 5150 of a reusable type. For example, spent applicator 5150 can be reset and reused for subsequent insertion of another analyte sensor by a user. Specifically, a sharp carrier 5102 and device carrier 5710 can be reset and spring 5103 reloaded, and sheath 5704 can be reset so that reusable applicator 5150 can be reused for insertion of a subsequent sensor. For example, the reusable applicator 5150 may be used with the container 3100 or 4100 as described herein. In some examples, the applicator 5150 may be similar to other applicators described herein, except as explained below.

Figure 15A:
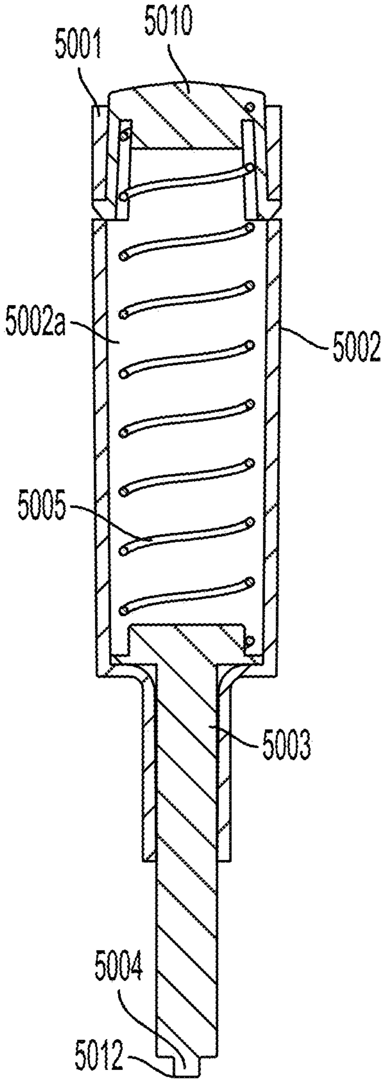
FIG. 15A depicts a side cutaway view of an example embodiment of a reset tool.
Figure 15B:
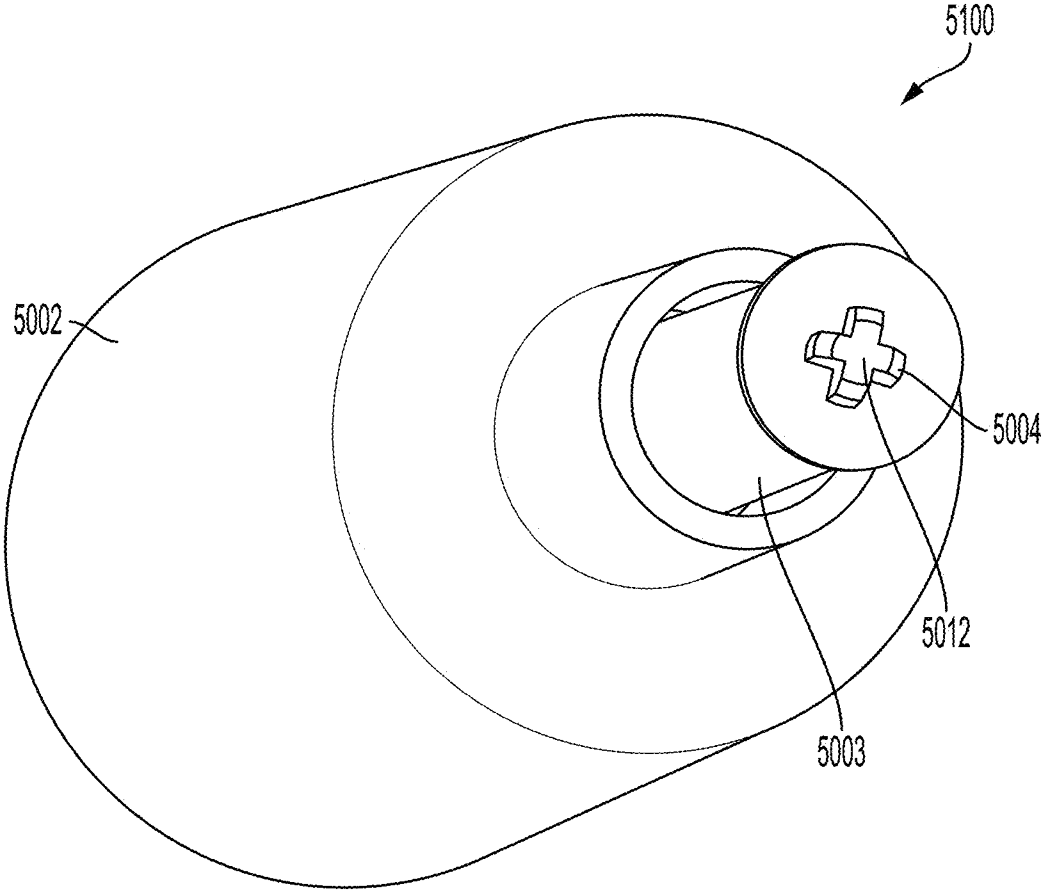
FIG. 15B depicts a bottom perspective view of the reset tool shown in FIG. 15A.

As shown in FIG. 15A, a side cutaway view of an example embodiment of reset tool 5100 is depicted without the applicator. As shown in FIG. 15A, and as will be described in further detail below with respect to FIGS. 15C-15G, reset tool 5100 comprises a handle 5001, a reset tool spring 5005 within a hollow interior 5002*a*, a cap 5010, a shaft 5002, a spring-loaded plunger 5003 (also referred to as a “plunger 5003”), and a stepped cylindrical section 5004 with tip portion 5012. FIG. 15B depicts a bottom perspective view of an example embodiment of reset tool 5100 comprising shaft 5002, plunger 5003, and stepped cylindrical section 5004 with tip portion 5012 comprising a cruciform shape or a shape with lead-in chamfers. Tip portion 5012 can also comprise a diamond shape, a round shape, a rectangular shape, or any other suitable shape sized to fit at least partially within sharp carrier 5102. Additionally, while the shaft 5002, the plunger 5003, and stepped cylindrical section 5004 are shown as cylindrical, any other suitable shape could be used.

Figure 15C:
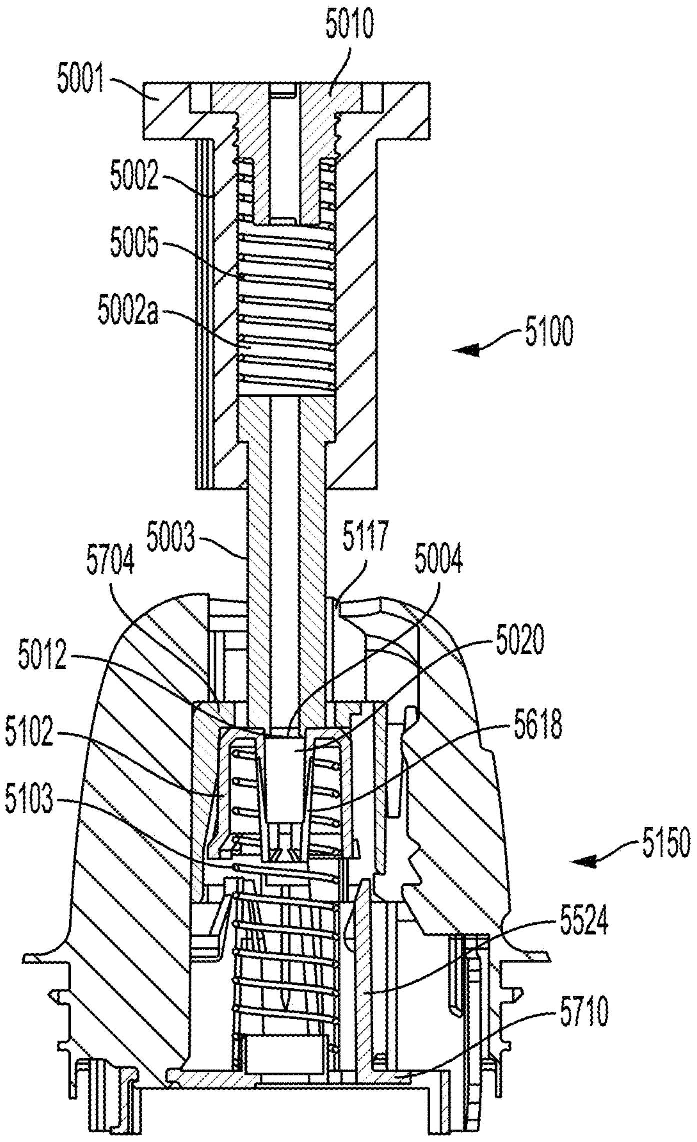
FIGS. 15C-15G are cross-sectional views depicting an example embodiment of an applicator and reset tool during various stages of resetting.
Figure 15E:
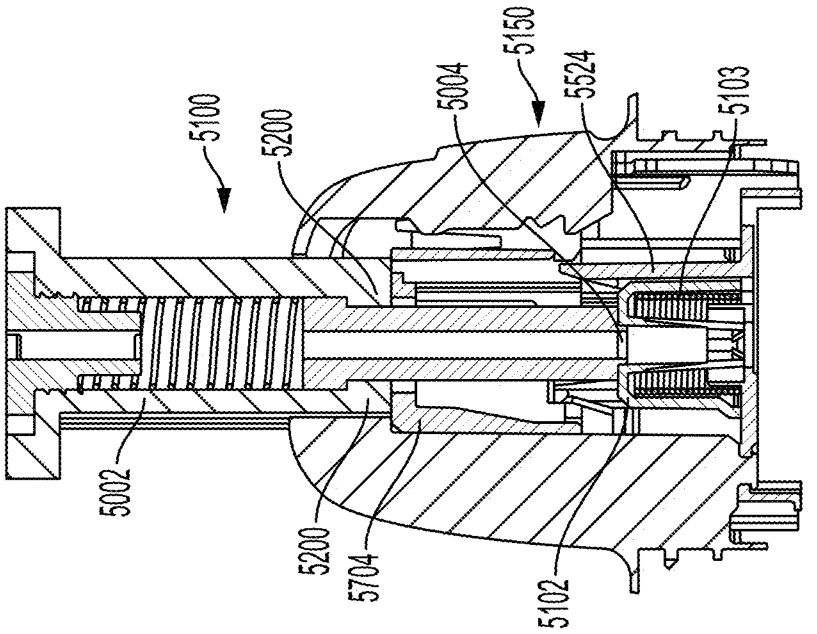
Figure 15D:
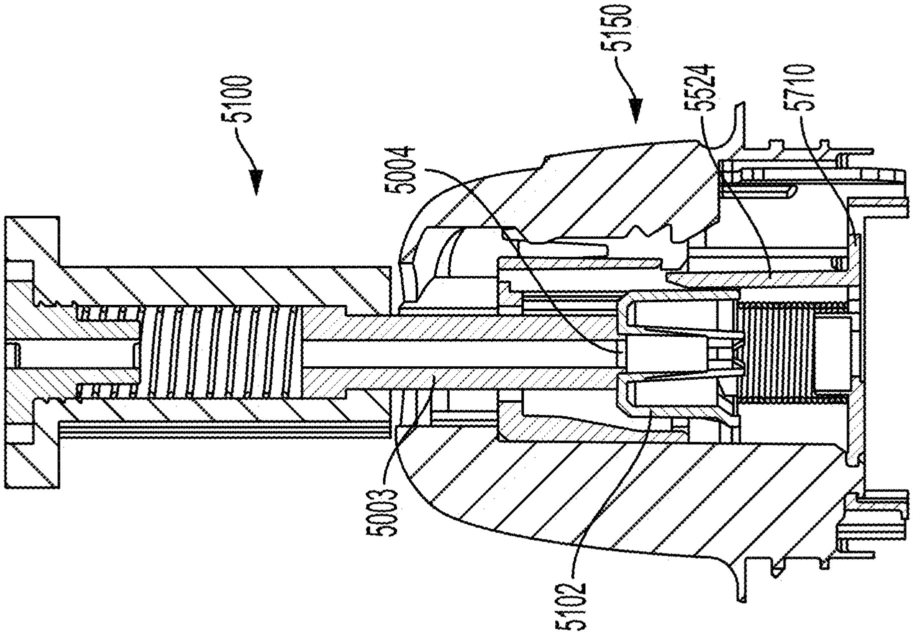
Figure 15F:
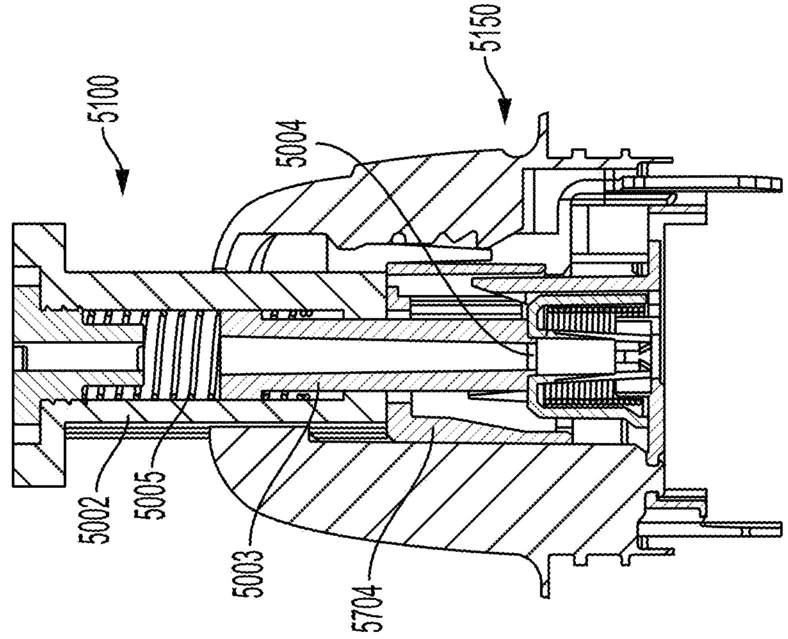
Figure 15G:
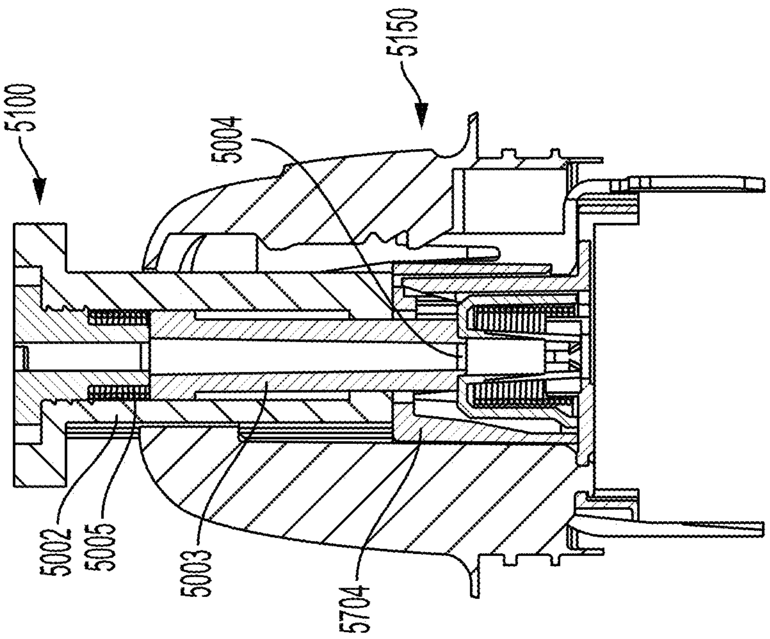

Turning to FIGS. 15C-15G, an example embodiment of a reusable applicator 5150 being “reset” using reset tool 5100 is depicted. As illustrated in FIGS. 15C-15G, reset tool 5100 can comprise shaft 5002 having a first longitudinal length, i.e., a first cylindrical section, telescopically coupled with spring-loaded plunger 5003 having a second longitudinal length, i.e., a second cylindrical section. In other words, the plunger 5003 telescopically slides within the shaft 5002. Other shapes besides cylindrical are possible, such as cuboid or conical. As best shown in FIG. 15G, the plunger 5003 can be sized and configured to be received within and telescopically slide with relative to the shaft 5002. In other words, a transverse dimension (e.g., a diameter) of the plunger 5003 is smaller than an opening of the shaft 5002 to enable the sliding movement. The proximal end of the plunger 5003 may comprise a larger dimension (e.g., diameter), for example forming a lip or a rim, to retain the plunger 5003 within the shaft 5002. Other retaining means, such as end stops or detents, may be provided in addition or instead. Further, the shaft 5002 can include hollow interior 5002*a* and a transverse dimension (e.g., a diameter) sized and configured for insertion into reusable applicator 5150. Specifically, the transverse dimension of the plunger 5002 can be inserted into a reset channel 5117 on a top portion of reusable applicator 5150 (e.g., through the outer housing, such as housing 702). The reset channel 5117 can be an aperture extending from the top portion of reusable applicator and axially aligned with the device carrier 5710 and sharp carrier 5102. In some examples, though not illustrated, a removable plug can be sized and configured to close the reset channel 5117 so as to seal reset channel from contaminants when reset tool is not being utilized with reset applicator 5150.

Additionally, hollow interior 5002*a* can house a reset tool spring 5005 configured to bias the plunger 5003 towards a distal end of the shaft 5002. The shaft 5002 can include handle 5001 for ergonomic use of reset tool 5100. The shaft 5002 can also comprise cap 5010 configured to cover a top portion of handle 5001. Specifically, a bottom portion of cap 5010 extends into hollow interior 5002*a* and interfaces with a first end of reset tool spring 5005. More specifically, a second end of reset tool spring 5005 can interface with a proximal portion of the plunger 5003 that is received within hollow interior 5002*a*. In this manner, reset tool spring 5005 is configured to compress and decompress a distance between the cap 5010 and the plunger 5003. In other words, the reset tool spring 5005 is engaged between the plunger 5003 and a surface of the shaft 5002. The surface of the shaft 5002 may be the cap 5010 or the cap 5010 may be omitted and the surface is a surface of the shaft 5002 defining an opposing end of the hollow interior 5002*a*. The cap 5010 may be removable, or it may be integral with the reset tool 5100.

A distal portion of the plunger 5003 can comprise stepped cylindrical section 5004 in axial alignment with the plunger 5003. A transverse dimension of the plunger 5003 (e.g., a diameter) can be sized and dimensioned for insertion into sheath 5704, while a transverse dimension (e.g., a diameter) of stepped cylindrical section 5004 can be sized and dimensioned for insertion into sharp carrier 5102. In this manner, the plunger 5003 can extend through the sheath 5704 and into the sharp carrier 5102. The stepped section 5004 may have other shapes besides cylindrical in other examples. In other examples, the stepped cylindrical section 5004 is not provided, and the transverse dimension (e.g. diameter) of the plunger 5003 extends through the sheath 5704 and into the sharp carrier 5102.

Specifically, stepped cylindrical section 5004 can extend from the distal portion of the plunger 5003 and comprises tip portion 5012 configured to be received within a channel 5020 of sharp carrier 5102. Specifically, tip portion 5012 can be received within a channel 5020 extending between sharp retention arms 5618. Tip portion 5012 can be configured so as to only partially extend into channel 5020 so as to interface with sharp carrier 5102. In some examples, the tip portion 5012 has a complementary shape to the sharp carrier 5102. For example, the tip portion 5012 may form a friction fit or interlocking fit with the sharp carrier 5102. In other examples, the tip portion 5012 simply contacts the sharp carrier 5102 sufficiently to engage the sharp carrier 5102 for pushing the sharp carrier 5102 as described herein.

As mentioned, the tip portion 5012 may be part of the stepped cylindrical section 5004. In some examples, the tip portion 5012 may be integral with the plunger 5003. In other examples, the tip portion 5012 may be separate from the plunger 5003 but may be coupled to the plunger 5003 such that movement of the plunger 5003 causes movement of the tip portion 5012. In some examples, the tip portion 5012 may be provided without the stepped section 5004.

With reference to FIGS. 15C-15G, the shaft 5003 has a larger transverse dimension than the plunger 5003, and the plunger 5003 has a larger transverse dimension than the stepped cylindrical section 5004. Moreover, both the plunger 5003 and stepped cylindrical section 5004 can be hollow, thereby reducing overall weight of reset tool 5100.

With particular reference to FIGS. 15C-15G, example details of embodiments of mechanics of "resetting" reusable applicator 5150 using reset tool 5100 are illustrated. In an initial step, referring to FIG. 15C, reset tool 5100 can be inserted into reset channel 5117 of reset applicator 5150. If the removable plug is sealing the reset channel 5117, then removable plug can first be removed so as to allow access to reset channel 5117 by reset tool 5100. As shown in FIG. 15C, reset tool 5100 is inserted into reset channel 5117 along a longitudinal axis of applicator 5150 until stepped cylindrical section 5004 engages sharp carrier. Specifically, reset tool 5100 is inserted into reset channel 5117 along a longitudinal axis of applicator 5150 until tip portion 5012 of stepped cylindrical section 5004 is at least partially inserted into channel 5020 of sharp carrier 5102. In doing so, the plunger 5003 passes through the reset channel 5117 in the housing and through an opening in the sheath 5704. In some examples, the shaft 5002 does not pass through the reset channel 5117 at this stage. The shaft 5002 can therefore remain external to the applicator. This is because the plunger 5003 may have a longitudinal dimension longer than the distance between the sharp support 5102 and the opening of the reset channel 5117 in the applicator. In other examples, the shaft 5002 may be received into the reset channel 5117 at this stage along with the plunger 5003.

With reference to FIG. 15D, as user force is further applied to advance reset tool 5100 in a distal direction into applicator 5150, the plunger 5003 drives sharp carrier 5102 towards device carrier 5710 until device carrier lock arms 5524 are cleared and the device carrier lock arms 5524 reengage sharp carrier 5102. As a result, and as shown in FIG. 15E, spring 5103 is recompressed and fully energized. Once sharp carrier 5102 is repositioned between device carrier lock arms 5524, the shaft 5002 engages an upper section of sheath 5704 (FIG. 15E). Specifically, and as best illustrated in FIG. 15E, one or more shoulder portions 5200 on the shaft 5002 engage the upper section of sheath 5704. At this point, the shaft 5200 is received into the channel 5117. In this manner, the reset tool 5100 can be used to push the sharp carrier 5102 against the spring 5103 until it is received by the device carrier 5710. This allows the position of the sharp carrier 5102 to be reset.

In other examples, a device carrier 5710 may not be present in the applicator, and for example the sharp carrier 5102 may carry the analyte monitoring assembly. In other words, the reset tool 5100 may generally be used to compress the retraction spring of the applicator in order to reset the applicator. For example, the reset tool 5100 may engage the sharp carrier 5102 and advance the sharp carrier 5102 to compress the spring. The sharp carrier 5102 may be compressed until it is retained by another component in order to retain the spring in the compressed state. Whilst this component may be a device carrier 5710, it may be another component such as a latch or detent.

As shown in FIGS. 15F-15G, as user force is continued to be applied to advance reset tool 5100 in a distal direction into applicator 5150, the shaft 5002 drives sheath 5704 in a distal direction so as to reset sheath 5704 to the pre-firing position, or the ready to fire position. Specifically, the shaft 5002 drives sheath 5704 in a distal direction until sheath 5704 extends out of applicator 5150 in the distal direction as it does in the pre-firing position. Additionally, as shown in FIGS. 15F-15G, the plunger 5003 collapses within the shaft 5002 and compresses reset tool spring 5005.

For example, this may be achieved by retaining the device carrier 5710 in position, and allowing the sheath 5704 to move distally. For example, the applicator 5150 may be held within a mount which supports the device carrier 5710 while allowing the sheath 5704 to advance distally. This allows the sheath 5704 to move relative to the sharp carrier 5102 and device carrier 5710.

The reset tool spring 5005 is compressed because the tip portion 5012 is supported against the sharp carrier 5102 which is now in the fully advanced position and engaged with the device carrier 5710. This provides a contact force (e.g., from the mount in which the applicator is supported), which exerts a proximal force on the plunger 5003 when the shaft 5002 is advanced distally. This force acts to compress the reset tool spring 5005.

Following this, and after the sheath has returned to the pre-firing position, user force can be removed from reset tool 5100. As a result, though not illustrated, compressed force of reset tool spring 5005 can drive the shaft 5002 in a proximal direction. Reset tool spring 5003 can comprises a force greater than a force of spring 5103. Reset tool spring 5005 is configured such that its force can overcome the force of spring 5103. This allows the spring 5103 to be compressed by the plunger 5003 without compressing the reset tool spring 5005. Though not illustrated, after the shaft 5002 has fully retracted in the proximal direction, reset tool 5100 can be removed from applicator 5150. Additionally, the user can manually exert a force in a proximal direction so as to remove reset tool 5100 from applicator 5150.

If a removable plug is utilized, removable plug can be replied to seal reset channel 5117. At this stage, applicator 5150 has been reset. The reset tool 5100 can be utilized with an applicator 5150 for demonstration purposes, as well. For example, when applicator 5150 does not have a sharp, reset tool can be utilized to reset applicator 5150. Additionally, user can manually load sensor control device 5102 into applicator. When utilized for demonstrative purposes, sensor control device 5102 does not include electronics or an adhesive.

Although not depicted, reusable applicator 5150 can also include any of the embodiments of sensor control device, analyte sensors, and sharps described herein, or in other publications which have been incorporated by reference. Reusable applicator can be advantageous in that it can be reused, thereby reducing overall cost to consumers and environmental impact.

Though not illustrated, reset tool 5100 and applicator 5150 can be provided together or separately in a demonstration kit box. Demonstration kit box can also include one or more sensor control devices without adhesives (e.g., three sensor control devices) so as to allow the user to load the sensor control device(s) into application for demonstrative purposes. Demonstration kit box can also include a reader device.

Reset tool 5100 can be formed from plastic material. Specifically, reset tool can be made up of polycarbonate acrylonitrile-butadiene-styrene ("PC/ABS") material. Those of skill in the art will appreciate that other materials can be utilized for the reset tool 5100 without departing from the scope of the present disclosure.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

In summary, systems, devices and methods are provided for inserting at least a portion of a sensor for sensing an analyte level in a bodily fluid of a subject. In particular, disclosed herein are various embodiments of containers for storing an analyte monitoring assembly. The analyte monitoring assembly can be a combination of components used for monitoring an analyte of the subject. The containers described herein can be used to load an analyte monitoring assembly into an insertion apparatus. The insertion apparatus can then be used to insert at least a portion of the sensor into the subject's skin. The insertion apparatus can be reusable.

What is claimed is:

1. A reset tool for resetting an applicator, the reset tool comprising:

a shaft comprising a hollow interior;

a spring-loaded plunger configured to telescopically slide relative to the shaft, the plunger further configured to be inserted into a channel of the applicator; and a tip portion configured to extend into a channel of a sharp carrier of the applicator, wherein the reset tool is configured to advance in a distal direction into the applicator in response to a force, wherein the plunger is further configured to drive the sharp carrier towards a device carrier of the applicator until a portion of the device carrier engages with the sharp carrier, and wherein the shaft is configured to drive a sheath of the applicator in a distal direction upon the portion of the device carrier engaging with the sharp carrier.

2. The reset tool of claim 1, further comprising a compressible spring housed within the hollow interior of the shaft.

3. The reset tool of claim 2, wherein the plunger is further configured to collapse within the shaft and compress the spring, and wherein the compressed spring is configured to drive the shaft in a proximal direction.

4. The reset tool of claim 3, wherein the compressed spring is configured to have a first force that is greater than a second force of a spring within the applicator.

5. The reset tool of claim 1, wherein the shaft comprises a first cylindrical section and the plunger comprises a second cylindrical section, wherein a diameter of the shaft is greater than a diameter of the plunger.

6. The reset tool of claim 1, wherein the shaft further comprises a handle and a cap, wherein the cap is configured to cover a top portion of the handle.

7. The reset tool of claim 1, wherein the tip portion comprises a stepped cylindrical section, and wherein a diameter of the tip portion is smaller than a diameter of the plunger.

8. The reset tool of claim 1, wherein the applicator comprises a spring, and wherein the spring of the applicator is configured to recompress in response to the sharp carrier driving towards the device carrier of the applicator.

9. The reset tool of claim 1, wherein the applicator is configured to insert at least a portion of an analyte sensor into a skin of a subject.

10. The reset tool of claim 1, wherein the tip portion comprises lead-in chamfers.

11. The reset tool of claim 1, wherein a proximal end of the plunger comprises a rim configured to retain the plunger within the shaft.

12. The reset tool of claim 1, wherein the channel of the applicator comprises an aperture configured to extend from a top portion of the applicator and axially align with the device carrier and sharp carrier.

13. The reset tool of claim 1, further comprising a removable plug configured to seal the channel of the applicator from contaminants when the reset tool is not in use with the applicator.

14. The reset tool of claim 1, wherein the shaft further comprises a cap, wherein the cap comprises a bottom portion configured to extend into the hollow interior.

15. The reset tool of claim 14, further comprising a compressible spring housed within the hollow interior of the shaft, wherein the spring comprises a first end and a second end, and wherein the bottom portion of the cap is further configured to interface with the first end.

16. The reset tool of claim 15, wherein the second end is configured to interface with a proximal end of the plunger.

17. The reset tool of claim 16, wherein the spring is configured compress and decompress a distance between the cap and the plunger.

18. The reset tool of claim 14, wherein the cap is removable.

19. The reset tool of claim 1, wherein the tip portion is configured to form a friction fit with the sharp carrier.

20. The reset tool of claim 1, wherein the reset tool is formed from a plastic material.

* * * * *